(12) United States Patent
Kim et al.

(10) Patent No.: US 7,973,060 B2
(45) Date of Patent: Jul. 5, 2011

(54) FAB I INHIBITOR AND PROCESS FOR PREPARING SAME

(75) Inventors: Cheol Min Kim, Seoul (KR); Dong Gyu Shin, Seoul (KR); Seonggu Ro, Seoul (KR); Joong Myung Cho, Seoul (KR); Young Lan Hyun, Seoul (KR)

(73) Assignee: CrystalGenomics, Inc., Seuol (KR)

( * ) Notice: Subject to any disclaimer, the term of this patent is extended or adjusted under 35 U.S.C. 154(b) by 827 days.

(21) Appl. No.: 11/548,349

(22) Filed: Oct. 11, 2006

(65) Prior Publication Data

US 2007/0135465 A1 Jun. 14, 2007

Related U.S. Application Data

(60) Provisional application No. 60/827,029, filed on Sep. 26, 2006, provisional application No. 60/726,814, filed on Oct. 13, 2005.

(51) Int. Cl.
*A61K 31/4412* (2006.01)
*C07D 213/69* (2006.01)

(52) U.S. Cl. ........................ 514/348; 546/296

(58) Field of Classification Search ................... None
See application file for complete search history.

(56) References Cited

U.S. PATENT DOCUMENTS

| | | | |
|---|---|---|---|
| 3,146,229 | A | 8/1964 | Cutler |
| 3,853,900 | A | 12/1974 | Shone |
| 5,278,163 | A | 1/1994 | Ogura et al. |
| 5,851,952 | A | 12/1998 | Karp et al. |
| 2004/0167123 | A1 * | 8/2004 | Pratt et al. ............. 514/223.2 |

FOREIGN PATENT DOCUMENTS

| | | | |
|---|---|---|---|
| EP | 0 707 001 A1 | | 4/1996 |
| WO | WO 03068230 A1 | * | 8/2003 |
| WO | 2004/043927 A1 | | 5/2004 |
| WO | 2004/064837 A1 | | 8/2004 |

OTHER PUBLICATIONS

Bossharth et al, Organic Letters, (2003), vol. 5, No. 14, pp. 2441-2444.*
European Search Report issued in corresponding EP Application No. 06799211.5, dated Mar. 7, 2011.
Srinivas et al., "Synthesis and Antibacterial Activity of 2,4,6-tri Substituted s-Triazines," 2005, Bioorganic & Medicinal Chemistry Letters, vol. 15, No. 4, pp. 1121-1123.
Conreaux et al., "A Practical Procedure for the Selective N-Alkylation of 4-Alkoxy-2-Pyridones and its Use in a Sulfone-Mediated Synthesis of N-Methyl-4-Methoxy-2-Pyridone," 2005, Tetrahedron Letters, vol. 46, No. 46, pp. 7917-7920.
Samaritani et al., "Organometallic Alkylation of 2-Chloro-4,6-Dimethoxy-1,3,5-Triazine: A Study," 2005, vol. 61, No. 18, pp. 4475-4483.
Wada et al., "Synthesis of 5-Substituted Pyrimidines. Ortho-Directed Lithiation of Pyrimidine Derivatives [1]," 1990, J. Heterocyclic Chem., vol. 27, No. 6, pp. 1831-1835.
Mattson et al., "Ortho-Directed Lithiation in Pi-Deficient Diazinyl Heterocycles," 1990, J. Org. Chem., vol. 55, No. 10, pp. 3410-3412.
Bossharth et al., "Palladium-Mediated Three-Component Synthesis of Furo[2,3-b]pyridones by One-Pot Coupling of 3-Iodopyridones, Alkynes, and Organic Halides," 2003, Organic Letters, vol. 5, No. 14, pp. 2441-2444.
Jeong et al., "An Efficient Synthesis of 3-Substituted 3H-Pyrimidin-4-Ones," 2004, Organic Letters, vol. 6, No. 6, pp. 1013-1016.
Prystas et al., "Synthesis of Substituted 1-Glycosyl-4-Benzyloxy-6(1H)-Pyrimidones by the Mercuri Process," 1967, Collection of Czechoslovak Chemical Communications, vol. 33, No. 1, pp. 210-222.

* cited by examiner

*Primary Examiner* — Zinna N Davis
(74) *Attorney, Agent, or Firm* — Sughrue Mion, PLLC

(57) ABSTRACT

A compound which is effective for inhibiting Fab I, and a method for treating a bacterial infection.

18 Claims, No Drawings

FAB I INHIBITOR AND PROCESS FOR PREPARING SAME

This application claims benefit of 60/827,029 filed Sep. 26, 2006 and claims benefit of 60/726,814 filed Oct. 13, 2005.

FIELD OF THE INVENTION

The present invention relates to a novel compound for inhibiting Fab I involved in bacterial fatty acid biosynthesis. This application claims priority under 35 U.S.C. 119(e) to the Provisional application 60/726,814, filed on Oct. 13, 2005, entitled "Novel Fab I Inhibitor And Process For Preparing Same," and to Provisional application 60/827,029 filed on Sep. 26, 2006, both of which are hereby incorporated by reference.

DESCRIPTION OF THE PRIOR ART

Fatty acid synthase (FAS) is involved in the overall biosynthetic pathway of saturated fatty acids in all organisms, but the structural organization of FAS varies considerably among them. The distinctive characteristics of FAS of vertebrates and yeast are that all enzymatic activities are encoded on one or two polypeptide chains, and that the acyl carrier protein (ACP) exists in the form of a complex. In contrast, in bacterial FAS, each of synthetic steps is catalyzed by a distinct, monofunctional enzyme and the ACP is a discrete protein. Therefore, it is possible to selectively inhibit bacterial FAS by blocking one of the synthetic steps using an inhibitory agent.

NADH-dependent enoyl-ACP reductase (Fab I) is involved in the last step of the four reaction steps involved in each cycle of bacterial fatty acid biosynthesis. (See Payne et al., *Drug Discovery Today* 6, 2001, 537-544). The first step, the condensation of malonyl-ACP with acetyl-CoA (Fab H), is catalyzed by β-ketoacyl-ACP synthase. The second step is ketoester reduction by NADPH-dependent β-ketoacyl-ACP reductase (Fab G). Subsequent dehydration by β-hydroxyacyl-ACP dehydrase (Fab A or Fab Z) leads to trans-2-enoyl-ACP. Finally, in the fourth step, trans-2-enoyl-ACP is converted to acyl-ACP having two additional carbon atoms by Fab I. Such a cycle is repeated, eventually leading to palmitoyl-ACP (16C), whereupon the cycle is stopped due to inhibition of Fab I by palmitoyl-ACP (see Heath et al., *J. Biol. Chem.* 271, 1996, 1833-1836). Thus, Fab I is the biosynthetic enzyme in the overall synthetic pathway of bacterial fatty acid biosynthesis.

Recent studies have shown that Fab I is the target for a broad spectrum antibacterial agent such as triclosan (see McMurry et al., *Nature*, 1998, 394, 531-532) or diazaborine (see Baldock et al., *Science*, 1996, 274, 2107-2110). Also, diazaborine has been reported to function as an irreversible inhibitor of Fab I through the formation of a covalent complex with Fab I (see Baldock et al., *Biochem. Pham.*, 1998, 55, 1541-1549), while triclosan is a reversible inhibitor of Fab I (see Ward et al., *Biochem.*, 38, 12514-12525).

PCT Publication No. WO 2001/027103 discloses Fab I inhibitors represented by the following formula or pharmaceutically acceptable salts thereof:

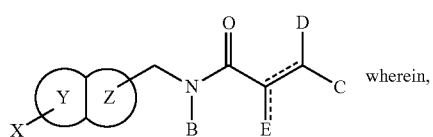

wherein,

-continued

B is H, $C_{1-4}$ alkyl or $C_{3-6}$ cycloalkyl;

C is 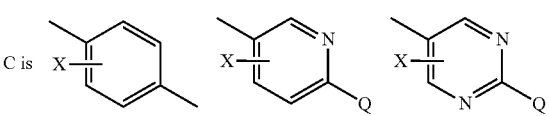

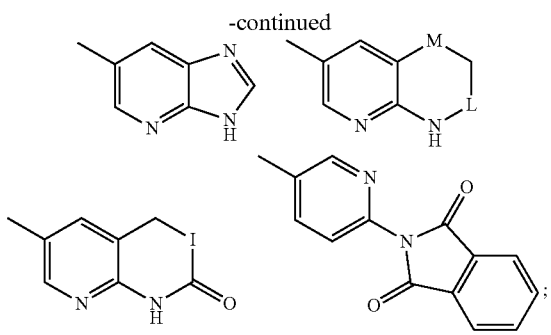

D is H or $C_{1-4}$ alkyl;

E is $CH_2$ when the bond to which it is attached is a double bond; or E is H or $C_{1-4}$ alkyl when the bond to which it is attached is a single bond, in which A is H or $C_{1-4}$ alkyl;

F is H or $C_{1-4}$ alkyl;

G is H, $C_{1-4}$ alkyl or $C_{0-6}$ alkylaryl;

I is O or $NR'_2$;

Q is H, $C_{1-4}$ alkyl, $N(R')_2$, NHC(O)R', NHCH$_2$C(O)R' or NHC(O)CH=CHR';

X is each independently H, $C_{1-4}$ alkyl, $CH_2OH$, OR', SR', CN, $N(R')_2$, $CH_2N(R')_2$, $NO_2$, $CF_3$, $CO_2R'$, $CON(R')_2$, COR', F, Cl, Br, I or —S(O)$_r$CF$_3$ (r is 0, 1 or 2);

W is S or O;

M is $CH_2$ or O;

L is $CH_2$ or C(O); and

R' is each independently H, $C_{1-4}$ alkyl or $C_{0-6}$ alkylaryl.

In addition, PCT Publication Nos. WO 2004/052890 and WO 2004/064837 and Canadian Patent No. 2,444,957 disclose a Fab I inhibitor for bacterial treatment.

The present inventors have developed a novel Fab I inhibitor which has broad antibacterial activity against Gram positive bacteria including methicillin resistant *Staphylococcos Aureus* (MRSA).

SUMMARY OF THE INVENTION

It is an object of the present invention to provide a novel compound which efficiently inhibits Fab I and is useful for the treatment of bacterial infections.

In accordance with one aspect of the present invention, there is provided a compound of formula (I) or (II) or a pharmaceutically acceptable analog thereof selected from the group consisting of salt, acid, ester, amide, and nitrile:

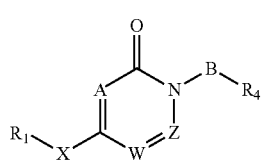 (I)

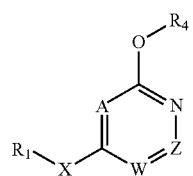 (II)

wherein, $R_1$ is selected from the group of radicals consisting of:

(a) H, (b) $C_{1-8}$ alkyl, $C_{1-8}$ alkenyl, $C_{1-8}$ alkynyl, (c) aryl, $C_{3-8}$ cycloalkyl, $C_{3-8}$ cycloalkenyl, (d) an analog of a radical of group (c) containing one or more heteroatoms selected from N, S or and O, and (e) a substituted analog of a radical selected from the group consisting of groups (b), (c), and (d), said substituted analog containing one or more substituents selected from the group consisting of:

hydroxyl, halogen, $C_{1-6}$ alkyl, $C_{3-8}$ cycloalkyl, $C_{3-8}$ heterocycloalkyl, alkyloxy, amino, alkylamino, carboxyl, nitro, sulfonylamide, alkylsulfonyl, amide, dioxoisoindole, trihaloalkyl, aryl, heteroaryl, substituted aryl, and substituted heteroaryl, wherein said substituted aryl and substituted heteroaryl contain one or more substituents selected from the group consisting of $C_{1-6}$ alkyl, $C_{3-8}$ cycloalkyl, $C_{3-8}$ heterocycloalkyl, alkyloxy, amino, alkylamino, carboxyl, nitro, sulfonylamide, alkylsulfonyl, amide, dioxoisoindole, trihaloalkyl, aryl;

A is selected from the group consisting of C—$R_2$ and N;

$R_2$ is selected from the group consisting of H, $C_{1-5}$ alkyl, benzyl, and substituted $C_{1-5}$ alkyl containing one or more substituents selected from the group consisting of methyl, ethyl, hydroxyl, hydroxylmethyl and hydroxylethyl;

B is selected from the group consisting of carbonyl, $CH_2$ and NH;

$R_4$ is selected from the group of radicals consisting of:

(a) $C_{1-8}$ alkyl, $C_{1-8}$ alkenyl, $C_{1-8}$ alkynyl, (b) aryl, $C_{3-8}$ cycloalkyl, $C_{3-8}$ cycloalkenyl, (c) an analog of a radical of group (b) containing one or more heteroatoms selected from N, S and O, and (d) a substituted analog of a radical selected from the group consisting of groups (a), (b), and (c), said substituted analog containing one or more substituents selected from the group consisting of:

hydroxyl, halogen, $C_{1-6}$ alkyl, $C_{3-8}$ cycloalkyl, $C_{3-8}$ heterocycloalkyl, alkyloxy, amino, alkylamino, carboxyl, nitro, sulfonylamide, alkylsulfonyl, amide, dioxoisoindole, trihaloalkyl, aryl, heteroaryl, substituted aryl, and substituted heteroaryl, wherein said substituted aryl and substituted heteroaryl contain one or more substituents selected from the group consisting of: $C_{1-6}$ alkyl, $C_{3-8}$ cycloalkyl, $C_{3-8}$ heterocycloalkyl, alkyloxy, amino, alkylamino, carboxyl, nitro, sulfonylamide, alkylsulfonyl, amide, dioxoisoindole, trihaloalkyl, and aryl;

W is selected from the group consisting of C—$R_6$ and N;

Z is selected from the group consisting of C—$R_5$ and N;

$R_5$ and $R_6$ are each independently selected from the group consisting of H, halogen, $C_{1-5}$ alkyl, and substituted $C_{1-5}$ alkyl containing one or more substituents selected from the group consisting of methyl, ethyl, hydroxyl, hydroxylmethyl and hydroxylethyl; and X is selected from C, N, O and S.

DETAILED DESCRIPTION OF THE INVENTION

In accordance with one aspect of the present invention, there is provided a novel compound of formula (I) or (II), or a pharmaceutically acceptable salt thereof.

The term "heteroaryl" as used herein means an aryl group containing one or more heteroatoms selected from N, S or O in the ring structure. Exemplary heteroaryls include those derived from pyrrole, pyrazole, imidazole, 1,2,3-triazole, 1,2,4-triazole, furan, isoxazole, oxazole, thiophene, isothiazole, thiazolidine, thiazole, 1,2,5-oxadiazole, 1,2,3-oxadiazole, 1,2,5-thiodiazole, 1,2,3-thiodiazole, 1,3,4-oxadiazole, 1,3,4-thiodiazole, pyridine, pyrimidine, tetrazole and triazine.

The term "bacteria-related diseases" as used herein means illnesses or conditions which are caused by bacterial infection and may be alleviated or relieved by a Fab I inhibitor treatment, and may include but are not limited to urinary tract, respiratory or skin tissue infections, sepsis, etc.

It is to be understood that the inventive compound may contain asymmetric centers of R or S configuration and thus the present invention includes geometrical isomers, stereoisomers and racemic mixtures of the compound of formula (I) or (II).

The pharmaceutically acceptable salt of the inventive compound which may be a non-toxic addition salt may be prepared by using an acid or base. Exemplary acids which may be used in the present invention include such inorganic acids as hydrochloric, hydrobromic, phosphoric and sulfuric acid; and an organic acid such as an organic carboxylic acid, e.g., acetic, trifluoroacetic, citric, formic, maleic, oxalic, succinic, benzoic, tartaric, fumaric, mandelic, ascorbic and malic acid, methanesulfonic acid and p-toluenesulfonic acid. Exemplary bases which may be used in the present invention include such inorganic bases as an alkali metal hydroxide (e.g., sodium hydroxide and potassium hydroxide), an alkali metal bicarbonate (e.g., sodium bicarbonate and potassium bicarbonate), an alkali metal carbonate (e.g., sodium carbonate, potassium carbonate and calcium carbonate) and an organic base such as amines.

The inventive compound may also be used in the form of a pharmaceutically acceptable derivative or prodrug which has a suitable ester or amide group. Preferable examples of the ester which can be hydrolyzed chemically or biochemically in the living body include indanyl, phthalidyl, pivaloyloxymethyl, glycyloxymethyl, phenylglycyloxymethyl, and 5-methyl-2-oxo-1,3-dioxorene-4-ylmethyl esters.

The preferred compounds of the present invention are as follows:
4-benzyloxy-1-(2-chloro-benzyl)-1H-pyridin-2-one;
4-benzyloxy-1-(4-chloro-benzyl)-1H-pyridin-2-one;
4-benzyloxy-1-(4-nitro-benzyl)-1H-pyridin-2-one;
4-benzyloxy-1-(2,5-dichloro-benzyl)-1H-pyridin-2-one;
4-benzyloxy-1-(2,4-dichloro-benzyl)-1H-pyridin-2-one;
4-benzyloxy-2-(4-methoxy-benzyloxy)-pyridine;
4-benzyloxy-1-(4-methoxy-benzyl)-1H-pyridin-2-one;
4-benzyloxy-2-(4-methyl-benzyloxy)-pyridine;
4-benzyloxy-1-(4-methyl-benzyl)-1H-pyridin-2-one;
4-benzyloxy-1-(6-chloro-pyridin-3-ylmethyl)-1H-pyridin-2-one;
4-benzyloxy-1-(3-chloro-benzyl)-1H-pyridin-2-one;
1-benzyl-4-benzyloxy-1H-pyridin-2-one;
1-(4-amino-benzyl)-4-benzyloxy-1H-pyridin-2-one;
1-(2,4-dichloro-benzyl)-4-hydroxy-1H-pyridin-2-one;
3-benzyl-1-(2,4-dichloro-benzyl)-4-hydroxy-1H-pyridin-2-one;
4-(biphenyl-4-ylmethoxy)-1-(2,4-dichloro-benzyl)-1H-pyridin-2-one;
1-(2,4-dichloro-benzyl)-4-(2,4-dichloro-benzyloxy)-1H-pyridin-2-one;
4-(2-chloro-benzyloxy)-1-(2,4-dichloro-benzyl)-1H-pyridin-2-one;
1-(2,4-dichloro-benzyl)-4-methoxy-1H-pyridin-2-one;
1-(2,4-dichloro-benzyl)-4-isopropoxy-1H-pyridin-2-one;
4-cyclohexylmethoxy-1-(2,4-dichloro-benzyl)-1H-pyridin-2-one;
1-(2,4-dichloro-benzyl)-4-propoxy-1H-pyridin-2-one;
1-(2,4-dichloro-benzyl)-4-isobutoxy-1H-pyridin-2-one;
4-butoxy-1-(2,4-dichloro-benzyl)-1H-pyridin-2-one;
1-(2,4-dichloro-benzyl)-4-octyloxy-1H-pyridin-2-one;
1-(2,4-dichloro-benzyl)-4-(4-methyl-pentoxy)-1H-pyridin-2-one;
4-(but-3-enyloxy)-1-(2,4-dichloro-benzyl)-1H-pyridin-2-one;
1-(2,4-dichloro-benzyl)-4-pentyloxy-1H-pyridin-2-one;
[1-(2,4-dichloro-benzyl)-2-oxo-1,2-dihydro-pyridin-4-yloxy]-acetic acid ethylester;
1-(2,4-dichloro-benzyl)-4-(3-methyl-butoxy)-1H-pyridin-2-one;
1-benzyl-4-pentyloxy-1H-pyridin-2-one;
1-(2-chloro-benzyl)-4-pentyloxy-1H-pyridin-2-one;
4-pentyloxy-1-propyl-1H-pyridin-2-one;
1-butyl-4-pentyloxy-1H-pyridin-2-one;
1-isobutyl-4-pentyloxy-1H-pyridin-2-one;
1-(3-methyl-butyl)-4-pentyloxy-1H-pyridin-2-one;
1-(2,4-dichloro-benzyl)-4-hexyloxy-1H-pyridin-2-one;
1-(2,4-dichloro-benzyl)-4-heptyloxy-1H-pyridin-2-one;
1-(4-chloro-benzyl)-4-pentyloxy-1H-pyridin-2-one;
4-aryloxy-1-(2,4-dichloro-benzyl)-1H-pyridin-2-one;
1-(2,4-dichloro-benzyl)-4-(3-methoxy-propoxy)-1H-pyridin-2-one;
1-(2,4-dichloro-benzyl)-4-(3-ethylamino-propoxy)-1H-pyridin-2-one;
1-(2,4-dichloro-benzyl)-4-(2-ethoxy-ethoxy)-1H-pyridin-2-one;
1-(3-methyl-but-2-enyl)-4-pentyloxy-1H-pyridin-2-one;
4-pentyloxy-1-thiazol-4-ylmethyl-1H-pyridin-2-one;
4-pentyloxy-1-pyridin-3-ylmethyl-1H-pyridin-2-one;
1-(2,4-dichloro-benzyl)-4-(4-methyl-pent-3-enyloxy)-1H-pyridin-2-one;
1-(2,4-dichloro-benzyl)-4-(3-methoxy-propoxy)-1H-pyridin-2-one;
1-(2,4-dichloro-benzyl)-4-phenetyloxy-1H-pyridin-2-one;
1-(2-methyl-benzyl)-4-pentyloxy-1H-pyridin-2-one;
4-pentyl-1-phenetyl-1H-pyridin-2-one;
1-(2,4-dichloro-5-fluoro-benzyl)-4-pentyloxy-1H-pyridin-2-one;
1-(3,4-dichloro-benzyl)-4-pentyloxy-1H-pyridin-2-one;
1-(3,4-difluoro-benzyl)-4-pentyloxy-1H-pyridin-2-one;
4-(4-benzyloxy-butoxy)-1-(2,4-dichloro-benzyl)-1H-pyridin-2-one;
1-(2,4-dichloro-benzyl)-4-(4-hydroxy-butoxy)-1H-pyridin-2-one;
4-(5-benzyloxy-pentyloxy)-1-(2,4-dichloro-benzyl)-1H-pyridin-2-one;
1-(2,4-dichloro-benzyl)-4-(5-hydroxy-pentyloxy)-1H-pyridin-2-one;
1-(6-chloro-benzo[1,3]dioxol-5-ylmethyl)-4-pentyloxy-1H-pyridin-2-one;
1-(2,4-dichloro-benzyl)-4-(2-methyl-benzyloxy)-1H-pyridin-2-one;
1-(2,4-dichloro-benzyl)-4-(4-methyl-benzyloxy)-1H-pyridin-2-one;
1-(2-nitro-benzyl)-4-pentyloxy-1H-pyridin-2-one;
1-(2-amino-benzyl)-4-pentyloxy-1H-pyridin-2-one;
N-[2-(2-oxo-4-pentyloxy-2H-pyridin-1-ylmethyl)-phenyl]-acetamide;
4-pentyloxy-1-(2-trifluoromethyl-benzyl)-1H-pyridin-2-one;
N-[4-(4-benzyloxy-2-oxo-2H-pyridin-1-ylmethyl)-phenyl]acetamide;
1-(2,4-dichloro-benzyl)-4-(naphthalen-2-ylmethoxy)-1H-pyridin-2-one;
1-naphthalen-2-ylmethyl-4-pentyloxy-1H-pyridin-2-one;
4-benzyloxy-1-(6-chloro-benzo[1,3]dioxol-5-ylmethyl)-1H-pyridin-2-one;

1-(6-chloro-benzo[1,3]dioxol-5-ylmethyl)-4-(3-methyl-butoxy)-1H-pyridin-2-one;
1-(2-methyl-benzyl)-4-(3-methyl-butoxy)-1H-pyridin-2-one;
4-(3-methyl-butoxy)-1-(2-nitro-benzyl)-1H-pyridin-2-one;
1-(2,4-dichloro-benzyl)-4-pentylamino-1H-pyridin-2-one;
1-(2,3-dichloro-benzyl)-4-pentyloxy-1H-pyridin-2-one;
1-(2-methoxy-benzyl)-4-pentyloxy-1H-pyridin-2-one;
1-(2,3-dimethoxy-benzyl)-4-pentyloxy-1H-pyridin-2-one;
4-(5-benzyloxy-pentyloxy)-1-(6-chloro-benzo[1,3]dioxol-5-ylmethyl)-1H-pyridin-2-one;
1-(2-chloro-benzyl)-4-(3-methyl-butoxy)-1H-pyridin-2-one;
1-(3,4-dichloro-benzyl)-4-(3-methyl-butoxy)-1H-pyridin-2-one;
1-(2,4-dichloro-5-fluoro-benzyl)-4-(3-methyl-butoxy)-1H-pyridin-2-one;
1-benzyl-4-(3-methyl-butoxy)-1H-pyridin-2-one;
1-(4-chloro-benzyl)-4-(3-methyl-butoxy)-1H-pyridin-2-one;
1-(2,4-dichloro-benzyl)-4-pentyloxy-1H-pyrimidin-2-one;
1-(2,4-dichloro-benzyl)-4-(4-methyl-pentyloxy)-1H-pyrimidin-2-one;
1-(2,4-dichloro-benzyl)-4-phenoxy-1H-pyrimidin-2-one;
4-(butyl-methyl-amino)-1-(2,4-dichloro-benzyl)-1H-pyrimidin-2-one;
1-(2,4-dichloro-benzyl)-4-(2-diethylamino-ethoxy)-1H-pyrimidin-2-one;
4-butoxy-1-(2,4-dichloro-benzyl)-1H-pyrimidin-2-one;
1-(2,6-dichloro-benzyl)-4-pentyloxy-1H-pyridin-2-one;
1-(2-chloro-6-fluoro-benzyl)-4-pentyloxy-1H-pyridin-2-one;
1-(2-methyl-3-nitro-benzyl)-4-pentyloxy-1H-pyridin-2-one;
1-(3-amino-2-methyl-benzyl)-4-pentyloxy-1H-pyridin-2-one;
1-(4-methoxy-3,5-dimethyl-pyridin-2-ylmethyl)-4-pentyloxy-1H-pyridin-2-one;
1-(6-chloro-benzo[1,3]dioxol-5-ylmethyl)-4-(5-hydroxy-pentyloxy)-1H-pyridin-2-one;
1-(2-methoxy-5-nitro-benzyl)-4-pentyloxy-1H-pyridin-2-one;
1-(5-amino-2-methoxy-benzyl)-4-pentyloxy-1H-pyridin-2-one;
1-(2-ethyl-benzyl)-4-pentyloxy-1H-pyridin-2-one;
1-(2-chloro-5-nitro-benzyl)-4-pentyloxy-1H-pyridin-2-one;
1-(5-amino-2-chloro-benzyl)-4-pentyloxy-1H-pyridin-2-one;
1-(4-methoxy-2,3-dimethyl-benzyl)-4-pentyloxy-1H-pyridin-2-one;
1-(2-methyl-pyridin-3-ylmethyl)-4-pentyloxy-1H-pyridin-2-one;
N-[4-chloro-3-(2-oxo-4-pentyloxy-2H-pyridin-1-ylmethyl)-phenyl]-acetamide;
1-(2,4-dichloro-benzyl)-4-(3-dimethylamino-propoxy)-1H-pyridin-2-one;
1-(2,4-dichloro-benzyl)-4-(4-dimethylamino-butoxy)-1H-pyridin-2-one;
1-(2,4-dichloro-benzyl)-4-(6-dimethylamino-hexyloxy)-1H-pyrimidin-2-one;
1-(2,4-dimethyl-benzyl)-4-pentyloxy-1H-pyridin-2-one;
1-(2-chloro-5-trifluoromethyl-benzyl)-4-pentyloxy-1H-pyridin-2-one;
1-(2-hydroxy-benzyl)-4-pentyloxy-1H-pyridin-2-one;
4-(3-cyclo-propoxy)-1-(2,4-dichloro-benzyl)-1H-pyrimidin-2-one;
1-(2,4-dichloro-benzyl)-4-(3-methyl-pentyloxy)-1H-pyrimidin-2-one;
1-(2,4-dichloro-benzyl)-4-hex-4-enyloxy-1H-pyrimidin-2-one;
4-(2-cyclopropyl-ethoxy)-1-(2,4-dichloro-benzyl)-1H-pyrimidin-2-one;
1-(2,4-dichloro-benzyl)-4-(3-methyl-pentyloxy)-1H-pyridin-2-one;
1-(2,4-dichloro-benzyl)-4-(5-morpholin-4-yl-pentyloxy)-1H-pyridin-2-one;
1-(2-chloro-5-methoxy-benzyl)-4-pentyloxy-1H-pyridin-2-one;
1-(2-chloro-5-ethoxy-benzyl)-4-pentyloxy-1H-pyridin-2-one;
1-(2-chloro-5-propoxy-benzyl)-4-pentyloxy-1H-pyridin-2-one;
1-[2-chloro-5-(2-hydroxy-ethoxy)-benzyl]-4-pentyloxy-1H-pyridin-2-one;
[4-chloro-3-(2-oxo-4-pentyloxy-2H-pyridin-1-ylmethyl)-oxy]-acetonitrile;
1-[5-(2-amino-ethoxy)-2-chloro-benzyl]-4-pentyloxy-1H-pyridin-2-one;
N-[2-methyl-3-(2-oxo-4-pentyloxy-2H-pyridin-1-ylmethyl)-phenyl]-acetamide;
1-(2-methyl-3-methylamino-benzyl)-4-phenyloxy-1H-pyridin-2-one;
1-(3-dimethylamino-2-methyl-benzyl)-4-phenyloxy-1H-pyridin-2-one;
1-(3-ethylamino-2-methyl-benzyl)-4-pentyloxy-1H-pyridin-2-one;
1-(3-diethylamino-2-methyl-benzyl)-4-pentyloxy-1H-pyridin-2-one;
1-(2-methyl-3-propylamino-benzyl)-4-pentyloxy-1H-pyridin-2-one;
1-(3-dipropylamino-2-methyl-benzyl)-4-pentyloxy-1H-pyridin-2-one;
1-[3-(2-hydroxy-ethylamino)-2-methyl-benzyl]-4-pentyloxy-1H-pyridin-2-one;
1-(2-chloro-5-methoxy-4-nitro-benzyl)-4-pentyloxy-1H-pyridin-2-one;
1-(4-amino-2-chloro-5-methoxy-benzyl)-4-pentyloxy-1H-pyridin-2-one;
N-[5-chloro-2-methoxy-4-(2-oxo-4-pentyloxy-2H-pyridin-1-ylmethyl)-phenyl]-acetamide;
1-(2-chloro-5-methoxy-4-methylamino-benzyl)-4-pentyloxy-1H-pyridin-2-one;
1-(2-chloro-4-dimethylamino-5-methoxy-benzyl)-4-pentyloxy-1H-pyridin-2-one;
1-(2-chloro-4-ethylamino-5-methoxy-benzyl)-4-pentyloxy-1H-pyridin-2-one;
1-(2-chloro-5-methoxy-4-propylamino-benzyl)-4-pentyloxy-1H-pyridin-2-one;
1-[2-chloro-4-(2-hydroxy-ethylamino)-5-methoxy-benzyl]-4-pentyloxy-1H-pyridin-2-one;
1-(4-amino-6-chloro-3-methoxy-2-nitro-benzyl)-4-pentyloxy-1H-pyridin-2-one;
1-(2,4-diamino-6-chloro-3-methoxy-benzyl)-4-pentyloxy-1H-pyridin-2-one;
1-(2,5-dichloro-6-methoxy-pyrimidin-4-ylmethyl)-4-pentyloxy-1H-pyridin-2-one;
1-(2,4-dichloro-benzenesulfonyl)-4-pentyloxy-1H-pyridin-2-one;
1-(4-methanesulfonyl-benzyl)-4-pentyloxy-1H-pyridin-2-one;
1-(4-amino-2-chloro-5-hydroxy-benzyl)-4-pentyloxy-1H-pyridin-2-one;
4-(4-bromo-butoxy)-1-(2,4-dichloro-benzyl)-1H-pyridin-2-one;

4-[1-(2,4-dichloro-benzyl)-2-oxo-1,2-dihydro-pyridin-4-yloxy]-butylammonium;
1-(5-chloro-2,6-dimethoxy-pyrimidin-4-ylmethyl)-4-pentyloxy-1H-pyridin-2-one;
1-(2-amino-5-chloro-6-methoxy-pyrimidin-4-ylmethyl)-4-pentyloxy-1H-pyridin-2-one;
1-(6-amino-2,5-dichloro-pyrimidin-4-ylmethyl)-4-pentyloxy-1H-pyridin-2-one;
5-chloro-6-(2-oxo-4-pentyloxy-2H-pyridin-1-ylmethyl)-3H-benzoxazol-2-one;
1-(2-chloro-4-hydroxy-benzyl)-4-pentyloxy-1H-pyridin-2-one;
1-(2-chloro-4-isopropoxy-benzyl)-4-pentyloxy-1H-pyridin-2-one;
2-[3-(2-oxo-4-pentyloxy-2H-pyridin-1-yl)-propyl]-isoindole-1,3-dione;
1-(3-amino-propyl)-4-pentyloxy-1H-pyridin-2-one;
N-[3-(2-oxo-4-pentyloxy-2H-pyridin-1-yl)-propyl]-acetamide;
1-(3-dimethylamino-propyl)-4-pentyloxy-1H-pyridin-2-one;
1-(2,4-dichloro-benzyl)-6-methyl-4-pentyloxy-1H-pyridin-2-one;
1-(2,4-dichloro-benzyl)-6-methyl-3-pentyl-4-pentyloxy-1H-pyridin-2-one;
1-(2-amino-ethyl)-4-pentyloxy-1H-pyridin-2-one;
N-[2-(2-oxo-4-pentyloxy-2H-pyridin-1-yl)-ethyl]-acetamide;
N-[1,1-dimethyl-2-(2-oxo-4-pentyloxy-2H-pyridin-1-yl)-ethyl]-methanesulfonamide;
N-[1-(2-oxo-4-pentyloxy-2H-pyridin-1-ylmethyl)-propyl]-methanesulfonamide;
1-(7-nitro-benzo[1,3]dioxol-5-ylmethyl)-4-pentyloxy-1H-pyridin-2-one;
1-(2-chloro-3-nitro-benzyl)-4-pentyloxy-1H-pyridin-2-one;
1-(3-amino-2-chloro-benzyl)-4-pentyloxy-1H-pyridin-2-one;
N-[2-chloro-3-(2-oxo-4-pentyloxy-2H-pyridin-1-ylmethyl)-phenyl]-acetamide;
N-[2-chloro-3-(2-oxo-4-pentyloxy-2H-pyridin-1-ylmethyl)-phenyl]-methanesulfonamide;
N,N'-[2-chloro-3-(2-oxo-4-pentyloxy-2H-pyridin-1-ylmethyl)-phenyl]dimethanesulfonamide;
1-[2-chloro-3-(2-hydroxy-ethylamino)-benzyl]-4-pentyloxy-1H-pyridin-2-one;
4-chloro-2-(2-chloro-benzyl)-5-pentyloxy-2H-pyridazin-3-one;
2-(2-chloro-benzyl)-5-pentyloxy-2H-pyridazin-3-one;
1-(3-amino-2,6-dichloro-benzyl)-4-pentyloxy-1H-pyridin-2-one;
1-(3-benzyloxy-2-chloro-4-methoxy-benzyl)-4-pentyloxy-1H-pyridin-2-one;
1-(2-chloro-3,4-dimethoxy-benzyl)-4-pentyloxy-1H-pyridin-2-one;
1-(2-chloro-3-hydroxy-4-methoxy-benzyl)-4-pentyloxy-1H-pyridin-2-one;
1-[2-chloro-4-methoxy-3-(2-methoxy-ethoxy)-benzyl]-4-pentyloxy-1H-pyridin-2-one;
1-[2-chloro-4-methoxy-3-(2-pyrrolidin-1-yl-ethoxy)-benzyl]-4-pentyloxy-1H-pyridin-2-one;
1-[2-chloro-3-(2-dimethylamino-ethoxy)-4-methoxy-benzyl]-4-pentyloxy-1H-pyridin-2-one;
2-{3-[2-chloro-6-methoxy-3-(2-oxo-4-pentyloxy-2H-pyridin-1-ylmethyl)-phenoxy]-propyl}-isoindole-1,3-dione;
1-[3-(2-dimethylamino-ethoxy)-2-methyl-benzyl]-4-pentyloxy-1H-pyridin-2-one;
1-[2-chloro-3-(2-dimethylamino-ethylamino)-benzyl]-4-pentyloxy-1H-pyridin-2-one;
1-[2,6-dichloro-3-(2-hydroxy-ethylamino)-benzyl]-4-pentyloxy-1H-pyridin-2-one;
1-[2,6-dichloro-3-(2-dimethylamino-ethylamino)-benzyl]-4-pentyloxy-1H-pyridin-2-one;
1-[2,6-dichloro-3-(3-hydroxy-propylamino)-benzyl]-4-pentyloxy-1H-pyridin-2-one;
1-[2,6-dichloro-3-(3-dimethylamino-propylamino)-benzyl]-4-pentyloxy-1H-pyridin-2-one;
1-[3-(3-amino-propylamino)-2,6-dichloro-benzyl]-4-pentyloxy-1H-pyridin-2-one;
1-(3-fluoro-2-methyl-benzyl)-4-pentyloxy-1H-pyridin-2-one;
1-(2-chloro-3-dimethylaminomethyl-4-fluoro-benzyl)-4-pentyloxy-1H-pyridin-2-one;
1-(2,6-dichloro-3-methylamino-benzyl)-4-pentyloxy-1H-pyridin-2-one;
1-(2,6-dichloro-3-dimethylamino-benzyl)-4-pentyloxy-1H-pyridin-2-one;
[2-chloro-3-(2-oxo-4-pentyloxy-2H-pyridin-1-ylmethyl)-phenylamino]-acetic acid;
1-(6-chloro-benzo[1,3]dioxol-5-ylmethyl)-4-(pyridin-4-yl-methoxy)-1H-pyridin-2-one;
1-(6-chloro-benzo[1,3]dioxol-5-ylmethyl)-4-(6-chloro-pyridin-3-ylmethoxy)-1H-pyridin-2-one;
1-(6-chloro-benzo[1,3]dioxol-5-ylmethyl)-4-(4-methoxy-3,5-dimethylpyridin-2-ylmethoxy)-1H-pyridin-2-one;
1-(6-chloro-benzo[1,3]dioxol-5-ylmethyl)-4-(2-methyl-pyridin-3-ylmethoxy)-1H-pyridin-2-one;
1-(6-chloro-benzo[1,3]dioxol-5-ylmethyl)-4-(thiazol-4-yl-methoxy)-1H-pyridin-2-one;
1-(6-chloro-benzo[1,3]dioxol-5-ylmethyl)-4-(pyridin-2-yl-methoxy)-1H-pyridin-2-one;
pentanoic acid 1-(6-chloro-benzo[1,3]dioxol-5-ylmethyl)-2-oxo-1,2-dihydro-pyridin-4-yl ester;
hexanoic acid 1-(6-chloro-benzo[1,3]dioxol-5-ylmethyl)-2-oxo-1,2-dihydro-pyridin-4-yl ester;
1-(2-chloro-3-trifluoromethyl-benzyl)-4-pentyloxy-1H-pyridin-2-one;
thiophene-2-carboxyl acid 1-(6-chloro-benzo[1,3]dioxol-5-ylmethyl)-2-oxo-1,2-dihydro-pyridin-4-yl ester;
toluene-4-sulfonic acid 1-(6-chloro-benzo[1,3]dioxol-5-yl-methyl)-2-oxo-1,2-dihydro-pyridin-4-yl ester;
1-(6-chloro-benzo[1,3]dioxol-5-ylmethyl)-4-(4,4,5,5,5-pentafluoro-pentyloxy)-1H-pyridin-2-one;
1-(6-chloro-benzo[1,3]dioxol-5-ylmethyl)-4-(2-dimethylamino-ethoxy)-1H-pyridin-2-one;
1-(2,4-dichloro-benzyl)-4-(5-fluoro-pentyloxy)-1H-pyridin-2-one;
3-[1-(2,4-dichloro-benzyl)-2-oxo-1,2-dihydro-pyridin-4-yloxymethyl]-indole-1-carboxyl acid tetra-butyl ester;
1-(2,4-dichloro-benzyl)-4-(2-thiophen-2-yl-ethoxy)-1H-pyridin-2-one;
1-(2,4-dichloro-benzyl)-4-(2-thiophen-3-yl-ethoxy)-1H-pyridin-2-one;
1-(2,4-dichloro-benzyl)-4-(2-pyrrol-1-yl-ethoxy)-1H-pyridin-2-one;
1-(2,4-dichloro-benzyl)-4-(3-pyrrol-1-yl-propoxy)-1H-pyridin-2-one;
1-(3-amino-2-methyl-benzyl)-4-(2-thiophen-2-yl-ethoxy)-1H-pyridin-2-one;
1-(3-amino-2-methyl-benzyl)-4-(2-pyrrol-1-yl-ethoxy)-1H-pyridin-2-one;
1-(3-amino-2-methyl-benzyl)-4-[2-(4-methyl-thiazol-5-yl)-ethoxy]-1H-pyridin-2-one;

1-(3-amino-2-methyl-benzyl)-4-(2-(5-bromothiophen-2-yl)-ethoxy)-1H-pyridin-2-one;
1-(3-amino-2-methyl-benzyl)-4-(2-(5-fluorothiophen-2-yl)-ethoxy)-1H-pyridin-2-one;
1-[3-(2-hydroxy-ethylamino)-2-methyl-benzyl]-4-(2-thiophen-2-yl-ethoxy)-1H-pyridin-2-one;
2-{2-methyl-3-[2-oxo-4-(2-thiophene-2-yl -ethoxy)-2H-pyridin-1-ylmethyl]-phenylamino}-acetamide;
1-[3-(cyclopropylmethyl-amino)-2-methyl-benzyl]-4-(2-thiophen-2-yl-ethoxy)-1H-pyridin-2-one;
N-{2-methyl-3-[2-oxo-4-(2-thiophen-2-yl-ethoxy)-2H-pyridin-1-ylmethyl]-phenylamino}-acetonitrile;
N-(2-{2-methyl-3-[2-oxo-4-(2-thiophen-2-yl-ethoxy)-2H-pyridin-1-ylmethyl]-phenylamino}-ethyl)-acetamide;
1-[2-methyl-3-(2-pyrrol-1-yl-ethylamino)-benzyl]-4-(2-thiophen-2-yl-ethoxy)-1H-pyridin-2-one;
1-[2-methyl-3-(2-oxo-2-pyrrolidin-1-yl-ethylamino)-benzyl]-4-(2-thiophen-2-yl-ethoxy)-1H-pyridin-2-one;
1-[2-methyl-3-(2-oxo-2-piperidin-1-yl-ethylamino)-benzyl]-4-(2-thiophen-2-yl-ethoxy)-1H-pyridin-2-one;
N,N-dimethyl-2-{2-methyl-3-[2-oxo-4-(2-thiophen-2-yl-ethoxy)-2H-pyridin-1-ylmethyl]-phenylamino}-acetamide;
1-{2-methyl-3-[2-(4-methyl-piperazin-1-yl)-2-oxo-ethylamino]-benzyl}-4-(2-thiophen-2-yl-ethoxy)-1H-pyridin-2-one;
1-[2-methyl-3-(2-morpholin-4-yl-2-oxo-ethylamino)-benzyl]-4-(2-thiophen-2-yl-ethoxy)-1H-pyridin-2-one;
1-(3-amino-2-methyl-benzyl)-4-(2-furan-2-yl-ethoxy)-1H-pyridin-2-one;
1-(3-amino-2-methyl-benzyl)-4-[2-(5-methyl-thiophen-2-yl)-ethoxy]-1H-pyridin-2-one;
1-(3-amino-2-methyl-benzyl)-4-[2-(5-chloro-thiophen-2-yl)-ethoxy]-1H-pyridin-2-one;
1-(2,4-dichloro-benzyl)-4-[2-(3-methyl-thiophen-2-yl)-ethoxy]-1H-pyridin-2-one;
1-(3-amino-2-methyl-benzyl)-4-(2-benzo[b]thiophen-3-yl-ethoxy)-1H-pyridin-2-one;
1-(3-amino-2-methyl-benzyl)-4-[2-(5-chloro-3-methyl-benzo[b]thiophen-2-yl)-ethoxy]-1H-pyridin-2-one;
1-(3-amino-2-methyl-benzyl)-4-[2-(3-methyl-benzo[b]thiophen-2-yl)-ethoxy]-1H-pyridin-2-one;
1-(3-amino-2-methyl-benzyl)-4-[2-(5-methyl-furan-2-yl)-ethoxy]-1H-pyridin-2-one;
1-(3-amino-2-methyl-benzyl)-4-[2-(5-ethyl-furan-2-yl)-ethoxy]-1H-pyridin-2-one;
5-[1-(3-amino-2-methyl-benzyl)-2-oxo-1,2-dihydro-pyridin-4-yloxymethyl]-furan-2-carboxylic acid ethyl ester;
1-[3-(2-dimethylamino-ethylamino)-2-methyl-benzyl]-4-(2-thiophen-2-yl-ethoxy)-1H-pyridin-2-one;
1-(3-amino-2-methyl-benzyl)-4-[2-(5-methylsulfanyl-thiophen-2-yl)-ethoxy]-1H-pyridin-2-one;
1-(3-amino-2-methyl-benzyl)-4-(2-benzofuran-2-yl-ethoxy)-1H-pyridin-2-one;
1-(3-amino-2-methyl-benzyl)-4-[2-(3-methyl-isoxazol-5-yl)-ethoxy]-1H-pyridin-2-one;
1-(3-amino-2-methyl-benzyl)-4-[2-(4,5-dimethyl-thiophen-2-yl)-ethoxy]-1H-pyridin-2-one;
1-(3-amino-2-methyl-benzyl)-4-[2-(5-ethyl-thiophen-2-yl)-ethoxy]-1H-pyridin-2-one;
1-(3-amino-2,6-dichloro-benzyl)-4-(2-thiophen-2-yl-ethoxy)-1H-pyridin-2-one;
N-{2-methyl-3-[2-oxo-4-(2-thiophen-2-yl-ethoxy)-2H-pyridin-1-ylmethyl]-phenyl}-acetamide;
1-[2-methyl-3-(2-piperidin-1-yl-ethylamino)-benzyl]-4-(2-thiophen-2-yl-ethoxy)-1H-pyridin-2-one;
1-[2-methyl-3-(2-morpholin-4-yl-ethylamino)-benzyl]-4-(2-thiophen-2-yl-ethoxy)-1H-pyridin-2-one;
N-{2-methyl-3-[2-oxo-4-(2-thiophen-2-yl-ethoxy)-2H-pyridin-1-ylmethyl]-phenyl}-methanesulfonamide;
1-(3-amino-2-methyl-benzyl)-4-[2-(4-bromo-thiophen-2-yl)-ethoxy]-1H-pyridin-2-one;
1-(6-chloro-benzo[1,3]dioxol-5-ylmethyl)-4-(2-pyrrol-1-yl-ethoxy)-1H-pyridin-2-one;
1-(6-chloro-benzo[1,3]dioxol-5-ylmethyl)-4-(2-thiophen-2-yl-ethoxy)-1H-pyridin-2-one;
1-[2-methyl-3-(2-pyrrolidin-1-yl-ethylamino)-benzyl]-4-(2-thiophen-2-yl-ethoxy)-1H-pyridin-2-one;
N-(2-{2-methyl-3-[2-oxo-4-(2-thiophen-2-yl-ethoxy)-2H-pyridin-1-ylmethyl]-phenylamino}-ethyl)-acetamide;
1-{2-methyl-3-[(pyridin-3-ylmethyl)-amino]-benzyl}-4-(2-thiophen-2-yl-ethoxy)-1H-pyridin-2-one;
2-methyl-3-[2-oxo-4-(2-thiophen-2-yl-ethoxy)-2H-pyridin-1-ylmethyl]-phenyl ester;
1-{2-methyl-3-[(pyridin-4-ylmethyl)-amino]-benzyl}-4-(2-thiophen-2-yl-ethoxy)-1H-pyridin-2-one;
1-{2-methyl-3-[(thiazol-4-ylmethyl)-amino]-benzyl}-4-(2-thiophen-2-yl-ethoxy)-1H-pyridin-2-one;
1-[3-(4-methoxy-benzyloxy)-2-methyl-benzyl]-4-(2-thiophen-2-yl-ethoxy)-1H-pyridin-2-one;
1-{3-[(3,5-dimethyl-isoxazol-4-ylmethyl)-amino]-2-methyl-benzyl}-4-(2-thiophen-2-yl-ethoxy)-1H-pyridin-2-one;
1-(3-hydroxy-2-methyl-benzyl)-4-(2-thiophen-2-yl-ethoxy)-1H-pyridin-2-one;
1-{2-methyl-3-[(1-methyl-pyrrolidin-2-ylmethyl)-amino]-benzyl}-4-(2-thiophen-2-yl-ethoxy)-1H-pyridin-2-one;
1-{2-methyl-3-[2-(1-methyl-pyrrolidin-2-yl)-ethylamino]-benzyl}-4-(2-thiophen-2-yl-ethoxy)-1H-pyridin-2-one;
(2-{2-methyl-3-[2-oxo-4-(2-thiophen-2-yl-ethoxy)-2H-pyridin-1-ylmethyl]-phenylamino}-ethyl)-phosphonic acid diethyl ester;
4-(isobutylthio)-1-(2-methyl-3-nitrobenzyl)pyridine-2(1H)-one;
1-(3-amino-2-methylbenzyl)-4-(isobutylthio)pyridine-2(1H)-one;
1-(3-amino-2-methylbenzyl)-4-(furan-2-ylmethylthio)pyridine-2(1H)-one;
1-(3-amino-2-methylbenzyl)-4-(pentylthio)pyridine-2-(1H)-one;
1-(3-amino-2-methylbenzyl)-4-(phenethylthio)pyridine-2(1H)-one;
1-(3-amino-2-methylbenzyl)-4-(butylthio)pyridine-2(1H)-one;
1-(3-amino-2-methylbenzyl)-4-(thiophen-2-ylmethylthio)pyridine-2(1H)-one;
1-(3-amino-2-methylbenzyl)-4-(pentylthio)pyridine-2(1H)-one;
1-(3-amino-2-methylbenzyl)-4-(propylthio)pyridine-2(1H)-one;
1-(3-amino-2-methylbenzyl)-4-(1-methylbutylthio)pyridine-2 (1H)-one;
N,N-dimethyl-3-(2-methyl-3-((2-oxo-4-(2-(thiophen-2-yl)ethoxy)pyridin-1(2H)-yl)methyl)phenylamino)propane-1-sulfonamide;
1-(3-amino-2-methylbenzyl)-4-(2-(thiophene-2-yl)ethylamino)pyridine-2-(1H)-one.

The compound of formula (I) or (II) may be prepared by simple alkylation or arylation using pyridazine derivative, pyrimidinone derivative, triazinone derivative or pyridone derivative.

A preferred example of the compound of formula (I) is a pyridone compound which may be prepared as shown in Reaction Scheme 1 or 2. As used herein, NaH is sodium hydride, TsCl is p-toluenesulfonyl chloride, Ac$_2$O is acetic anhydride, BuOH is butanol, t-BuOH is t-butanol, Pd/C is palladium on carbon, KOtBu is potassium t-butoxide, and Zn is zinc dust.

Reaction Scheme 1

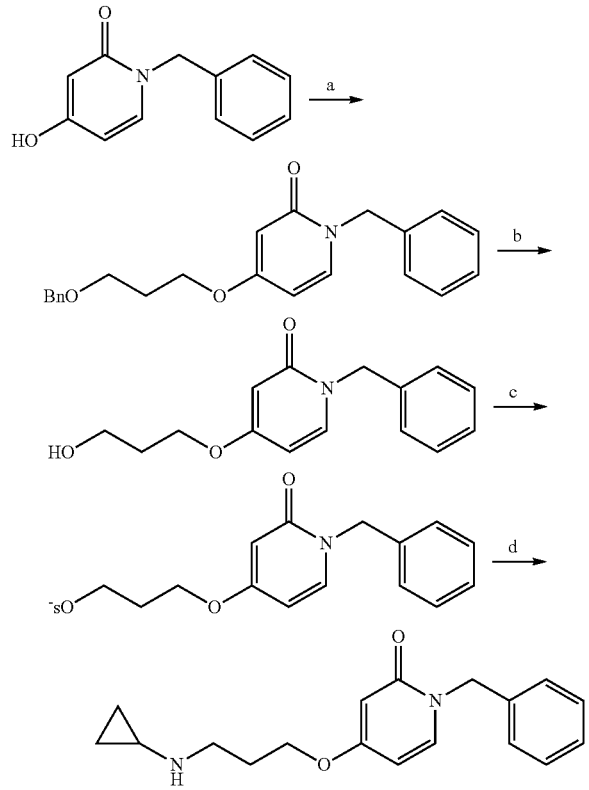

Reagents: (a) NaH, benzyloxypropyl bromide, DMF; (b) Pd/C, H$_2$, MeOH; (c) TsCl, TEA, DCM; (d) cyclopropylamine, MeOH Reaction Scheme 2

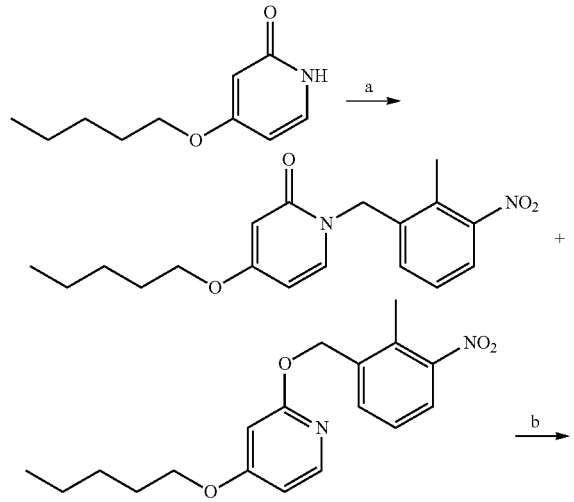

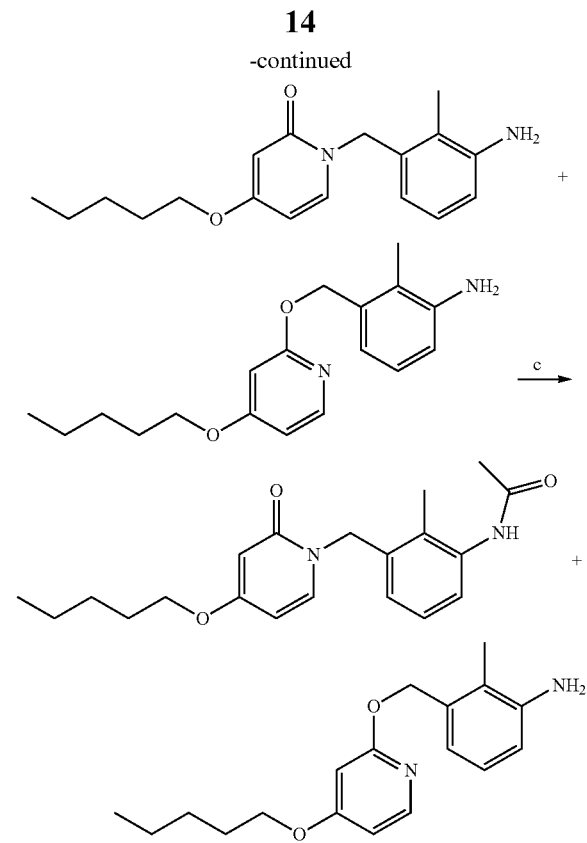

Reagents: (a) NaH, 2-methyl-3-nitrobenzyl chloride, DMF; (b) hydrazine, Zn, EtOH; (c) Acetic anhydride, TEA, DCM The pyridone derivatives used as starting materials above may be prepared as shown in Reaction Scheme 3 or 4, respectively.

Reaction Scheme 3

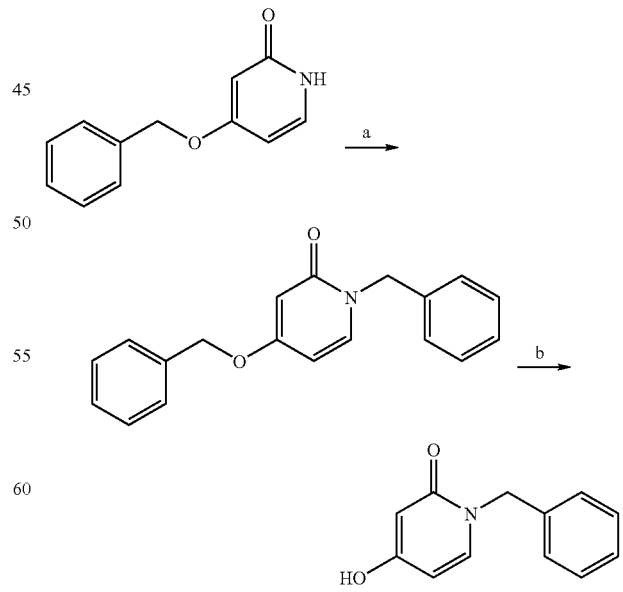

Reagents: (a) BnCl, NaH, DMF; (b) Pd/C, H$_2$, MeOH

Reaction Scheme 4

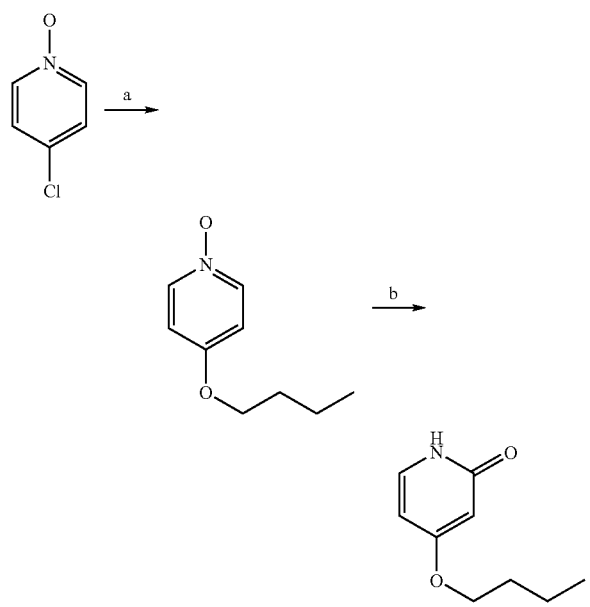

Reagents: (a) BuOH, KOtBu t-BuOH; (b) Ac₂O, reflux

Another preferred example of the compound of formula (I) is a pyridone compound being substituted with a methyl group, which may be prepared as shown in Reaction Scheme 5.

Reaction Scheme 5

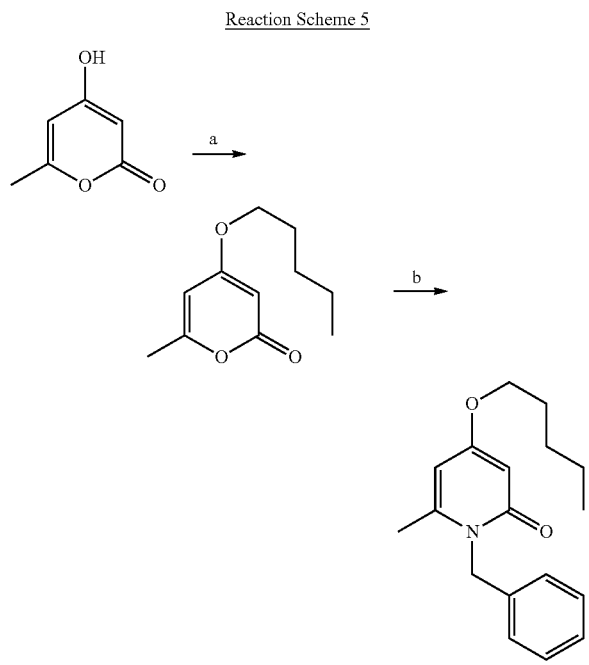

Reagents: (a) NaH, pentyl bromide, DMF; (b) benzyl amine, EtOH, reflux

Still another preferred example of the compound of formula is a pyridazine compound, which may be prepared as shown in Reaction Scheme 6.

Reaction Scheme 6

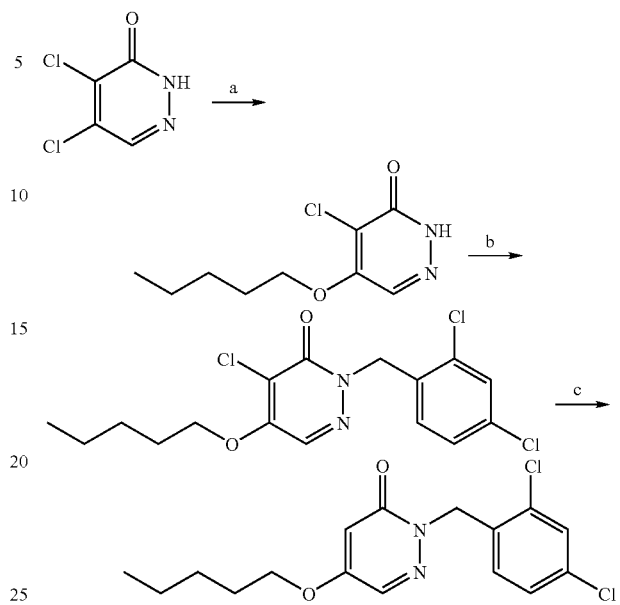

Reagents: (a) NaH, pentanol, DMF; (b) 2,4-dichlorobenzyl chloride, NaH, DMF; (c) pd/C, H₂, MeOH Substituting 4-methylpentanol for pentanol in Reaction Scheme 6 will produce 2, (2,4-dichlorobenzyl)-5-4-methylpentyloxy)pyridazin-3(2H)-one:

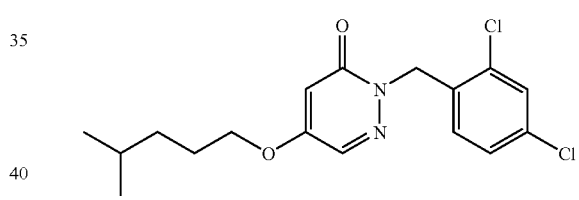

2-(2,4-dichlorobenzyl)-5-4-methylpentyloxy)pyridazin-3(2H)-one

The compound of formula (I) or (II) effectively inhibits the activity of Fab I. Accordingly, the present invention provides a method for inhibiting the activity of Fab I, comprising bringing a body fluid such as blood, urine and lymph into contact with the compound of formula (I) or (II).

The present invention also provides a pharmaceutical composition comprising the compound of formula (I) or (II) as an active ingredient in an amount effective to treat or prevent bacteria-related diseases.

The inventive pharmaceutical composition may comprise pharmaceutically acceptable carriers, diluents, adjuvants or vehicles. Exemplary carriers, diluents, adjuvants and vehicles include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride or zinc salts, colloidal silica, magnesium trisilicate, polyvinyl pyrrolidone, cellulose-based substances, polyethylene glycol, sodium carboxy methylcellulose, polyacrylates, waxes, polyethylene-polyoxypropylene-block polymers, polyethylene glycol, wool fat, parabens, chlorobutanol, phenol, sorbic acid, aluminum monostearate, gelatin and the like. It may also be desirable to include isotonic agents, for example sugars, sodium chloride, and the like.

Various formulations of the present invention may be prepared using surfactants such as TWEENs™ or SPANs™, emulsifying agents, extenders, etc., and may be administered orally, sublingually, parenterally, by inhalation spray, topically, rectally, nasally, buccally, vaginally or via an implanted reservoir The term "parenteral" as used herein includes subcutaneous, intravenous, intramuscular, intra-articular, intrasynovial, intrasternal, intrathecal, intrahepatic, intralesional and intracranial injection or infusion techniques. Preferably, the composition is administered orally, intraperitoneally, subcutaneously, intramuscularly or intravenously.

Sterile injectable formulations may be in the form of aqueous or oleaginous suspensions. These suspensions may be formulated by a conventional method using suitable dispersing or wetting agents and suspending agents such as water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

Formulations suitable for oral administration may be in the form of capsules, tablets, pills, powders, or granules. In such solid dosage forms, the active compound can be admixed with at least one inert carrier such as sodium citrate or dicalcium phosphate; or with fillers, extenders, binders, humectants, disintegrating agents such as calcium carbonate or certain complex silicates, solution retarders such as paraffin, absorption accelerators such as quaternary ammonium compounds, wetting agents such as cetyl alcohol or glycerol monostearate, adsorbents, and lubricants such as magnesium stearate, solid polyethylene glycols, and the like, or mixtures thereof. In the form of capsules, the active compound can be admixed with buffering agents, and can also be admixed with excipients such as lactose or milk sugar as well as high molecular weight polyethyleneglycols, and the like.

Formulations suitable for oral administration may alternatively be in the form of aqueous suspensions, solutions, syrups, etc. When aqueous suspensions are required for oral use, the active ingredient is combined with emulsifying and suspending agents. If desired, certain sweetening, flavoring or coloring agents may also be added.

Formulations for oral administration can include a coating, and can be formulated with certain agents so as to release the active compound in a particular portion of the digestive tract.

Formulations for topical administration may be useful in that the target of treatment includes areas or organs readily accessible by topical application, e.g., the eye, the skin or the lower intestinal tract. Topically-transdermal patches may also be used for topical administration.

For topical application to the skin or the lower intestinal tract, the compositions may be formulated in the form of ointments, lotions, creams or sprays form containing the active component suspended or dissolved in one or more suitable carriers. The ointments may contain mineral oil, liquid petrolatum, white petrolatum, propylene glycol, polyoxyethylene, polyoxypropylene, emulsifying wax or water as suitable carriers. The lotions, creams or sprays may contain mineral oil, sorbitan monostearate, polysorbate 60, cetyl esters wax, cetearyl alcohol, 2-octyldodecanol, benzyl alcohol or water as suitable carriers.

For ophthalmic use, the compositions may be formulated as micronized suspensions or solutions in isotonic, pH adjusted sterile saline, either with or without a preservative such as benzylalkonium chloride. Alternatively, the compositions may be formulated in ophthalmic ointments such as petrolatum.

Formulations suitable for administration by nasal aerosol or inhalation may be in the form of solutions in saline. The solutions may contain benzyl alcohol or other suitable preservatives, absorption promoters to enhance bioavailability, fluorocarbons, and/or other conventional solubilizing or dispersing agents.

Formulations suitable for rectal or vaginal administration can be prepared by mixing the compounds of the present invention with suitable non-irritating excipients or carriers such as a suppository wax, cocoa butter, or polyethyleneglycol which melt at body temperature.

If necessary, the inventive compound may be used with other antimicrobials such as penicillin or cephalosporin.

A single dose of the compound of formula (I) or (II) may range from about 50 to 1,500 mg, although the dose may be varied depending upon the age, body weight and symptoms of the patient. A typical daily dose of the compound of formula (I) or (II) may range from about 50 to 5,000 mg, or from about 150 to 3,000 mg for adults, and can be from about 50 to 2000 mg, or from about 100 to 2000 mg, or from about 300 to 2500 mg, or from about 500 to 4000 mg, or from about 500 to 5000 mg.

Further, the present invention provides a method for treating bacteria-related diseases, comprising administering an effective amount of a compound of formula (I) or (II) to a patient in need of such treatment. The patient to be treated by the above method may include a human or non-human mammalian.

The present invention will be described in further detail with reference to Examples. However, it should be understood that the present invention is not restricted by the specific Examples.

PREPARATION EXAMPLE 1

Synthesis of 4-pentyloxy-1H-pyridin-2-one

A solution of pentanol (2.7 g, 31 mmol) and tert-butoxide (3.5 g, 31 mmol) in solvent of tert-butanol was stirred for 1 hr at room temperature followed by addition of 4-nitropyridine-N-oxide (4 g, 28.6 mmol). After the reaction was done, the resulting solution was worked up with ethyl acetate and water, separated and the organic solvent was dried completely. After the addition of toluene, the solvent was removed under a reduced pressure. Acetic anhydride (40 ml) was added to the residual mixture and refluxed for 3 hrs. Acetic anhydride was dried completely followed by adding of MeOH (20 ml) and 3N NaOH (5 ml) and stirring 1 hr. MeOH was dried adequately then the residual mixture was made neutral with 6N HCl. The resulting solution was extracted with Ethyl acetate (80 ml) and subjected to silica gel column chromatography (ethyl acetate/MeOH, 10:1) to obtain the titled compound (2.3 g, 56%).

$^1$H NMR (CDCl$_3$, 300 MHz) δ 0.93 (t 3H), 1.33-1.44 (m, 4H), 1.72-1.79 (m, 2H), 3.91 (t, 2H), 5.91-6.08 (m, 2H), 7.40 (d, 1H)

EXAMPLE 1

4-benzyloxy-1-(2-chloro-benzyl)-1H-pyridin-2-one

A solution of 4-benzyloxy-1H-pyridone (300 mg, 1.49 mmol) and NaH (60 mg, 1.49 mmol) in solvent of DMF was stirred for 30 min followed by adding 2-chlorobenzyl chloride (240 mg, 1.49 mmol) further stirring for 30 min at room temperature. The resulting solution was worked up with Water and dichloromethane and purified by column chromatography (ethyl acetate/hexane, 1:1) to obtain the titled compound (320 mg, 67%).

$^1$H NMR (CDCl$_3$, 300 MHz) δ 5.00 (s, 2H), 5.20 (s, 2H), 5.97 (dd, 1H), 6.04 (d, 1H), 7.17-7.39 (m, 10H)

EXAMPLES 2 TO 13

The procedure of Example 1 was repeated except the starting material to obtain the titled compound.

EXAMPLE 2

4-benzyloxy-1-(4-chloro-benzyl)-1H-pyridin-2-one $^1$H NMR (CDCl$_3$, 300 MHz) δ 4.96 (s, 2H), 5.01 (s, 2H), 5.93 (dd, 1H), 5.99 (d, 1H), 7.09 (d, 1H), 7.19 (d, 2H), 7.24 (d, 2H), 7.28-7.36 (m, 5H)

EXAMPLE 3

4-benzyloxy-1-(4-nitro-benzyl)-1H-pyridin-2-one $^1$H NMR (CDCl$_3$, 300 MHz) δ 5.08 (s, 2H), 5.47 (s, 2H), 6.39-6.60 (m, 2H), 7.35-7.59 (m, 7H), 7.95 (d, 1H), 8.18-8.23 (m, 2H)

EXAMPLE 4

4-benzyloxy-1-(2,5-dichloro-benzyl)-1H-pyridin-2-one $^1$H NMR (CDCl$_3$, 300 MHz) δ 4.98 (s, 2H), 5.12 (s, 2H), 5.96-6.03 (m, 2H), 7.14-7.39 (m, 9H)

EXAMPLE 5

4-benzyloxy-1-(2,4-dichloro-benzyl)-1H-pyridin-2-one $^1$H NMR (CDCl$_3$, 300 MHz) δ 5.00 (s, 2H), 5.14 (s, 2H), 5.97-6.03 (m, 2H), 7.18-7.41 (m, 9H)

EXAMPLE 6

4-benzyloxy-2-(4-methoxy-benzyloxy)-pyridine $^1$H NMR (CDCl$_3$, 300 MHz) δ 3.80 (s, 3H), 5.05 (s, 2H), 5.28 (s, 2H), 6.31 (d, 1H), 6.55 (dd, 1H), 6.90 (d, 1H), 7.29-7.40 (m, 7H), 7.99 (d, 1H)

EXAMPLE 7

4-benzyloxy-1-(4-methoxy-benzyl)-1H-pyridin-2-one $^1$H NMR (CDCl$_3$, 300 MHz) δ 3.79 (s, 3H), 4.98 (s, 2H), 5.01 (s, 2H) 5.92 (dd, 1H), 6.01 (d, 1H), 6.86 (d, 2H), 7.11 (d, 1H), 7.22-7.26 (m, 3H), 7.34-7.38 (m, 4H)

EXAMPLE 8

4-benzyloxy-2-(4-methyl-benzyloxy)-pyridine $^1$H NMR (CDCl$_3$, 300 MHz) δ 2.37 (s, 3H), 5.06 (s, 2H), 5.33 (s, 2H), 6.34 (d 1H), 6.56 (dd, 1H), 7.19 (d, 2H), 7.34-7.41 (m, 7H), 8.00 (d, 1H)

EXAMPLE 9

4-benzyloxy-1-(4-methyl-benzyl)-1H-pyridin-2-one $^1$H NMR (CDCl$_3$, 300 MHz) δ 2.33 (s, 3H), 4.98 (s, 2H), 5.04 (s, 2H) 5.93 (dd, 1H), 6.02 (d, 1H), 7.10-7.19 (m, 5H), 7.34-7.38 (m, 5H)

EXAMPLE 10

4-benzyloxy-1-(6-chloro-pyridin-3-ylmethyl)-1H-pyridin-2-one $^1$H NMR (CDCl$_3$, 300 MHz) δ 4.99 (s, 2H), 5.04 (s, 2H), 6.00-6.02 (m, 2H), 7.15-7.38 (m, 7H), 7.66 (dd, 1H), 8.34-8.37 (m, 1H)

EXAMPLE 11

4-benzyloxy-1-(3-chloro-benzyl)-1H-pyridin-2-one $^1$H NMR (CDCl$_3$, 300 MHz) δ 4.96 (s, 2H), 5.01 (s, 2H), 5.94 (dd, 1H), 6.00 (d, 1H), 7.09-7.36 (m, 10H)

EXAMPLE 12

1-benzyl-4-benzyloxy-1H-pyridin-2-one $^1$H NMR (CDCl$_3$, 300 MHz) δ 4.96 (s, 2H), 5.06 (s, 2H), 5.92 (dd, 1H), 6.01 (d, 1H), 7.10 (d, 1H), 7.24-7.36 (m, 10H)

EXAMPLE 13

1-(4-amino-benzyl)-4-benzyloxy-1H-pyridin-2-one $^1$H NMR (CDCl$_3$, 300 MHz) δ 3.73 (br s, 2H), 4.95 (s, 2H), 4.97 (s, 2H), 5.90 (dd, 1H), 6.00 (d, 1H), 6.63 (d, 2H), 7.08-7.37 (m, 8H)

EXAMPLE 14

1-(2,4-dichloro-benzyl)-4-hydroxy-1H-pyridin-2-one 4-benzyloxy-1-(2,4-dichloro-benzyl)-1H-pyridin-2-one synthesized by the same method as Example 1 was hydrogenated with Pd/C to obtain the titled compound.

$^1$H NMR (CD$_3$OD, 300 MHz) δ 5.17 (s, 2H), 5.86 (d, 1H), 6.10 (dd, 1H), 6.99 (d, 1H), 7.27-7.32 (m, 1H), 7.50-7.52 (m, 2H)

EXAMPLE 15

3-benzyl-1-(2,4-dichloro-benzyl)-4-hydroxy-1H-pyridin-2-one 1-(2,4-dichloro-benzyl)-4-hydroxy-1H-pyridin-2-one synthesized in Example 14 was dissolved in DMF followed by adding NaH and benzyl bromide to obtain 4-benzyloxy-1-(2,4-dichloro-benzyl)-1H-pyridin-2-one and the titled compound in the ratio of 1:1.

$^1$H NMR (CDCl$_3$, 300 MHz) δ 4.00 (s, 2H), 5.13 (s, 2H), 5.87 (d, 1H), 7.25-7.33 (m, 9H)

EXAMPLES 16 TO 225

The procedure of Example 1 was repeated except the starting material to obtain the titled compound.

EXAMPLE 16

4-(biphenyl-4-ylmethoxy)-1-(2,4-dichloro-benzyl)-1H-pyridin-2-one $^1$H NMR (CDCl$_3$, 300 MHz) δ 5.04 (s, 2H), 5.15 (s, 2H), 6.01 (dd, 1H), 6.06 (d, 1H), 7.22-7.63 (m, 13H)

EXAMPLE 17

1-(2,4-dichloro-benzyl)-4-(2,4-dichloro-benzyloxy)-1H-pyridin-2-one $^1$H NMR (CDCl$_3$, 300 MHz) δ 5.06 (s, 2H), 5.15 (s, 2H), 5.99-6.01 (m, 2H), 7.15-7.44 (m, 7H)

EXAMPLE 18

4-(2-chloro-benzyloxy)-1-(2,4-dichloro-benzyl)-1H-pyridin-2-one $^1$H NMR (CDCl$_3$, 300 MHz) δ 5.11 (s, 2H), 5.16 (s, 2H), 6.00-6.04 (m, 2H), 7.21-7.47 (m, 8H)

EXAMPLE 19

1-(2,4-dichloro-benzyl)-4-methoxy-1H-pyridin-2-one $^1$H NMR (CDCl$_3$, 300 MHz) δ 3.78 (s, 3H), 5.14 (s, 2H), 5.91-5.94 (m, 2H), 7.16-7.22 (m, 3H), 7.41 (s, 1H)

EXAMPLE 20

1-(2,4-dichloro-benzyl)-4-isopropoxy-1H-pyridin-2-one $^1$H NMR (CDCl$_3$, 300 MHz) δ 1.34 (d, 6H), 4.47-4.55 (m, 1H), 5.86-5.91 (m, 2H), 7.15-7.21 (m, 3H), 7.41 (s, 1H)

EXAMPLE 21

4-cyclohexylmethoxy-1-(2,4-dichloro-benzyl)-1H-pyridin-2-one $^1$H NMR (CDCl$_3$, 300 MHz) δ 0.86-1.83 (m, 11H), 3.71 (d, 2H), 5.14 (s, 2H), 5.90-5.94 (m, 2H), 7.15-7.23 (m, 3H), 7.40 (s, 1H)

EXAMPLE 22

3-(2-chloro-benzyl)-4-hydroxy-1H-pyridin-2-one $^1$H NMR (CD$_3$OD, 300 MHz) δ 3.82 (s, 2H), 6.12 (d, 1H), 7.06-7.28 (m, 5H)

EXAMPLE 23

1-(2,4-dichloro-benzyl)-4-propoxy-1H-pyridin-2-one $^1$H NMR (CDCl$_3$, 300 MHz) δ 1.02 (t 3H), 1.74-1.85 (m, 2H), 3.88 (t, 2H), 5.14 (s, 2H), 5.91-5.94 (m, 2H), 7.15-7.24 (m, 3H), 7.40 (s, 1H)

EXAMPLE 24

1-(2,4-dichloro-benzyl)-4-isobutoxy-1H-pyridin-2-one $^1$H NMR (CDCl$_3$, 300 MHz) δ 1.00 (d, 6H), 2.03-2.12 (m, 1H), 3.68 (d, 2H), 5.14 (s, 2H), 5.90-5.95 (m, 2H), 7.15-7.23 (m, 3H), 7.41 (s, 1H)

EXAMPLE 25

4-butoxy-1-(2,4-dichloro-benzyl)-1H-pyridin-2-one $^1$H NMR (CDCl$_3$, 300 MHz) δ 0.97 (t, 3H), 1.40-1.52 (m, 2H), 1.71-1.80 (m, 2H), 3.92 (t, 2H), 5.14 (s, 2H), 5.90-5.92 (m, 2H), 7.15-7.23 (m, 3H), 7.41 (s, 1H)

EXAMPLE 26

1-(2,4-dichloro-benzyl)-4-octyloxy-1H-pyridin-2-one $^1$H NMR (CDCl$_3$, 300 MHz) δ 0.84 (t 3H), 1.24-1.52 (m, 10H), 1.67-1.76 (m, 2H), 3.86 (t, 2H), 5.09 (s, 2H), 5.86-5.89 (m, 2H), 7.10-7.18 (m, 3H), 7.36 (s, 1H)

EXAMPLE 27

1-(2,4-dichloro-benzyl)-4-(4-methyl-pentoxy)-1H-pyridin-2-one $^1$H NMR (CDCl$_3$, 300 MHz) δ 0.86 (d, 6H), 1.24-1.29 (m, 2H), 1.50-1.59 (m, 1H), 1.67-1.77 (m, 2H), 3.86 (t, 2H), 5.10 (s, 2H), 5.87-5.90 (m, 2H), 7.11-7.16 (m, 3H), 7.36 (s, 1H)

EXAMPLE 28

4-(but-3-enyloxy)-1-(2,4-dichloro-benzyl)-1H-pyridin-2-one $^1$H NMR (CDCl$_3$, 300 MHz) δ 2.48 (q, 2H), 3.93 (t, 2H), 5.06-5.15 (m, 4H), 5.76-5.89 (m, 3H), 7.11-7.15 (m, 3H), 7.36 (s, 1H)

EXAMPLE 29

1-(2,4-dichloro-benzyl)-1H-pyridin-2-one $^1$H NMR (CDCl$_3$, 300 MHz) δ 1.78-1.87 (m, 2H), 2.16 (q, 2H), 3.89 (t, 2H), 4.95-5.09 (m, 4H), 5.71-5.88 (m, 3H), 7.11-7.15 (m, 3H), 7.36 (s, 1H)

EXAMPLE 30

1-(2,4-dichloro-benzyl)-4-pentyloxy-1H-pyridin-2-one $^1$H NMR (CDCl$_3$, 300 MHz) δ 0.93 (t, 3H), 1.33-1.44 (m, 4H), 1.72-1.79 (m, 2H), 3.91 (t, 2H), 5.14 (s, 2H), 7.16-7.22 (m, 3H), 7.40 (d, 1H)

EXAMPLE 31

[1-(2,4-dichloro-benzyl)-2-oxo-1,2-dihydro-pyridin-4-yloxy]-acetic acid ethylester $^1$H NMR (CDCl$_3$, 300 MHz) δ 3.77 (s, 3H), 4.54 (s, 2H), 5.09 (s, 2H), 5.77 (d, 1H), 5.99 (dd, 1H), 7.17-7.22 (m, 3H), 7.37 (s, 1H)

EXAMPLE 32

1-(2,4-dichloro-benzyl)-4-(3-methyl-butoxy)-1H-pyridin-2-one $^1$H NMR (CDCl$_3$, 300 MHz) δ 0.87 (d, 6H), 1.54-1.76 (m, 3H), 3.86 (t, 2H), 5.00 (s, 2H), 5.79 (dd, 1H), 5.86 (d, 1H), 7.04 (d, 1H), 7.13-7.27 (m, 3H)

EXAMPLE 33

1-benzyl-4-pentyloxy-1H-pyridin-2-one $^1$H NMR (CDCl$_3$, 300 MHz) δ 0.93 (t, 3H), 1.32-1.40 (m, 4H), 1.75-1.79 (m, 2H), 3.92 (t, 2H), 5.10 (s, 2H), 5.87-5.93 (m, 2H), 7.11 (d, 1H), 7.25-7.32 (m, 5H)

EXAMPLE 34

1-(2-chloro-benzyl)-4-pentyloxy-1H-pyridin-2-one $^1$H NMR (CDCl$_3$, 300 MHz) δ 0.92 (t, 3H), 1.31-1.42 (m, 4H), 1.72-1.79 (m, 2H), 3.91 (t, 2H), 5.19 (S, 2H), 5.89-5.92 (m, 2H), 7.14-7.26 (m, 4H), 7.37-7.40 (m, 1H)

EXAMPLE 35

4-pentyloxy-1-propyl-1H-pyridin-2-one $^1$H NMR (CDCl$_3$, 300 MHz) δ 0.90-0.96 (m, 6H), 1.28-1.38 (m, 4H), 1.67-1.80 (m, 4H), 3.82 (t, 2H), 3.89 (t, 2H), 5.87 (d, 2H), 7.07-7.10 (m, 1H)

EXAMPLE 36

1-butyl-4-pentyloxy-1H-pyridin-2-one $^1$H NMR (CDCl$_3$, 300 MHz) δ 0.89-0.96 (m, 6H), 1.29-1.42 (m, 6H), 1.64-1.78 (m, 4H), 3.83-3.91 (m, 4H), 5.86-5.88 (m, 2H), 7.07-7.10 (m, 1H)

EXAMPLE 37

1-isobutyl-4-pentyloxy-1H-pyridin-2-one $^1$H NMR (CDCl$_3$, 300 MHz) δ 0.91-0.93 (m, 9H), 1.33-1.39 (m, 4H), 1.71-1.78 (m, 2H), 2.10-2.19 (m, 1H), 3.65 (d, 2H), 3.89 (t, 2H), 5.84-5.87 (m, 2H), 7.05 (d, 1H)

EXAMPLE 38

1-(3-methyl-butyl)-4-pentyloxy-1H-pyridin-2-one $^1$H NMR (CDCl$_3$, 300 MHz) δ 0.90-0.96 (m, 9H), 1.33-1.39 (m, 4H), 1.55-1.78 (m, 5H), 3.84-3.91 (m, 4H), 5.86-5.88 (m, 2H), 7.07-7.10 (m, 1H)

EXAMPLE 39

1-(2,4-dichloro-benzyl)-4-hexyloxy-1H-pyridin-2-one $^1$H NMR (CDCl$_3$, 300 MHz) δ 0.90 (t, 3H), 1.25-1.34 (m, 4H), 1.71-1.80 (m, 2H), 3.91 (t, 2H), 5.14 (s, 2H), 5.91-5.93 (m, 2H), 7.14-7.23 (m, 3H), 7.40 (s, 1H)

EXAMPLE 40

1-(2,4-dichloro-benzyl)-4-heptoxy-1H-pyridin-2-one $^1$H NMR (CDCl$_3$, 300 MHz) δ 0.75 (t, 3H), 1.09-1.54 (m, 8H), 1.71-1.80 (m, 2H), 3.91 (t, 2H), 5.13 (s, 2H), 5.86-5.92 (m, 2H), 7.14-7.22 (m, 3H), 7.40 (s, 1H)

EXAMPLE 41

1-(4-chloro-benzyl)-4-pentyloxy-1H-pyridin-2-one $^1$H NMR (CDCl$_3$, 300 MHz) δ 0.92 (t, 3H), 1.33-1.42 (m, 4H), 1.71-1.80 (m, 2H), 3.90 (t, 2H), 5.04 (s, 2H), 5.87-5.91 (m, 2H), 7.08 (d, 1H), 7.20 (d, 2H), 7.30 (d, 2H)

EXAMPLE 42

4-aryloxy-1-(2,4-dichloro-benzyl)-1H-pyridin-2-one $^1$H NMR (CDCl$_3$, 300 MHz) δ 4.48 (d, 2H), 5.14 (s, 2H), 5.32-5.45 (m, 2H), 5.94-6.07 (m, 3H), 7.18-7.20 (m, 3H), 7.41 (s, 1H)

EXAMPLE 43

1-(2,4-dichloro-benzyl)-4-(3-methoxy-propoxy)-1H-pyridin-2-one $^1$H NMR (CDCl$_3$, 300 MHz) δ 2.01-2.07 (m, 2H), 3.35 (s, 3H), 3.52 (t, 2H), 4.02 (t, 2H), 5.14 (s, 2H), 5.91-5.94 (m, 2H), 7.16-7.20 (m, 3H), 7.41 (s, 1H)

EXAMPLE 44

1-(2,4-dichloro-benzyl)-4-(3-ethylamino-propoxy)-1H-pyridin-2-one $^1$H NMR (CDCl$_3$, 300 MHz) δ 1.25-1.52 (m, 5H), 2.92-3.05 (m, 4H), 4.03 (t, 2H), 5.13 (s, 2H), 5.91-5.93 (m, 2H), 7.17-7.19 (m, 3H), 7.41 (s, 1H), 8.48 (br s, 1H)

EXAMPLE 45

1-(2,4-dichloro-benzyl)-4-(2-ethoxy-ethoxy)-1H-pyridin-2-one $^1$H NMR (CDCl$_3$, 300 MHz) δ 1.25 (t, 3H), 3.58 (q, 2H), 3.77 (t, 2H), 4.08 (t, 2H), 5.14 (s, 2H), 5.92 (d, 1H), 5.99 (dd, 1H), 7.16-7.23 (m, 3H), 7.41 (s, 1H)

EXAMPLE 46

1-(3-methyl-but-2-enyl)-4-pentyloxy-1H-pyridin-2-one $^1$H NMR (CDCl$_3$, 300 MHz) δ 0.92 (t, 3H), 1.33-1.38 (m, 4H), 1.71-1.73 (m, 2H), 1.76 (s, 6H), 3.89 (t, 2H), 4.47 (d, 2H), 5.27 (t, 1H), 5.87-5.88 (m, 2H), 7.10-7.13 (m, 1H)

EXAMPLE 47

5-(2-oxo-4-pentyloxy-2H-pyridin-1-ylmethyl)-furan-2-carboxyl acid ethylester $^1$H NMR (CDCl$_3$, 300 MHz) δ 0.92 (t, 3H), 1.33-1.44 (m, 7H), 1.73-1.80 (m, 2H), 3.89 (t, 2H), 4.34 (q, 2H), 5.09 (s, 2H), 5.86 (d, 1H), 5.92 (dd, 1H), 6.47 (d, 1H), 7.09 (d, 1H), 7.29 (d, 1H)

EXAMPLE 48

5-(2-oxo-4-pentyloxy-2H-pyridin-1-ylmethyl)-furan-2-carboxyl acid $^1$H NMR (CD$_3$OD, 300 MHz) δ 0.94 (t 3H), 1.37-1.45 (m, 4H), 1.73-1.80 (m, 2H), 3.97 (t, 2H), 5.13 (s, 2H), 5.89 (d, 1H), 6.11 (dd, 1H), 6.41 (d, 1H), 6.93 (d, 1H), 7.65 (d, 1H)

EXAMPLE 49

4-pentyloxy-1-thiazol-4-ylmethyl-1H-pyridin-2-one $^1$H NMR (CDCl$_3$, 300 MHz) δ 0.92 (t, 3H), 1.32-1.44 (m, 4H), 1.70-1.80 (m, 2H), 3.89 (t, 2H), 5.22 (s, 2H), 5.88 (d, 1H), 5.92 (dd, 1H), 7.38-7.42 (m, 2H), 8.76 (s, 1H)

EXAMPLE 50

4-pentyloxy-1-pyridin-3-ylmethyl-1H-pyridin-2-one $^1$H NMR (CDCl$_3$, 300 MHz) δ 0.93 (t, 3H), 1.32-1.45 (m, 4H), 1.74-1.83 (m, 2H), 3.96 (t, 2H), 5.55 (s, 2H), 6.29 (d, 1H), 6.50 (dd, 1H), 7.40 (s, 1H), 7.96 (d, 1H), 8.84 (d, 1H)

EXAMPLE 51

1-(2,4-dichloro-benzyl)-4-(4-methyl-pent-3-enyloxy)-1H-pyridin-2-one $^1$H NMR (CDCl$_3$, 300 MHz) δ 1.65 (s, 3H), 1.73 (s, 3H), 2.46 (q, 2H), 3.89 (t, 2H), 5.14 (s, 2H), 5.91-5.94 (m, 2H), 7.15-7.13 (m, 3H), 7.27 (s, 1H), 7.41 (s, 1H)

EXAMPLE 52

1-(2,4-dichloro-benzyl)-4-(3-methoxy-propoxy)-1H-pyridin-2-one $^1$H NMR (CDCl$_3$, 300 MHz) δ 0.88 (d, 6H), 1.18-1.26 (m, 4H), 1.37-1.77 (m, 5H), 3.92 (t, 2H), 5.14 (s, 2H), 5.91-5.93 (m, 2H), 7.15-7.23 (m, 3H), 7.41 (s, 1H)

EXAMPLE 53

1-(2,4-dichloro-benzyl)-4-phenetyloxy-1H-pyridin-2-one $^1$H NMR (CDCl$_3$, 300 MHz) δ 3.09 (t, 2H), 4.15 (t 2H), 5.14 (s, 2H), 5.91-5.99 (m, 2H), 7.16-7.40 (m, 9H)

EXAMPLE 54

1-(2-methyl-benzyl)-4-pentyloxy-1H-pyridin-2-one $^1$H NMR (CDCl$_3$, 300 MHz) δ 0.93 (t, 3H), 1.33-1.43 (m, 4H), 1.75-1.79 (m, 2H), 2.28 (s, 3H), 3.92 (t, 2H), 5.08 (s, 2H), 5.86 (dd, 1H), 5.94 (d, 1H), 6.93 (d, 1H), 7.03 (d, 1H), 7.15-7.23 (m, 3H)

EXAMPLE 55

4-pentyl-1-phenetyl-1H-pyridin-2-one $^1$H NMR (CDCl$_3$, 300 MHz) δ 0.86 (t, 3H), 1.27-1.33 (m, 4H), 1.65-1.72 (m, 2H), 2.96 (t, 2H), 3.83 (t, 2H), 4.01 (t, 2H), 5.65 (dd, 1H), 5.83 (d, 1H), 6.65 (d, 1H), 7.08 (d, 1H), 7.13-7.25 (m, 3H)

EXAMPLE 56

1-(2,4-dichloro-5-fluoro-benzyl)-4-pentyloxy-1H-pyridin-2-one $^1$H NMR (CDCl$_3$, 300 MHz) δ 0.93 (t, 3H), 1.31-1.43 (m, 4H), 1.73-1.80 (m, 2H), 3.92 (t, 2H), 5.10 (s, 2H), 5.92-5.96 (m, 2H), 7.02 (d, 1H), 7.16 (d, 1H), 7.44 (d, 1H)

EXAMPLE 57

1-(3,4-dichloro-benzyl)-4-pentyloxy-1H-pyridin-2-one $^1$H NMR (CDCl$_3$, 300 MHz) δ 0.93 (t, 3H), 1.31-1.46 (m, 4H), 1.73-1.82 (m, 2H), 3.92 (t, 2H), 5.02 (s, 2H), 5.92-5.95 (m, 2H), 7.10-7.15 (m, 2H), 7.36-7.42 (m, 2H)

EXAMPLE 58

1-(3,4-difluoro-benzyl)-4-pentyloxy-1H-pyridin-2-one $^1$H NMR (CDCl$_3$, 300 MHz) δ 0.93 (t, 3H), 1.32-1.43 (m, 4H), 1.73-1.80 (m, 2H), 3.92 (t, 2H), 5.02 (s, 2H), 5.91-5.94 (m, 2H), 7.03-7.17 (m, 4H)

EXAMPLE 59

4-(4-benzyloxy-butoxy)-1-(2,4-dichloro-benzyl)-1H-pyridin-2-one $^1$H NMR (CDCl$_3$, 300 MHz) δ 1.68-1.94 (m, 4H), 3.54 (t, 2H), 3.96 (t, 2H), 4.53 (s, 2H), 5.15 (s, 2H), 5.90-5.93 (m, 2H), 7.16-7.42 (m, 9H)

EXAMPLE 60

1-(2,4-dichloro-benzyl)-4-(4-hydroxy-butoxy)-1H-pyridin-2-one $^1$H NMR (CDCl$_3$, 300 MHz) δ 1.70-1.91 (m, 4H), 3.72 (t, 2H), 3.98 (t, 2H), 5.14 (s, 2H), 5.92-5.94 (m, 2H), 7.16-7.25 (m, 3H), 7.41 (s, 1H)

EXAMPLE 61

4-(5-benzyloxy-pentyloxy)-1-(2,4-dichloro-benzyl)-1H-pyridin-2-one $^1$H NMR (CDCl$_3$, 300 MHz) δ 1.52-1.85 (m, 6H), 3.51 (t, 2H), 3.94 (t, 2H), 4.53 (s, 2H), 5.15 (s, 2H), 5.90-5.94 (m, 2H), 7.16-7.42 (m, 9H)

EXAMPLE 62

1-(2,4-dichloro-benzyl)-4-(5-hydroxy-pentyloxy)-1H-pyridin-2-one $^1$H NMR (CDCl$_3$, 300 MHz) δ 1.44-1.83 (m, 6H), 3.70 (t, 2H), 3.93 (t, 2H), 5.14 (s, 2H), 5.91-5.92 (m, 2H), 7.15-7.20 (m, 3H), 7.41 (s, 1H)

EXAMPLE 63

1-(6-chloro-benzo[1,3]dioxol-5-ylmethyl)-4-pentyloxy-1H-pyridin-2-one $^1$H NMR (CDCl$_3$, 300 MHz) δ 0.93 (t, 3H), 1.35-1.43 (m, 4H), 1.74-1.79 (m, 2H), 3.91 (t, 2H), 5.10 (s, 2H), 5.88-5.91 (m, 2H), 5.96 (s, 2H), 6.81 (s, 1H), 6.84 (s, 1H), 7.18 (dd, 1H)

EXAMPLE 64

1-(2,4-dichloro-benzyl)-4-(2-methyl-benzyloxy)-1H-pyridin-2-one $^1$H NMR (CDCl$_3$, 300 MHz) δ 2.35 (s, 3H), 4.99 (s, 2H), 5.16 (s, 2H) 5.98 (dd, 1H), 6.08 (d, 1H), 7.20-7.42 (m, 8H)

EXAMPLE 65

1-(2,4-dichloro-benzyl)-4-(4-methyl-benzyloxy)-1H-pyridin-2-one $^1$H NMR (CDCl$_3$, 300 MHz) δ 2.37 (s, 3H), 4.95 (s, 2H), 5.15 (s, 2H) 5.98 (dd, 1H), 6.03 (d, 1H), 7.18-7.30 (m, 8H)

EXAMPLE 66

1-(2-nitro-benzyl)-4-pentyloxy-1H-pyridin-2-one $^1$H NMR (CDCl$_3$, 300 MHz) δ 0.93 (t, 3H), 1.34-1.43 (m, 4H), 1.73-1.82 (m, 2H), 3.93 (t, 2H), 5.46 (s, 2H), 5.93 (d, 1H), 5.98 (dd, 1H), 7.10 (d, 1H), 7.17 (d, 1H), 7.44 (t, 1H), 7.56 (t, 1H), 8.10 (d, 1H)

EXAMPLE 67

1-(2-amino-benzyl)-4-pentyloxy-1H-pyridin-2-one $^1$H NMR (CDCl$_3$, 300 MHz) δ 0.91 (t, 3H), 1.30-1.39 (m, 4H), 1.69-1.76 (m, 2H), 3.89 (t, 2H), 4.75 (br s, 2H), 5.00 (s, 2H), 5.89-5.93 (m, 2H), 6.62-6.70 (m, 2H), 7.09-7.23 (m, 3H)

EXAMPLE 68

N-[2-(2-oxo-4-pentyloxy-2H-pyridin-1-ylmethyl)-phenyl]-acetamide $^1$H NMR (CDCl$_3$, 300 MHz) δ 0.92 (t, 3H), 1.26-1.38 (m, 4H), 1.74-1.78 (m, 2H), 2.29 (s, 3H), 3.91 (t, 2H), 5.01 (s, 2H), 5.94 (d, 1H), 6.01 (dd, 1H), 7.08 (t, 1H), 7.31-7.38 (m, 3H), 8.20 (d, 1H), 10.56 (br s, 1H)

EXAMPLE 69

4-pentyloxy-1-(2-trifluoromethyl-benzyl)-1H-pyridin-2-one $^1$H NMR (CDCl$_3$, 300 MHz) δ 0.94 (t, 3H), 1.31-1.42 (m, 4H), 1.75-1.81 (m, 2H), 3.95 (t, 2H), 5.32 (s, 2H), 5.93 (dd, 1H), 5.98 (d, 1H), 7.04 (d, 1H), 7.15 (d, 1H), 7.38 (t, 1H), 7.49 (t, 1H), 7.69 (d, 1H)

EXAMPLE 70

N-[4-(4-benzyloxy-2-oxo-2H-pyridin-1-ylmethyl)-phenyl]acetamide $^1$H NMR (CDCl$_3$, 300 MHz) δ 2.18 (s, 3H), 4.99 (s, 2H), 5.04 (s, 2H) 5.98 (dd, 1H), 6.02 (d, 1H), 7.14-7.46 (m, 10H), 7.82 (br s, 1H)

EXAMPLE 71

1-(2,4-dichloro-benzyl)-4-(naphthalen-2-ylmethoxy)-1H-pyridin-2-one $^1$H NMR (CDCl$_3$, 300 MHz) δ 5.15 (s, 2H), 5.16 (s, 2H), 5.99-6.09 (m, 2H), 7.18-7.55 (m, 7H), 7.83-7.90 (m, 4H)

EXAMPLE 72

1-naphthalen-2-ylmethyl-4-pentyloxy-1H-pyridin-2-one $^1$H NMR (CDCl$_3$, 300 MHz) δ 0.92 (t, 3H), 1.35-1.43 (m, 4H), 1.73-1.76 (m, 2H), 3.91 (t, 2H), 5.24 (s, 2H), 5.84-5.96 (m, 2H), 7.13 (d, 1H), 7.26-7.49 (m, 3H), 7.70 (s, 1H), 7.79-7.83 (m, 3H)

EXAMPLE 73

4-benzyloxy-1-(6-chloro-benzo[1,3]dioxol-5-ylmethyl)-1H-pyridin-2-one $^1$H NMR (CDCl$_3$, 300 MHz) δ 4.99 (s, 2H), 5.10 (s, 2H), 5.94-6.03 (m, 4H), 6.84 (d, 2H), 7.20 (d, 1H), 7.33-7.39 (m, 5H)

EXAMPLE 74

1-(6-chloro-benzo[1,3]dioxol-5-ylmethyl)-4-(3-methyl-butoxy)-1H-pyridin-2-one $^1$H NMR (CDCl$_3$, 300 MHz) δ 0.92 (d, 6H), 1.58-1.66 (m, 3H), 3.92 (t, 2H), 5.07 (s, 2H), 5.86 (dd, 1H), 5.90 (d, 1H), 5.93 (s, 2H), 6.80 (d, 2H), 7.14 (d, 1H)

EXAMPLE 75

1-(2-methyl-benzyl)-4-(3-methyl-butoxy)-1H-pyridin-2-one $^1$H NMR (CDCl$_3$, 300 MHz) δ 0.92 (d, 6H), 1.63 (q, 2H), 1.72-1.81 (m, 1H), 3.93 (t, 2H), 5.05 (s, 2H), 5.82 (dd, 1H), 5.92 (d, 1H), 6.90 (d, 1H), 7.01 (d, 1H), 7.13-7.20 (m, 3H)

EXAMPLE 76

4-(3-methyl-butoxy)-1-(2-nitro-benzyl)-1H-pyridin-2-one $^1$H NMR (CDCl$_3$, 300 MHz) δ 0.93 (d, 6H), 1.65 (q, 2H), 1.69-1.78 (m, 1H), 3.95 (t, 2H), 5.45 (s, 2H), 5.93-5.96 (m, 2H), 7.11 (d, 1H), 7.14 (d, 1H), 7.44 (t, 1H), 7.53 (t, 1H), 8.08 (d, 1H)

EXAMPLE 77

1-(2,4-dichloro-benzyl)-4-pentylamino-1H-pyridin-2-one $^1$H NMR (CDCl$_3$, 300 MHz) δ 0.88 (t, 3H), 1.24-1.34 (m, 4H), 1.57-1.84 (m, 2H), 3.19 (br s, 1H), 3.47 (q, 2H), 5.03 (s, 2H), 5.56 (d, 1H), 7.15-7.38 (m, 4H)

EXAMPLE 78

1-(2,3-dichloro-benzyl)-4-pentyloxy-1H-pyridin-2-one $^1$H NMR (CDCl$_3$, 300 MHz) δ 0.90 (t, 3H), 1.28-1.40 (m, 4H), 1.70-1.77 (m, 2H), 3.89 (t, 2H), 5.17 (s, 2H), 5.89-5.92 (m, 2H), 7.01 (d, 1H), 7.11-7.16 (m, 2H), 7.37 (d, 1H)

EXAMPLE 79

1-(2-methoxy-benzyl)-4-pentyloxy-1H-pyridin-2-one $^1$H NMR (CDCl$_3$, 300 MHz) δ 0.90 (t, 3H), 1.27-1.36 (m, 4H), 1.68-1.77 (m, 2H), 3.83 (s, 3H), 3.87 (t, 2H), 5.05 (s, 2H), 5.81 (dd, 1H), 5.86 (d, 1H), 6.84-6.92 (m, 2H), 7.18-7.27 (m, 3H)

EXAMPLE 80

1-(2,3-dimethoxy-benzyl)-4-pentyloxy-1H-pyridin-2-one $^1$H NMR (CDCl$_3$, 300 MHz) δ0.89 (t 3H), 1.29-1.38 (m, 4H), 1.67-1.74 (m, 2H), 3.81-3.88 (m, 8H), 5.08 (s, 2H), 5.80 (dd, 1H), 5.86 (d, 1H), 6.82-6.87 (m, 2H), 6.98 (t, 1H), 7.18 (d, 1H)

EXAMPLE 81

4-(5-benzyloxy-pentyloxy)-1-(6-chloro-benzo[1,3]dioxol-5-ylmethyl)-1H-pyridin-2-one $^1$H NMR (CD$_3$OD, 300 MHz) δ 1.47-1.53 (m, 2H), 1.61-1.66 (m, 2H), 1.74-1.78 (m, 2H), 3.48 (t, 2H), 3.96 (t, 2H), 4.45 (s, 2H), 5.06 (s, 2H), 5.90 (s, 1H), 5.94 (s, 2H), 6.06 (dd, 1H), 6.61 (s, 1H), 6.90 (s, 1H), 7.22-7.29 (m, 5H), 7.42 (d, 1H)

EXAMPLE 82

1-(2-chloro-benzyl)-4-(3-methyl-butoxy)-1H-pyridin-2-one $^1$H NMR (CDCl$_3$, 300 MHz) δ 0.93 (d, 6H), 1.60-1.82 (m, 3H), 3.94 (t, 2H), 5.17 (s, 2H), 5.86-5.94 (m, 2H), 7.12-7.40 (m, 5H)

EXAMPLE 83

1-(3,4-dichloro-benzyl)-4-(3-methyl-butoxy)-1H-pyridin-2-one $^1$H NMR (CDCl$_3$, 300 MHz) δ 0.92 (d, 6H), 1.63 (q, 2H), 1.72-1.81 (m, 1H), 3.92 (t, 2H), 4.99 (s, 2H), 5.87-5.90 (m, 2H), 7.05-7.12 (m, 2H), 7.33-7.38 (m, 2H)

EXAMPLE 84

1-(2,4-dichloro-5-fluoro-benzyl)-4-(3-methyl-butoxy)-1H-pyridin-2-one $^1$H NMR (CDCl$_3$, 300 MHz) δ 0.92 (d, 6H), 1.64 (q, 2H), 1.71-1.82 (m, 1H), 3.93 (t, 2H), 5.08 (s, 2H), 5.90-5.92 (m, 2H), 7.00 (d, 1H), 7.12-7.15 (m, 1H), 7.42 (d, 1H)

EXAMPLE 85

1-benzyl-4-(3-methyl-butoxy)-1H-pyridin-2-one $^1$H NMR (CDCl$_3$, 300 MHz) δ 0.95 (d, 6H), 1.59-1.78 (m, 3H), 3.93 (t, 2H), 5.08 (s, 2H), 5.83-5.93 (m, 2H), 7.07-7.36 (m, 6H)

EXAMPLE 86

1-(4-chloro-benzyl)-4-(3-methyl-butoxy)-1H-pyridin-2-one $^1$H NMR (CDCl$_3$, 300 MHz) δ 0.92 (d, 6H), 1.62 (q, 2H), 1.71-1.80 (m, 1H), 3.91 (t, 2H), 5.01 (s, 2H), 5.85 (dd, 1H), 5.89 (d, 1H), 7.06 (d, 1H), 7.19 (d, 2H), 7.27 (d, 2H)

EXAMPLE 87

1-(2,4-dichloro-benzyl)-4-pentyloxy-1H-pyrimidin-2-one $^1$H NMR (CDCl$_3$, 300 MHz) δ 0.88 (t, 3H), 1.32-1.36 (m, 4H), 1.61-1.73 (m, 2H), 4.33 (t, 2H), 5.07 (s, 2H), 5.83 (d, 1H), 7.22 (d, 1H), 7.35-7.45 (m, 3H)

EXAMPLE 88

1-(2,4-dichloro-benzyl)-4-(4-methyl-pentyloxy)-1H-pyrimidin-2-one

¹H NMR (CDCl₃, 300 MHz) δ 0.89 (d, 6H), 1.20-1.76 (m, 5H), 4.34 (t, 2H), 5.09 (s, 2H), 5.85 (d, 1H), 7.22 (d, 1H), 7.26-7.47 (m, 3H)

EXAMPLE 89

1-(2,4-dichloro-benzyl)-4-phenoxy-1H-pyrimidin-2-one

¹H NMR (CDCl₃, 300 MHz) δ 5.11 (d, 2H), 6.07 (d, 1H), 7.12-7.65 (m, 9H)

EXAMPLE 90

4-(butyl-methyl-amino)-1-(2,4-dichloro-benzyl)-1H-pyrimidin-2-one

¹H NMR (CDCl₃, 300 MHz) δ 0.90 (t 3H), 1.19-1.56 (m, 4H), 2.81-3.11 (m, 3H), 3.22-3.27 (m, 1H), 3.59-3.62 (m, 1H), 4.98 (s, 2H), 5.72-5.75 (m, 1H), 7.12-7.31 (m, 4H)

EXAMPLE 91

1-(2,4-dichloro-benzyl)-4-(2-diethylamino-ethoxy)-1H-pyrimidin-2-one

¹H NMR (CDCl₃, 300 MHz) δ 1.04 (t, 6H), 2.62 (q, 4H), 2.84 (t, 2H), 4.46 (t, 2H), 5.09 (s, 2H), 5.90 (d, 1H), 7.21-7.54 (m, 4H)

EXAMPLE 92

4-butoxy-1-(2,4-dichloro-benzyl)-1H-pyrimidin-2-one

¹H NMR (CDCl₃, 300 MHz) δ 0.95 (t, 3H), 1.39-1.46 (m, 2H), 1.69-1.74 (m, 2H), 4.37 (t, 2H), 5.10 (s, 2H), 5.87 (d, 1H), 7.23-7.48 (m, 4H)

EXAMPLE 93

1-(2,6-dichloro-benzyl)-4-pentyloxy-1H-pyridin-2-one

¹H NMR (CDCl₃, 300 MHz) δ 0.91 (t, 3H), 1.32-1.44 (m, 4H), 1.70-1.80 (m, 2H), 3.90 (t, 2H), 5.37 (s, 2H), 5.79 (dd, 1H), 5.91 (d, 1H), 6.71 (d, 1H), 7.25-7.41 (m, 3H)

EXAMPLE 94

1-(2-chloro-6-fluoro-benzyl)-4-pentyloxy-1H-pyridin-2-one

¹H NMR (CDCl₃, 300 MHz) δ 0.91 (t, 3H), 1.30-1.44 (m, 4H), 1.70-1.77 (m, 2H), 3.89 (t, 2H), 5.24 (s, 2H), 5.82 (dd, 1H), 5.88 (d, 1H), 6.92 (d, 1H), 7.05 (t, 1H), 7.24-7.33 (m, 2H)

EXAMPLE 95

1-(2-methyl-3-nitro-benzyl)-4-pentyloxy-1H-pyridin-2-one

¹H NMR (CDCl₃, 300 MHz) δ 0.92 (t, 3H), 1.33-1.43 (m, 4H), 1.75 (m, 2H), 2.40 (s, 3H), 3.92 (t, 2H), 5.13 (s, 2H), 5.92-5.95 (m, 2H), 6.98 (dd, 1H), 7.16 (d, 1H), 7.28 (t, 1H), 7.69 (d, 1H)

EXAMPLE 96

1-(3-amino-2-methyl-benzyl)-4-pentyloxy-1H-pyridin-2-one

¹H NMR (CDCl₃, 300 MHz) δ 0.92 (t, 3H), 1.33-1.43 (m, 4H), 1.71-1.80 (m, 2H), 2.01 (s, 3H), 3.72 (s, 2H), 3.91 (t, 2H), 5.05 (s, 2H), 5.81 (dd, 1H), 5.92 (d, 1H), 6.56 (d, 1H), 6.69 (d, 1H), 6.90 (d, 1H), 7.01 (t, 1H)

EXAMPLE 97

1-(4-methoxy-3,5-dimethyl-pyridin-2-ylmethyl)-4-pentyloxy-1H-pyridin-2-one

¹H NMR (CDCl₃, 300 MHz) δ 0.92 (t, 3H), 1.30-1.41 (m, 4H), 1.70-1.77 (m, 2H), 2.23 (s, 3H), 2.30 (s, 3H), 3.75 (s, 3H), 3.89 (t, 2H), 5.16 (s, 2H), 5.85-5.88 (m, 2H), 7.28-7.30 (m, 1H), 8.19 (s, 1H)

EXAMPLE 98

1-(6-chloro-benzo[1,3]dioxol-5-ylmethyl)-4-(5-hydroxy-pentyloxy)-1H-pyridin-2-one ¹H NMR (CD₃OD, 300 MHz) δ 1.48-1.58 (m, 4H), 1.75-1.80 (m, 2H), 3.54 (t, 2H), 3.97 (t, 2H), 5.06 (s, 2H), 5.89 (d, 1H), 5.94 (s, 2H), 6.07 (dd, 1H), 6.61 (s, 1H), 6.90 (s, 1H), 7.43 (d, 1H)

EXAMPLE 99

1-(2-methoxy-5-nitro-benzyl)-4-pentyloxy-1H-pyridin-2-one

¹H NMR (CDCl₃, 300 MHz) δ 0.92 (t, 3H), 1.36-1.44 (m, 4H), 1.74-1.80 (m, 2H), 3.91 (t, 2H), 3.97 (S, 3H), 5.07 (s, 2H), 5.90-5.95 (m, 2H), 7.17 (d, 1H), 7.21 (d, 1H), 8.03 (d, 1H), 8.19 (dd, 1H)

EXAMPLE 100

1-(5-amino-2-methoxy-benzyl)-4-pentyloxy-1H-pyridin-2-one

¹H NMR (CDCl₃, 300 MHz) δ 0.92 (t, 3H), 1.24-1.39 (m, 4H), 1.73-1.78 (m, 2H), 3.79 (s, 2H), 3.90 (t, 2H), 5.02 (s, 2H), 5.83 (dd, 1H), 5.89 (d, 1H), 6.59-6.74 (m, 3H), 7.23-7.27 (m, 3H)

EXAMPLE 101

1-(2-ethyl-benzyl)-4-pentyloxy-1H-pyridin-2-one

¹H NMR (CDCl₃, 300 MHz) δ 0.93 (t, 3H), 1.18 (t, 3H), 1.34-1.43 (m, 4H), 1.73-1.79 (m, 2H), 2.63 (q, 2H), 3.93 (t,

2H), 5.12 (s, 2H), 5.84 (dd, 1H), 5.94 (d, 1H), 6.92 (d, 1H), 7.05 (d, 1H), 7.16-7.32 (m, 3H)

EXAMPLE 102

1-(2-chloro-5-nitro-benzyl)-4-pentyloxy-1H-pyridin-2-one $^1$H NMR (CDCl$_3$, 300 MHz) δ 0.93 (t, 3H), 1.32-1.46 (m, 4H), 1.72-1.82 (m, 2H), 3.94 (t, 2H), 5.19 (s, 2H), 5.94 (dd, 1H), 6.00 (d, 1H), 7.18 (d, 1H), 7.55 (d, 1H), 7.96 (d, 1H), 9.09 (dd, 1H)

EXAMPLE 103

1-(5-amino-2-chloro-benzyl)-4-pentyloxy-1H-pyridin-2-one $^1$H NMR (CDCl$_3$, 300 MHz) δ 0.93 (t, 3H), 1.31-1.43 (m, 4H), 1.72-1.79 (m, 2H), 3.91 (t, 2H), 5.11 (s, 2H), 5.87-5.91 (m, 2H), 6.52-6.55 (m, 2H), 7.11-7.18 (m, 2H)

EXAMPLE 104

1-(4-methoxy-2,3-dimethyl-benzyl)-4-pentyloxy-1H-pyridin-2-one $^1$H NMR (CDCl$_3$, 300 MHz) δ 0.93 (t, 3H), 1.31-1.42 (m, 4H), 1.72-1.81 (m, 2H), 2.12 (s, 3H), 2.16 (s, 3H), 3.82 (s, 3H), 3.91 (t, 2H), 5.04 (s, 2H), 5.80 (dd, 1H), 5.93 (d, 1H), 6.71 (d, 1H), 6.85 (d, 1H), 6.97 (d, 1H)

EXAMPLE 105

1-(2-methyl-pyridin-3-ylmethyl)-4-pentyloxy-1H-pyridin-2-one $^1$H NMR (CDCl$_3$, 300 MHz) δ 0.93 (t, 3H), 1.32-1.47 (m, 4H), 1.73-1.83 (m, 2H), 2.56 (s, 3H), 3.93 (t, 2H), 5.09 (s, 2H), 5.91-5.94 (m, 2H), 7.00 (d, 1H), 7.08-7.13 (m, 1H), 7.26-7.28 (m, 1H), 8.43 (d, 1H)

EXAMPLE 106

N-[4-chloro-3-(2-oxo-4-pentyloxy-2H-pyridin-1-ylmethyl)-phenyl]-acetamide $^1$HNMR(CDCl$_3$, 300 MHz) δ 0.93 (t, 3H), 1.29-1.45 (m, 4H), 1.71-1.78 (m, 2H), 2.10 (s, 3H), 3.87 (t, 2H), 5.16 (s, 2H), 5.89 (d, 1H), 5.99 (dd, 1H), 7.26-7.33 (m, 3H), 7.77 (d, 1H), 8.43 (br s, 1H)

EXAMPLE 107

1-(2,4-dichloro-benzyl)-4-(3-dimethylamino-propoxy)-1H-pyridin-2-one $^1$H NMR (CDCl$_3$, 300 MHz) δ 1.87-1.97 (m, 2H), 2.25 (s, 6H), 2.40 (t, 2H), 4.42 (t, 2H), 5.10 (s, 2H), 5.87 (d, 1H), 7.23-7.49 (m, 4H)

EXAMPLE 108

1-(2,4-dichloro-benzyl)-4-(4-dimethylamino-butoxy)-1H-pyridin-2-one $^1$H NMR (CDCl$_3$, 300 MHz) δ 1.52-1.81 (m, 4H), 2.22 (s, 6H), 2.29 (t, 2H), 4.38 (t, 2H), 5.10 (s, 2H), 5.86 (d, 1H), 7.23-7.48 (m, 4H)

EXAMPLE 109

1-(2,4-dichloro-benzyl)-4-(6-dimethylamino-hexyloxy)-1H-pyrimidin-2-one $^1$H NMR (CDCl$_3$, 300 MHz) δ 1.34-1.78 (m, 8H), 2.24-2.30 (m, 8H), 4.35 (t, 2H), 5.10 (s, 2H), 5.86 (d, 1H), 7.23-7.47 (m, 4H)

EXAMPLE 110

1-(2,4-dimethyl-benzyl)-4-pentyloxy-1H-pyridin-2-one $^1$H NMR (CDCl$_3$, 300 MHz) δ 0.92 (t, 3H), 1.33-1.42 (m, 4H), 1.71-1.76 (m, 2H), 2.22 (s, 3H), 2.31 (s, 3H), 3.91 (t, 2H), 5.03 (s, 2H), 5.83 (dd, 1H), 5.92 (d, 1H), 6.89-7.20 (m, 4H)

EXAMPLE 111

1-(2-chloro-5-trifluoromethyl-benzyl)-4-pentyloxy-1H-pyridin-2-one $^1$H NMR (CDCl$_3$, 300 MHz) δ 0.93 (t, 3H), 1.34-1.46 (m, 4H), 1.74-1.83 (m, 2H), 3.93 (t, 2H), 5.21 (s, 2H), 5.94-6.15 (m, 2H), 7.17 (d, 1H), 7.43-7.54 (m, 3H)

EXAMPLE 112

1-(2-hydroxy-benzyl)-4-pentyloxy-1H-pyridin-2-one $^1$H NMR (CDCl$_3$, 300 MHz) δ 0.91 (t, 3H), 1.29-1.43 (m, 4H), 1.70-1.79 (m, 2H), 3.90 (t, 2H), 4.99 (s, 2H), 5.97 (d, 1H), 6.04 (dd, 1H), 6.83 (t, 1H), 6.95 (dd, 1H), 7.19-7.24 (m, 2H), 7.38 (d, 1H), 10.45 (br s, 1H)

EXAMPLE 113

4-(3-cyclo-propoxy)-1-(2,4-dichloro-benzyl)-1H-pyrimidin-2-one $^1$H NMR (CDCl$_3$, 300 MHz) δ 1.27-1.25 (m, 2H), 1.51-1.82 (m, 9H), 4.37 (t, 2H), 5.10 (s, 2H), 5.85 (d, 1H), 7.22 (d, 1H), 7.38-7.47 (m, 3H)

EXAMPLE 114

1-(2,4-dichloro-benzyl)-4-(3-methyl-pentyloxy)-1H-pyrimidin-2-one $^1$H NMR (CDCl$_3$, 300 MHz) δ 0.85-2.03 (m, 1H), 4.39 (t, 2H), 5.10 (s, 2H), 5.85 (d, 1H), 7.22-7.47 (m, 4H)

EXAMPLE 115

1-(2,4-dichloro-benzyl)-4-hex-4-enyloxy-1H-pyrimidin-2-one $^1$H NMR (CDCl$_3$, 300 MHz) δ 1.25-2.10 (m, 7H), 4.35 (t, 2H), 5.10 (s, 2H), 5.40-5.46 (m, 2H), 5.86 (d, 1H), 7.23-7.47 (m, 4H)

EXAMPLE 116

4-(2-cyclopropyl-ethoxy)-1-(2,4-dichloro-benzyl)-1H-pyrimidin-2-one $^1$H NMR (CDCl$_3$, 300 MHz) δ 0.42-0.96 (m, 3H), 1.25-1.66 (m, 4H), 4.43 (t, 2H), 5.10 (s, 2H), 5.87 (d, 1H), 7.22-7.47 (m, 4H)

EXAMPLE 117

1-(2,4-dichloro-benzyl)-4-(3-methyl-pentyloxy)-1H-pyridin-2-one $^1$H NMR (CDCl$_3$, 300 MHz) δ 0.85-0.91 (m, 6H), 1.17-1.24 (m, 1H), 1.33-1.39 (m, 1H), 1.51-1.58 (m, 2H), 1.78-1.80 (m, 1H), 3.93 (t, 2H), 5.12 (s, 2H), 5.88-5.92 (m, 2H), 7.14-7.20 (m, 3H), 7.38 (s, 1H)

EXAMPLE 118

1-(2,4-dichloro-benzyl)-4-(5-morpholin-4-yl-pentyloxy)-1H-pyridin-2-one $^1$H NMR (CDCl$_3$, 300 MHz) δ 1.46-1.61 (m, 4H), 1.75-1.84 (m, 2H), 2.36 (t, 2H), 2.44 (br s, 4H), 3.73 (t, 4H), 3.92 (t, 2H), 5.14 (s, 2H), 5.90-5.92 (m, 2H), 7.16-7.23 (m, 3H), 7.41 (s, 1H)

EXAMPLE 119

1-(2-chloro-5-methoxy-benzyl)-4-pentyloxy-1H-pyridin-2-one $^1$H NMR (CDCl$_3$, 300 MHz) δ 0.93 (t, 3H), 1.33-1.43 (m, 4H), 1.72-1.79 (m, 2H), 3.74 (s, 3H), 3.91 (t, 2H), 5.15 (s, 2H), 5.88-5.93 (m, 2H), 6.76-6.79 (m, 2H), 7.15 (d, 1H), 7.27 (d, 1H)

EXAMPLE 120

1-(2-chloro-5-ethoxy-benzyl)-4-pentyloxy-1H-pyridin-2-one $^1$H NMR (CDCl$_3$, 300 MHz) δ 0.93 (t 3H), 1.25-1.40 (m, 7H), 1.72-1.81 (m, 2H), 3.89-3.99 (m, 4H), 5.15 (s, 2H), 5.89-5.92 (m, 2H), 6.75-6.77 (m, 2H), 7.15 (d, 1H), 7.26 (d, 1H)

EXAMPLE 121

1-(2-chloro-5-propoxy-benzyl)-4-pentyloxy-1H-pyridin-2-one $^1$H NMR (CDCl$_3$, 300 MHz) δ 0.93 (t, 3H), 1.00 (t, 3H), 1.33-1.43 (m, 4H), 1.70-1.81 (m, 4H), 3.84 (t, 2H), 3.92 (t, 2H), 5.15 (s, 2H), 5.88-5.93 (m, 2H), 6.74-6.78 (m, 2H), 7.15 (d, 1H), 7.26 (d, 1H)

EXAMPLE 122

1-[2-chloro-5-(2-hydroxy-ethoxy)-benzyl]-4-pentyloxy-1H-pyridin-2-one $^1$H NMR (CDCl$_3$, 300 MHz) δ 0.90 (t, 3H), 1.25-1.43 (m, 4H), 1.72-1.79 (m, 2H), 2.13 (t, 1H), 3.91 (t, 4H), 4.01 (t, 2H), 5.15 (s, 2H), 5.86-5.92 (m, 2H), 6.76-6.83 (m, 2H), 7.18 (d, 1H), 7.28 (d, 1H)

EXAMPLE 123

[4-chloro-3-(2-oxo-4-pentyloxy-2H-pyridin-1-ylmethyl)-oxy]-acetonitrile $^1$H NMR (CDCl$_3$, 300 MHz) δ 0.93 (t, 3H), 1.33-1.43 (m, 4H), 1.73-1.82 (m, 2H), 3.92 (t, 2H), 4.71 (s, 2H), 5.16 (s, 2H), 5.92-5.95 (m, 2H), 6.84-6.88 (m, 2H), 7.20 (d, 1H), 7.35 (dd, 1H)

EXAMPLE 124

1-[5-(2-amino-ethoxy)-2-chloro-benzyl]-4-pentyloxy-1H-pyridin-2-one $^1$H NMR (CDCl$_3$, 300 MHz) δ 0.93 (t, 3H) 1.41-1.44 (m, 4H), 1.78-1.82 (m, 2H), 3.93 (t, 2H), 4.01 (t, 4H), 5.17 (s, 2H), 5.96 (d, 1H), 7.13 (dd, 1H), 6.60 (s, 1H), 6.90 (d, 1H), 7.34 (d, 1H), 7.49 (d, 1H)

EXAMPLE 125

N-[2-methyl-3-(2-oxo-4-pentyloxy-2H-pyridin-1-ylmethyl)-phenyl]-acetamide $^1$H NMR (CDCl$_3$, 300 MHz) δ 0.93 (t, 3H), 1.34-1.44 (m, 4H), 1.73-1.82 (m, 2H), 2.07 (s, 3H), 2.22 (s, 3H), 3.92 (t, 2H), 5.05 (s, 2H), 5.89 (dd, 1H), 5.93 (d, 1H), 6.84 (d, 1H), 6.94 (d, 1H), 7.18 (t, 1H), 7.49 (br s, 1H), 7.56 (d, 1H)

EXAMPLE 126

1-(2-methyl-3-methylamino-benzyl)-4-phenyloxy-1H-pyridin-2-one $^1$H NMR (CDCl$_3$, 300 MHz) δ 0.92 (t, 3H), 1.27-1.40 (m, 4H), 1.73-1.78 (m, 2H), 1.98 (s, 3H), 2.90 (s, 3H), 3.69 (br s, 1H), 3.90 (t, 2H), 5.07 (s, 2H), 5.80 (dd, 1H), 5.93 (d, 1H), 6.57 (d, 1H), 6.65 (d, 1H), 6.89 (d, 1H), 7.16 (t, 1H)

EXAMPLE 127

1-(3-dimethylamino-2-methyl-benzyl)-4-phenyloxy-1H-pyridin-2-one $^1$H NMR (CDCl$_3$, 300 MHz) δ 0.93 (t, 3H), 1.36-1.43 (m, 4H), 1.75-1.79 (m, 2H), 2.22 (s, 3H), 2.69 (s, 6H), 3.92 (t, 2H), 5.07 (s, 2H), 5.86 (dd, 1H), 5.95 (d, 1H), 6.72 (d, 1H), 6.93 (d, 1H), 7.05 (d, 1H), 7.15 (t, 1H)

EXAMPLE 128

1-(3-ethylamino-2-methyl-benzyl)-4-pentyloxy-1H-pyridin-2-one $^1$H NMR (CDCl$_3$, 300 MHz) δ 0.92 (t, 3H), 1.31 (t, 3H), 1.33-1.42 (m, 4H), 1.71-1.78 (m, 2H), 1.97 (s, 3H), 3.19 (q, 2H), 3.48 (br s, 1H), 3.90 (t, 2H), 5.06 (s, 2H), 5.79 (dd, 1H), 5.93 (d, 1H), 6.56 (d, 1H), 6.65 (d, 1H), 6.89 (d, 1H), 7.13 (t, 1H)

EXAMPLE 129

1-(3-diethylamino-2-methyl-benzyl)-4-pentyloxy-1H-pyridin-2-one $^1$H NMR (CDCl$_3$, 300 MHz) δ 0.96 (t, 9H), 1.34-1.44 (m, 4H), 1.75-1.80 (m, 2H), 2.21 (s, 3H), 2.95 (q, 4H), 3.92 (t, 2H), 5.08 (s, 2H), 5.87-5.95 (m, 2H), 6.73 (d, 1H), 6.95-7.16 (m, 3H)

EXAMPLE 130

1-(2-methyl-3-propylamino-benzyl)-4-pentyloxy-1H-pyridin-2-one $^1$H NMR (CDCl$_3$, 300 MHz) δ 0.93 (t, 3H), 1.02 (t, 3H), 1.33-1.42 (m, 4H), 1.66-1.80 (m, 4H), 1.97 (s, 3H), 3.12 (t, 2H), 3.57 (br s, 1H), 3.91 (t, 2H), 5.06 (s, 2H), 5.80 (dd, 1H), 5.93 (d, 1H), 6.55 (d, 1H), 6.65 (d, 1H), 6.90 (d, 1H), 7.13 (t, 1H)

EXAMPLE 131

1-(3-dipropylamino-2-methyl-benzyl)-4-pentyloxy-1H-pyridin-2-one $^1$H NMR (CDCl$_3$, 300 MHz) δ 0.83 (t, 6H), 0.93 (t, 3H), 1.34-1.47 (m, 8H), 1.75-1.80 (m, 2H), 2.22 (s, 3H), 2.82-2.87 (m, 4H), 3.93 (t, 2H), 5.07 (s, 2H), 5.87 (dd, 1H), 5.96 (d, 1H), 6.69 (d, 1H), 6.94 (d, 1H), 7.07-7.15 (m, 2H)

EXAMPLE 132

1-[3-(2-hydroxy-ethylamino)-2-methyl-benzyl]-4-pentyloxy-1H-pyridin-2-one $^1$H NMR (CDCl$_3$, 300 MHz) δ 0.92 (t, 3H), 1.32-1.41 (m, 4H), 1.71-1.78 (m, 2H), 1.83 (br s, 1H), 2.01 (s, 3H), 3.34 (t, 2H), 3.90 (t, 4H), 4.02 (br s, 1H), 5.06 (s, 2H), 5.81 (dd, 1H), 5.92 (d, 1H), 6.57 (d, 1H), 6.67 (d, 1H), 6.89 (d, 1H), 7.12 (t, 1H)

EXAMPLE 133

1-(2-chloro-5-methoxy-4-nitro-benzyl)-4-pentyloxy-1H-pyridin-2-one $^1$H NMR (CDCl$_3$, 300 MHz) δ 0.94 (t, 3H), 1.37-1.44 (m, 4H), 1.76-1.81 (m, 2H), 3.91 (s, 3H), 3.93 (t, 2H), 5.20 (s, 2H), 5.93 (d, 1H), 5.97 (dd, 1H), 7.18 (s, 1H), 7.26 (d, 1H), 7.93 (s, 1H)

EXAMPLE 134

1-(4-amino-2-chloro-5-methoxy-benzyl)-4-pentyloxy-1H-pyridin-2-one $^1$H NMR (CDCl$_3$, 300 MHz) δ 0.92 (t, 3H), 1.32-1.42 (m, 4H), 1.71-1.78 (m, 2H), 3.81 (t, 3H), 3.87-3.93 (m, 4H), 5.09 (s, 2H), 5.85 (dd, 1H), 5.90 (d, 1H), 6.69 (s, 1H), 6.91 (s, 1H), 7.21 (d, 1H)

EXAMPLE 135

N-[5-chloro-2-methoxy-4-(2-oxo-4-pentyloxy-2H-pyridin-1-ylmethyl)-phenyl]-acetamide $^1$H NMR (CDCl$_3$, 300 MHz) δ 0.92 (t, 3H), 1.35-1.42 (m, 4H), 1.74-1.78 (m, 2H), 2.21 (s, 3H), 3.84 (s, 3H), 3.90 (t, 2H), 5.15 (s, 2H), 5.88-5.93 (m, 2H), 7.04 (s, 1H), 7.29 (d, 1H), 7.77 (br s, 1H), 8.46 (s, 1H)

EXAMPLE 136

1-(2-chloro-5-methoxy-4-methylamino-benzyl)-4-pentyloxy-1H-pyridin-2-one $^1$H NMR (CDCl$_3$, 300 MHz) δ 0.93 (t, 3H), 1.30-1.43 (m, 4H), 1.70-1.77 (m, 2H), 2.85 (s, 3H), 3.81 (s, 3H), 3.92 (t, 2H), 4.95 (s, 2H), 5.89-6.03 (m, 2H), 6.53 (s, 1H), 6.89 (s, 1H), 7.28 (d, 1H)

EXAMPLE 137

1-(2-chloro-4-dimethylamino-5-methoxy-benzyl)-4-pentyloxy-1H-pyridin-2-one $^1$H NMR (CDCl$_3$, 300 MHz) δ 0.95 (t, 3H), 1.40-1.44 (m, 4H), 1.75-1.81 (m, 2H), 2.76 (s, 6H), 3.80 (s, 3H), 3.99 (t, 2H), 5.14 (s, 2H), 5.95 (d, 1H), 6.10 (dd, 1H), 6.85 (s, 1H), 7.00 (s, 1H), 7.47 (d, 1H)

EXAMPLE 138

1-(2-chloro-4-ethylamino-5-methoxy-benzyl)-4-pentyloxy-1H-pyridin-2-one $^1$H NMR (CDCl$_3$, 300 MHz) δ 0.92 (t, 3H), 1.28 (t, 3H), 1.36-1.41 (m, 4H), 1.71-1.77 (m, 2H), 3.13 (t, 2H), 3.80 (s, 3H), 3.89 (t, 2H), 4.23 (br s, 1H), 5.10 (s, 2H), 5.84 (dd, 1H), 5.90 (d, 1H), 6.52 (s, 1H), 6.87 (s, 1H), 7.22 (d, 1H)

EXAMPLE 139

1-(2-chloro-5-methoxy-4-propylamino-benzyl)-4-pentyloxy-1H-pyridin-2-one $^1$H NMR (CDCl$_3$, 300 MHz) δ 0.92 (t, 3H), 1.00 (t, 3H), 1.34-1.41 (m, 4H), 1.62-1.77 (m, 4H), 3.05 (t, 2H), 3.80 (s, 3H), 3.89 (t, 2H), 4.31 (br s, 1H), 5.09 (s, 2H), 5.83 (dd, 1H), 5.89 (d, 1H), 6.51 (s, 1H), 6.86 (s, 1H), 7.21 (d, 1H)

EXAMPLE 140

1-[2-chloro-4-(2-hydroxy-ethylamino)-5-methoxy-benzyl]-4-pentyloxy-1H-pyridin-2-one $^1$H NMR (CDCl$_3$, 300 MHz) δ 0.92 (t, 3H), 1.32-1.42 (m, 4H), 1.70-1.77 (m, 2H), 1.96 (br s, 1H), 3.30 (t, 2H), 3.79 (s, 3H), 3.82-3.91 (m, 4H), 4.73 (br s, 1H), 5.09 (s, 2H), 5.85 (dd, 1H), 5.90 (d, 1H), 6.57 (s, 1H), 6.88 (s, 1H), 7.21 (d, 1H)

EXAMPLE 141

1-(4-amino-6-chloro-3-methoxy-2-nitro-benzyl)-4-pentyloxy-1H-pyridin-2-one $^1$H NMR (CDCl$_3$, 300 MHz) δ 0.91 (t, 3H), 1.28-1.41 (m, 4H), 1.69-1.79 (m, 2H), 3.84 (s, 3H), 3.88 (t, 2H), 4.35 (br s, 2H), 4.96 (s, 2H), 5.82-5.85 (m, 2H), 6.92-7.02 (m, 2H)

EXAMPLE 142

1-(2,4-diamino-6-chloro-3-methoxy-benzyl)-4-pentyloxy-1H-pyridin-2-one $^1$H NMR (CDCl$_3$, 300 MHz) δ 0.92 (t, 3H), 1.30-1.39 (m, 4H), 1.73-1.77 (m, 2H), 3.69 (s, 3H), 3.79 (br s, 2H), 3.89 (t, 2H), 5.16 (s, 2H), 5.30 (br s, 2H), 5.88-5.94 (m, 2H), 6.17 (s, 1H), 7.56 (d, 1H)

EXAMPLE 143

1-(2,5-dichloro-6-methoxy-pyrimidin-4-ylmethyl)-4-pentyloxy-1H-pyridin-2-one

H NMR (CDCl$_3$, 300 MHz) δ 0.93 (t 3H), 1.34-1.45 (m, 4H), 1.73-1.82 (m, 2H), 3.92 (t, 2H), 4.08 (s, 3H), 5.14 (s, 2H), 5.86 (d, 1H), 5.96 (dd, 1H), 7.19 (d, 1H)

EXAMPLE 144

1-(2,4-dichloro-benzenesulfonyl)-4-pentyloxy-1H-pyridin-2-one $^1$H NMR (CDCl$_3$, 300 MHz) δ 0.90 (t, 3H), 1.32-1.40 (m, 4H), 1.72-1.79 (m, 2H), 3.89 (t, 2H), 5.60 (d, 1H), 6.05 (dd, 1H), 7.47-7.51 (m, 2H), 7.95 (d, 1H), 8.35 (d, 1H)

EXAMPLE 145

1-(4-methanesulfonyl-benzyl)-4-pentyloxy-1H-pyridin-2-one $^1$H NMR (CDCl$_3$, 300 MHz) δ 0.94 (t, 3H), 1.34-1.45 (m, 4H), 1.74-1.83 (m, 2H), 3.04 (s, 3H), 3.94 (t, 2H), 5.22 (s, 2H), 5.93 (d, 1H), 5.99 (dd, 1H), 7.20 (d, 1H), 7.32 (d, 1H), 7.76 (dd, 1H), 7.97 (d, 1H)

EXAMPLE 146

1-(4-amino-2-chloro-5-hydroxy-benzyl)-4-pentyloxy-1H-pyridin-2-one $^1$H NMR (CDCl$_3$, 300 MHz) δ 0.91 (t, 3H), 1.29-1.41 (m, 4H), 1.66-1.75 (m, 2H), 3.78 (t, 2H), 5.13 (s, 2H), 5.85 (d, 1H), 5.94 (dd, 1H), 6.68 (s, 1H), 7.18 (s, 1H), 7.44 (d, 1H)

EXAMPLE 147

4-(4-bromo-butoxy)-1-(2,4-dichloro-benzyl)-1H-pyridin-2-one $^1$H NMR (CDCl$_3$, 300 MHz) δ 10.88-2.08 (m, 4H), 3.46 (t, 2H), 3.95 (t, 2H), 5.13 (s, 2H), 5.88-5.92 (m, 2H), 7.16-7.24 (m, 3H), 7.40 (s, 1H)

EXAMPLE 148

4-[1-(2,4-dichloro-benzyl)-2-oxo-1,2-dihydro-pyridin-4-yloxy]-butylammonium $^1$H NMR (CD$_3$OD, 300 MHz) δ 1.82-1.90 (m, 4H), 3.00 (t, 2H), 4.07 (t, 2H), 5.19 (s, 2H), 5.97 (s, 1H), 6.14 (dd, 1H), 7.05 (d, 1H), 7.31 (dd, 1H), 7.53-7.57 (m, 2H)

EXAMPLE 149

1-(5-chloro-2,6-dimethoxy-pyrimidin-4-ylmethyl)-4-pentyloxy-1H-pyridin-2-one $^1$H NMR (CDCl$_3$, 300 MHz) δ 0.93 (t, 3H), 1.32-1.40 (m, 4H), 1.73-1.80 (m, 2H), 3.80 (s, 3H), 3.91 (t, 2H), 4.04 (s, 3H), 5.15 (s, 2H), 5.89 (d, 1H), 5.93 (dd, 1H), 7.16 (d, 1H)

EXAMPLE 150

1-(2-amino-5-chloro-6-methoxy-pyrimidin-4-ylmethyl)-4-pentyloxy-1H-pyridin-2-one $^1$H NMR (CDCl$_3$, 300 MHz) δ 0.93 (t, 3H), 1.32-1.43 (m, 4H), 1.73-1.80 (m, 2H), 3.92 (t, 2H), 3.95 (s, 3H), 4.81 (br s, 2H), 5.08 (s, 2H), 5.90-5.93 (m, 2H), 7.10 (d, 1H)

EXAMPLE 151

1-(6-amino-2,5-dichloro-pyrimidin-4-ylmethyl)-4-pentyloxy-1H-pyridin-2-one $^1$H NMR (CDCl$_3$, 300 MHz) δ 0.95(t, 3H), 1.31-1.44 (m, 4H), 1.73-1.79 (m, 2H), 3.91 (t, 2H), 5.08 (s, 2H), 5.60 (br s, 2H), 5.86 (d, 1H), 5.95 (dd, 1H), 7.22 (d, 1H)

EXAMPLE 152

5-chloro-6-(2-oxo-4-pentyloxy-2H-pyridin-1-ylmethyl)-3H-benzoxazole-2-one $^1$H NMR (CDCl$_3$, 300 MHz) δ 0.94 (t, 3H), 1.38-1.46 (m, 4H), 1.76-2.05 (m, 2H), 3.97 (t, 2H), 5.11 (s, 2H), 6.01-6.07 (m, 2H), 6.72 (s, 1H), 6.73 (s, 1H), 7.22 (d, 1H), 9.35 (br s, 1H)

EXAMPLE 153

1-(2-chloro-4-hydroxy-benzyl)-4-pentyloxy-1H-pyridin-2-one $^1$H NMR (CDCl$_3$, 300 MHz) δ 0.92 (t, 3H), 1.30-1.41 (m, 4H), 1.70-1.80 (m, 2H), 3.90 (t, 2H), 5.09 (s, 2H), 5.94-6.01 (m, 2H), 6.60 (dd, 1H), 6.88 (d, 1H), 7.00 (d, 1H), 7.28 (d, 1H), 9.75 (br s, 1H)

EXAMPLE 154

1-(2-chloro-4-isopropoxy-benzyl)-4-pentyloxy-1H-pyridin-2-one $^1$H NMR (CDCl$_3$, 300 MHz) δ 0.92 (t, 3H), 1.31 (d, 6H), 1.35-1.45 (m, 4H), 1.73-1.80 (m, 2H), 3.90 (t, 2H), 4.46-4.54 (m, 1H), 5.11 (s, 2H), 5.85-5.91 (m, 2H), 6.74 (dd, 1H), 6.91 (d, 1H), 7.16 (d 1H), 7.23 (d, 1H)

EXAMPLE 155

2-[3-(2-oxo-4-pentyloxy-2H-pyridin-1-yl)-propyl]-isoindole-1,3-dione $^1$H NMR (CDCl$_3$, 300 MHz) δ 0.93 (t, 3H), 1.20-1.33 (m, 4H), 1.71-1.80 (m, 2H), 2.09-2.18 (m, 2H), 3.75 (t, 2H), 3.87-3.94 (m, 4H), 5.86 (d, 1H), 5.91 (dd, 1H), 7.27 (s, 1H), 7.72-7.76 (m, 2H), 7.83-7.87 (m, 2H)

EXAMPLE 156

1-(3-amino-propyl)-4-pentyloxy-1H-pyridin-2-one $^1$H NMR (CDCl$_3$, 300 MHz) δ 0.93 (t, 3H), 1.36-1.44 (m, 4H), 1.75-1.80 (m, 2H), 2.26-2.30 (m, 2H), 3.00 (t, 2H), 3.91 (t, 2H), 4.10 (t, 2H), 5.90 (d, 1H), 6.02 (d, 1H), 7.25 (d, 1H)

EXAMPLE 157

N-[3-(2-oxo-4-pentyloxy-2H-pyridin-1-yl)-propyl]-acetamide $^1$H NMR (CDCl$_3$, 300 MHz) δ 0.93 (t, 3H), 1.34-1.44 (m, 4H), 1.73-1.89 (m, 4H), 2.01 (s, 3H), 3.15-3.21 (m, 2H), 3.92 (t, 2H), 3.98 (t, 2H), 5.89 (d, 1H), 5.98 (dd, 1H), 7.08 (br s, 1H), 7.14 (d, 1H)

EXAMPLE 158

1-(3-dimethylamino-propyl)-4-pentyloxy-1H-pyridin-2-one $^1$H NMR (CDCl$_3$, 300 MHz) δ 0.93 (t, 3H), 1.37-1.42 (m, 4H), 1.72-1.78 (m, 4H), 2.31-2.39 (m, 2H), 3.16-3.20 (m, 2H), 3.40 (s, 6H), 3.90 (t, 2H), 4.11 (t, 2H), 5.84 (s, 1H), 5.97 (d, 1H), 7.55 (d, 1H)

EXAMPLE 159

1-(2,4-dichloro-benzyl)-6-methyl-4-pentyloxy-1H-pyridin-2-one $^1$H NMR (CDCl$_3$, 300 MHz) δ 0.93 (t, 3H), 1.34-1.44 (m, 4H), 1.73-1.92 (m, 2H), 2.13 (s, 3H), 3.93 (t, 2H), 5.28 (d, 2H), 5.82 (d, 1H), 5.88 (d, 1H), 6.72 (d, 1H), 7.13 (d, 1H), 7.40 (d, 1H)

EXAMPLE 160

1-(2,4-dichloro-benzyl)-6-methyl-3-pentyl-4-pentyloxy-1H-pyridin-2-one $^1$H NMR (CDCl$_3$, 300 MHz) δ 0.85-0.98 (m, 6H), 1.30-1.48 (m, 10H), 1.75-1.78 (m, 2H), 2.18 (s, 3H), 2.55 (t, 2H), 3.99 (t, 2H), 5.33 (s, 2H), 5.94 (s, 1H), 6.65 (d, 1H), 7.12 (dd, 1H), 7.39 (d, 1H)

EXAMPLE 161

1-(2-amino-ethyl)-4-pentyloxy-1H-pyridin-2-one $^1$H NMR (CDCl$_3$+a few drop of CD$_3$OD, 300 MHz) δ 0.93 (t, 3H), 1.31-1.40 (m, 4H), 1.75-1.79 (m, 2H), 2.95 (t, 2H), 3.81-4.00 (m, 4H), 5.83-5.91 (m, 2H), 7.08 (d, 1H)

EXAMPLE 162

N-[2-(2-oxo-4-pentyloxy-2H-pyridin-1-yl)-ethyl]-acetamide $^1$H NMR (CDCl$_3$, 300 MHz) δ 0.92 (t, 3H) 1.31-1.42 (m, 4H), 1.72-1.79 (m, 2H), 1.96 (s, 3H), 3.53 (q, 2H), 3.90 (t, 2H), 4.05 (t, 2H), 5.87 (d, 1H), 5.94 (dd, 2H), 6.89 (br s, 1H), 7.13 (d, 1H)

EXAMPLE 163

N-[1,1-dimethyl-2-(2-oxo-4-pentyloxy-2H-pyridin-1-yl)-ethyl]-methanesulfonamide $^1$H NMR (CDCl$_3$, 300 MHz) δ 0.93 (t, 3H), 1.29-1.46 (m, 10H), 1.75-1.80 (m, 2H), 2.98 (s, 3H), 3.92 (t, 2H), 3.99 (s, 2H), 5.91-5.97 (m, 2H), 6.56 (br s, 1H), 7.23 (d, 1H)

EXAMPLE 164

N-[1-(2-oxo-4-pentyloxy-2H-pyridin-1-ylmethyl)-propyl]-methanesulfonamide $^1$H NMR (CDCl$_3$, 300 MHz) δ 0.93 (t, 3H), 1.05 (t, 3H), 1.30-1.40 (m, 4H), 1.59-1.81 (m, 4H), 2.75 (s, 3H), 3.65-4.15 (m, 6H), 5.75 (d, 1H), 5.91 (d, 1H), 5.97 (dd, 1H), 7.19 (d, 1H)

EXAMPLE 165

1-(7-nitro-benzo[1,3]dioxol-5-ylmethyl)-4-pentyloxy-1H-pyridin-2-one $^1$H NMR (CDCl$_3$, 300 MHz) δ 0.95 (t, 3H), 1.32-1.42 (m, 4H), 1.75-1.82 (m, 2H), 3.95 (t, 2H), 5.42 (s, 2H), 5.94-6.00 (m, 2H), 6.09 (s, 2H), 6.55 (s, 1H), 7.18 (d, 1H), 7.63 (s, 1H)

EXAMPLE 166

1-(2-chloro-3-nitro-benzyl)-4-pentyloxy-1H-pyridin-2-one $^1$H NMR (CDCl$_3$, 300 MHz) δ 0.97 (t, 3H), 1.27-1.53 (m, 4H), 1.77-1.82 (m, 2H), 3.95 (t, 2H), 5.25 (s, 2H), 5.96-6.00 (m, 2H), 7.22 (d, 1H), 7.35-7.44 (m, 2H), 7.73 (d, 1H)

EXAMPLE 167

1-(3-amino-2-chloro-benzyl)-4-pentyloxy-1H-pyridin-2-one $^1$H NMR (CDCl$_3$, 300 MHz) δ 0.91 (t, 3H), 1.37-1.43 (m, 4H), 1.72-1.76 (m, 2H), 3.89 (t, 2H), 4.13 (br s), 5.12 (s, 2H), 5.86-5.92 (m, 2H), 6.47 (d, 1H), 6.70 (d, 1H), 6.96-7.07 (m, 2H)

EXAMPLE 168

N-[2-chloro-3-(2-oxo-4-pentyloxy-2H-pyridin-1-ylmethyl)-phenyl]-acetamide $^1$H NMR (CDCl$_3$, 300 MHz) δ 0.94 (t, 3H), 1.27-1.44 (m, 4H), 1.74-1.81 (m, 2H), 2.26 (s, 3H), 3.93 (t, 2H), 5.19 (s, 2H), 5.90-5.94 (m, 2H), 6.87 (d, 1H), 7.06 (d, 1H), 7.23 (d, 1H), 7.69 (br s, 1H), 8.30 (d, 1H)

EXAMPLE 169

N-[2,chloro-3-(2-oxo-4-pentyloxy-2H-pyridin-1-ylmethyl)-phenyl]-methanesulfonamide $^1$H NMR (CDCl$_3$, 300 MHz) δ 0.94 (t, 3H), 1.37-1.43 (m, 4H), 1.75-1.81 (m, 2H), 3.03 (s, 3H), 3.94 (t, 2H), 5.18 (s, 2H), 5.94-5.97 (m, 2H), 6.90 (d, 1H), 7.00 (br s, 1H), 7.12 (d, 1H), 7.28 (d, 1H), 7.60 (d, 1H)

EXAMPLE 170

N,N'-[2-chloro-3-(2-oxo-4-pentyloxy-2H-pyridin-1-ylmethyl)-phenyl]-dimethanesulfonamide $^1$H NMR (CDCl$_3$, 300 MHz) δ 0.94 (t, 3H), 1.26-1.41 (m, 4H), 1.76-1.81 (m, 2H), 3.49 (s, 6H), 3.94 (t, 2H), 5.23 (s, 2H), 5.94-5.96 (m, 2H), 7.15 (d, 1H), 7.25-7.38 (m, 3H)

EXAMPLE 171

1-[2-chloro-3-(2-hydroxy-ethylamino)-benzyl]-4-pentyloxy-1H-pyridin-2-one $^1$H NMR (CDCl$_3$, 300 MHz) δ 0.93 (t, 3H), 1.28-1.38 (m, 4H), 1.74-1.79 (m, 2H), 2.00 (br s, 1H), 3.37 (br s, 2H), 3.89-3.94 (m, 4H), 4.74 (br s, 1H), 5.15 (s, 2H), 5.87 (dd, 1H), 5.93 (d, 1H), 6.48 (d, 1H), 6.66 (d, 1H), 7.05-7.12 (m, 2H)

EXAMPLE 172

4-chloro-2-(2-chloro-benzyl)-5-pentyloxy-2H-pyridazin-3-one $^1$H NMR (CDCl$_3$, 300 MHz) δ 0.91 (t, 3H), 1.30-1.47 (m, 4H), 1.70-1.79 (m, 2H), 4.59 (t, 2H), 5.43 (s, 2H), 7.07-7.10 (m, 1H), 7.18-7.26 (m, 2H), 7.38 (dd, 1H), 7.74 (s, 1H)

EXAMPLE 173

2-(2-chloro-benzyl)-5-pentyloxy-2H-pyridazin-3-one $^1$H NMR (CDCl$_3$, 300 MHz) δ 0.93 (t, 3H), 1.26-1.49 (m, 4H), 1.85-1.94 (m, 2H), 3.99 (t, 2H), 5.49 (s, 2H), 6.38 (d, 1H), 7.16-7.39 (m, 4H), 7.67 (d, 1H)

EXAMPLE 174

1-(3-amino-2,6-dichloro-benzyl)-4-pentyloxy-1H-pyridin-2-one $^1$H NMR (CDCl$_3$, 300 MHz) δ 0.92 (t, 3H), 1.25-1.44 (m, 4H), 1.70-1.80 (m, 2H), 3.90 (t, 2H), 4.19 (s, 2H), 5.33 (s, 2H), 5.79 (dd, 1H), 5.92 (d, 1H), 6.74 (dd, 2H), 7.18 (d, 1H)

EXAMPLE 175

1-(3-benzyloxy-2-chloro-4-methoxy-benzyl)-4-pentyloxy-1H-pyridin-2-one $^1$H NMR (CDCl$_3$, 300 MHz) δ 0.91 (t, 3H), 1.35-1.43 (m, 4H), 1.72-1.79 (m, 2H), 3.84 (s, 3H), 3.90 (t, 2H), 5.02 (s, 2H), 5.12 (s, 2H), 5.84-5.91 (m, 2H), 6.79 (d, 1H), 7.01 (d, 1H), 7.11 (d, 1H), 7.33-7.40 (m, 3H), 7.49-7.54 (m, 2H)

EXAMPLE 176

1-(2-chloro-3,4-dimethoxy-benzyl)-4-pentyloxy-1H-pyridin-2-one $^1$H NMR (CDCl$_3$, 300 MHz) δ 0.94 (t, 3H), 1.27-1.41 (m, 4H), 1.74-1.80 (m, 2H), 3.86-3.94 (m, 8H), 5.13 (s, 2H), 5.87-5.92 (m, 2H), 6.80 (d, 1H), 7.03 (d, 1H), 7.18 (d, 1H)

EXAMPLE 177

1-(2-chloro-3-hydroxy-4-methoxy-benzyl)-4-pentyloxy-1H-pyridin-2-one $^1$H NMR (CDCl$_3$, 300 MHz) δ 0.95 (t, 3H), 1.26-1.39 (m, 4H), 1.73-1.76 (m, 2H), 3.89-3.93 (m, 5H), 5.13 (s, 2H), 5.86-5.90 (m, 2H), 6.75 (d, 1H), 6.83 (d, 1H), 7.13 (d, 1H)

EXAMPLE 178

1-[2-chloro-4-methoxy-3-(2-methoxy-ethoxy)-benzyl]-4-pentyloxy-1H-pyridin-2-one $^1$H NMR (CDCl$_3$, 300 MHz) δ 0.92 (t, 3H), 1.26-1.39 (m, 4H), 1.74-1.82 (m, 2H), 3.45 (s, 3H), 3.74 (t, 2H), 3.84 (s, 3H), 3.91 (t, 2H), 4.15 (t, 2H), 5.12 (s, 2H), 5.86-5.91 (m, 2H), 6.78 (d, 1H), 7.00 (d, 1H), 7.15 (d, 1H)

EXAMPLE 179

1-[2-chloro-4-methoxy-3-(2-pyrrolidin-1-yl-ethoxy)-benzyl]-4-pentyloxy-1H-pyridin-2-one $^1$H NMR (CDCl$_3$, 300 MHz) δ 0.93 (t, 3H), 1.33-1.39 (m, 4H), 1.77-1.84 (m, 6H), 2.71 (m, 4H), 2.97 (t, 2H), 3.83 (s, 3H), 3.91 (t, 2H), 4.13 (t, 2H), 5.12 (s, 2H), 5.86-5.92 (m, 2H), 6.78 (d, 1H), 7.00 (d, 1H), 7.15 (d, 1H)

EXAMPLE 180

1-[2-chloro-3-(2-dimethylamino-ethoxy)-4-methoxy-benzyl]-4-pentyloxy-1H-pyridin-2-one $^1$H NMR (CDCl$_3$, 300 MHz) δ 0.94 (t, 3H), 1.33-1.42 (m, 4H), 1.75-1.82 (m, 2H), 2.41 (s, 6H), 2.83 (t, 2H), 3.97 (t, 2H), 4.11 (t, 2H), 5.13 (s, 2H), 5.94 (s, 1H), 6.04 (dd, 1H), 6.87 (dd, 1H), 6.94 (dd, 1H), 7.27 (d, 1H)

EXAMPLE 181

2-{3-[2-chloro-6-methoxy-3-(2-oxo-4-pentyloxy-2H-pyridin-1-ylmethyl)-phenoxy]-propyl}-isoindole-1,3-dione $^1$H NMR (CDCl$_3$, 300 MHz) δ 0.92 (t, 3H), 1.28-1.38 (m, 4H), 1.73-1.77 (m, 2H), 3.59 (s, 3H), 3.89 (t, 2H), 4.12 (t, 2H), 4.26 (t, 2H), 5.03 (s, 2H), 5.85-5.91 (m, 2H), 6.69 (d, 1H), 6.95 (d, 1H), 7.08 (d, 1H), 7.74 (d, 2H), 7.87 (d, 2H)

EXAMPLE 182

1-[3-(2-dimethylamino-ethoxy)-2-methyl-benzyl]-4-pentyloxy-1H-pyridin-2-one $^1$H NMR (CDCl$_3$, 300 MHz) δ 0.94 (t, 3H), 1.26-1.35 (m, 4H), 1.75-1.79 (m, 2H), 2.15 (s, 3H), 2.37 (s, 6H), 2.79 (t, 2H), 3.93 (t, 2H), 4.09 (t, 2H), 5.08 (s, 2H), 5.83-5.94 (m, 2H), 6.70 (d, 1H), 6.83-6.92 (m, 2H), 7.15 (t, 1H), 7.28 (s, 1H)

EXAMPLE 183

1-[2-chloro-3-(2-dimethylamino-ethylamino)-benzyl]-4-pentyloxy-1H-pyridin-2-one $^1$H NMR (CDCl$_3$, 300 MHz) δ 0.93 (t, 3H), 1.30-1.40 (m, 4H), 1.55-1.59 (m, 2H), 2.29 (s, 6H), 2.62 (t, 2H), 3.20 (t, 2H), 3.92 (t, 2H), 5.00 (br s, 1H), 5.16 (s, 2H), 5.86-5.93 (m, 2H), 6.47 (d, 1H), 6.61 (d, 1H), 7.06-7.13 (m, 2H)

EXAMPLE 184

1-[2,6-dichloro-3-(2-hydroxy-ethylamino)-benzyl]-4-pentyloxy-1H-pyridin-2-one $^1$H NMR (CDCl$_3$, 300 MHz) δ 0.91 (t, 3H), 1.32-1.42 (m, 4H), 1.72-1.79 (m, 2H), 2.54 (t, 1H), 3.36 (q, 2H), 3.87-3.94 (m, 4H), 4.84 (t, 1H), 5.27 (s, 2H), 5.78 (dd, 1H), 5.91 (d, 1H), 6.68-6.71 (m, 2H), 7.23 (d, 1H)

EXAMPLE 185

1-[2,6-dichloro-3-(2-dimethylamino-ethylamino)-benzyl]-4-pentyloxy-1H-pyridin-2-one $^1$H NMR (CD$_3$OD, 300 MHz) δ 0.93 (t 3H), 1.38-1.46 (m, 4H), 1.75-1.80 (m, 2H), 2.55 (s, 6H), 2.91 (t, 2H), 3.46 (t, 2H), 3.99 (t, 2H), 5.32 (s, 2H), 5.96 (d, 1H), 6.02 (dd, 1H), 6.88 (d, 1H), 6.93 (d, 1H), 7.35 (d, 1H)

EXAMPLE 186

1-[2,6-dichloro-3-(3-hydroxy-propylamino)-benzyl]-4-pentyloxy-1H-pyridin-2-one $^1$H NMR (CD$_3$OD, 300 MHz) δ 0.93 (t, 3H), 1.38-1.45 (m, 4H), 1.75-1.90 (m, 4H), 3.48-3.53 (m, 2H), 3.69 (t, 2H), 3.98 (t, 2H), 5.31 (s, 2H), 5.95 (d, 1H), 6.01 (dd, 1H), 6.83 (d, 1H), 6.90 (d, 1H), 7.30 (d, 1H)

EXAMPLE 187

1-[2,6-dichloro-3-(3-dimethylamino-propylamino)-benzyl]-4-pentyloxy-1H-pyridin-2-one $^1$H NMR (CDCl$_3$+a few drop of CD$_3$OD, 300 MHz) δ 0.79 (t, 3H), 1.13-1.30 (m, 4H), 1.61-1.77 (m, 4H), 2.20 (s, 6H), 2.38 (t, 2H), 3.11 (t, 2H), 3.80 (t, 2H), 5.18 (s, 2H), 5.76 (dd, 1H), 5.81 (d, 1H), 6.54 (d, 1H), 6.64 (d, 1H), 7.13 (d, 1H)

EXAMPLE 188

1-[3-(3-amino-propylamino)-2,6-dichloro-benzyl]-4-pentyloxy-1H-pyridin-2-one $^1$H NMR (CD$_3$OD, 300 MHz) δ 0.94 (t, 3H), 1.38-1.46 (m, 4H), 1.75-1.80 (m, 2H), 1.94-2.01 (m, 2H), 3.01-3.06 (m, 2H), 3.32-3.39 (m, 2H), 3.99 (t, 2H), 5.31 (s, 2H), 5.95 (d, 1H), 6.02 (dd, 1H), 6.87 (d, 1H), 6.92 (d, 1H), 7.33 (d, 1H)

EXAMPLE 189

1-(3-fluoro-2-methyl-benzyl)-4-pentyloxy-1H-pyridin-2-one $^1$H NMR (CDCl$_3$, 300 MHz) δ 0.93 (t, 3H), 1.32-1.46 (m, 4H), 1.75-1.78 (m, 2H), 2.19 (s, 3H), 3.93 (t, 2H), 5.08 (s, 2H), 5.86-5.94 (m, 2H), 6.82 (d, 1H), 6.92-7.02 (m, 2H), 7.10-7.15 (m, 1H)

EXAMPLE 190

1-(2-chloro-3-dimethylaminomethyl-4-fluoro-benzyl)-4-pentyloxy-1H-pyridin-2-one $^1$H NMR (CDCl$_3$, 300 MHz) δ 0.92 (t, 3H), 1.33-1.45 (m, 4H), 1.72-1.86 (m, 2H), 3.55 (s, 6H), 3.91 (t, 2H), 4.91 (s, 2H), 5.19 (s, 2H), 5.88 (d, 1H), 5.98 (dd, 1H), 7.12-7.42 (m, 3H)

EXAMPLE 191

1-(2,6-dichloro-3-methylamino-benzyl)-4-pentyloxy-1H-pyridin-2-one $^1$H NMR (CDCl$_3$, 300 MHz) δ 0.92 (t, 3H), 1.32-1.42 (m, 4H), 1.75-1.79 (m, 2H), 2.91 (d, 3H), 3.90 (t, 2H), 4.49 (q, 1H), 5.33 (s, 2H), 5.78 (dd, 1H), 5.92 (d, 1H), 6.63 (d, 1H), 6.70 (d, 1H), 7.28 (d, 1H)

EXAMPLE 192

1-(2,6-dichloro-3-dimethylamino-benzyl)-4-pentyloxy-1H-pyridin-2-one $^1$H NMR (CDCl$_3$, 300 MHz) δ 0.92 (t, 3H), 1.34-1.41 (m, 4H), 1.72-1.78 (m, 2H), 2.80 (s, 6H), 3.90 (t, 2H), 5.38 (s, 2H), 5.79 (dd, 1H), 5.93 (d, 1H), 6.69 (d, 1H), 7.08 (d, 1H), 7.33 (d, 1H)

EXAMPLE 193

[2-chloro-3-(2-oxo-4-pentyloxy-2H-pyridin-1-ylmethyl)-phenylamino]-acetic acid $^1$H NMR (DMSO-d$_6$, 300 MHz) δ 0.89 (t, 3H), 1.32-1.37 (m, 4H), 1.67-1.71 (m, 2H), 3.90-3.97 (m, 4H), 5.03 (s, 2H), 5.69 (br s, 1H), 5.83 (s, 1H), 5.99 (d, 1H), 6.05 (d, 1H), 6.52 (d, 1H), 7.05 (t, 1H), 7.51 (d, 1H)

EXAMPLE 194

1-(6-chloro-benzo[1,3]dioxol-5-ylmethyl)-4-(pyridin-4-ylmethoxy)-1H-pyridin-2-one $^1$H NMR (CDCl$_3$, 300 MHz) δ 5.02 (s, 2H), 5.09 (s, 2H), 5.95-6.01 (m, 4H), 6.84 (d, 1H) 7.21-7.31 (m, 4H), 8.62 (d, 2H)

EXAMPLE 195

1-(6-chloro-benzo[1,3]dioxol-5-ylmethyl)-4-(6-chloro-pyridin-3-ylmethoxy)-1H-pyridin-2-one $^1$H NMR (CDCl$_3$, 300 MHz) δ 4.98 (s, 2H), 5.09 (s, 2H), 5.92-5.99 (m, 4H), 6.83 (d, 1H), 7.22-7.40 (m, 3H), 7.70 (dd, 1H), 8.40 (dd, 1H)

EXAMPLE 196

1-(6-chloro-benzo[1,3]dioxol-5-ylmethyl)-4-(4-methoxy-3,5-dimethylpyridin-2-ylmethoxy)-1H-pyridin-2-one $^1$H NMR (CDCl$_3$, 300 MHz) δ 2.27 (s, 6H), 3.78 (s, 3H), 5.09 (s, 4H), 6.09-6.10 (m, 4H), 6.84 (s, 2H), 7.17 (s, 1H), 7.21 (s, 1H), 8.25 (s, 1H)

EXAMPLE 197

1-(6-chloro-benzo[1,3]dioxol-5-ylmethyl)-4-(2-methyl-pyridin-3-ylmethoxy)-1H-pyridin-2-one $^1$H NMR (CDCl$_3$, 300 MHz) δ 2.58 (s, 3H), 5.00 (s, 2H), 5.13 (s, 2H), 5.96-5.98 (m, 3H), 6.05 (d, 1H), 6.87 (d, 2H), 7.19 (dd, 1H), 7.25-7.29 (m, 1H), 7.67 (d, 1H), 8.51 (d, 1H)

EXAMPLE 198

1-(6-chloro-benzo[1,3]dioxol-5-ylmethyl)-4-(thiazol-4-ylmethoxy)-1H-pyridin-2-one $^1$H NMR (CDCl$_3$, 300 MHz) δ 5.12 (s, 2H), 5.21 (s, 2H), 5.98 (s, 2H) 6.01 (dd, 1H), 6.07 (d, 1H), 6.86 (d, 2H), 7.24 (d, 1H), 7.43 (s, 1H), 8.87 (s, 1H)

EXAMPLE 199

1-(6-chloro-benzo[1,3]dioxol-5-ylmethyl)-4-(pyridin-2-ylmethoxy)-1H-pyridin-2-one $^1$H NMR (CDCl$_3$, 300 MHz) δ 5.12 (s, 2H) 5.16 (s, 2H), 5.98 (s, 2H), 6.03-6.05 (m, 2H), 6.86 (d, 2H), 7.25-7.29 (m, 2H), 7.45 (d, 1H), 7.75 (td, 1H), 8.63 (d, 1H)

EXAMPLE 200 pentanoic acid 1-(6-chloro-benzo[1,3]dioxol-5-ylmethyl)-2-oxo-1,2-dihydro-pyridin-4-yl ester H NMR (CDCl$_3$, 300 MHz) δ 0.97 (t 3H), 1.39-1.47 (m, 2H), 1.68-1.75 (m, 2H), 2.54 (t, 2H), 5.15 (s, 2H), 5.98 (s, 2H), 6.09 (dd, 1H), 6.38 (d, 1H), 6.86 (s, 1H), 6.91 (s, 1H), 7.37 (d, 1H)

EXAMPLE 201 hexanoic acid 1-(6-chloro-benzo[1,3]dioxol-5-ylmethyl)-2-oxo-1,2-dihydro-pyridin-4-yl ester $^1$H NMR (CDCl$_3$, 300 MHz) δ 0.93 (t, 3H), 1.34-1.38 (m, 4H), 1.70-1.76 (m, 2H), 2.54 (t, 2H), 5.16 (s, 2H), 5.98 (s, 2H), 6.10 (dd, 1H), 6.40 (d, 1H), 6.87 (s, 1H), 6.91 (s, 1H), 7.37 (d, 1H)

EXAMPLE 202

1-(2-chloro-3-trifluoromethyl-benzyl)-4-pentyloxy-1H-pyridin-2-one $^1$H NMR (CDCl$_3$, 300 MHz) δ 0.95 (t, 3H), 1.37-1.45 (m, 4H), 1.78-1.81 (m, 2H), 3.94 (t, 2H), 5.25 (s, 2H), 5.95-5.98 (m, 2H), 7.19-7.38 (m, 3H), 7.65 (d, 1H)

EXAMPLE 203 thiophene-2-carboxyl acid 1-(6-chloro-benzo[1,3]dioxol-5-ylmethyl)-2-oxo-1,2-dihydro-pyridin-4-yl ester $^1$H NMR (CDCl$_3$, 300 MHz) δ 5.19 (s, 2H), 6.00 (s, 2H), 6.24 (dd, 1H), 6.53 (d, 1H), 6.88 (s, 1H), 6.94 (s, 1H), 7.21 (t, 1H), 7.42 (d, 1H), 7.72 (d, 1H), 7.98 (d, 1H)

EXAMPLE 204 toluene-4-sulfonic acid 1-(6-chloro-benzo[1,3]dioxol-5-ylmethyl)-2-oxo-1,2-dihydro-pyridin-4-yl ester $^1$H NMR (CDCl$_3$, 300 MHz) δ 2.48 (s, 3H) 5.10 (s, 2H), 6.00 (s, 2H), 6.14-6.15 (m, 2H), 6.84 (s, 1H), 6.87 (s, 1H), 7.34-7.35 (m, 1H), 7.38 (d, 2H), 7.81 (d, 2H)

EXAMPLE 205

1-(6-chloro-benzo[1,3]dioxol-5-ylmethyl)-4-(4,4,5,5,5-pentafluoro-pentyloxy)-1H-pyridin-2-one $^1$H NMR (CDCl$_3$, 300 MHz) δ 2.08-2.28 (m, 4H), 4.01 (t, 2H), 5.12 (s, 2H), 5.91-5.93 (m, 2H), 5.98 (s, 2H), 6.84 (s, 1H), 6.87 (s, 1H), 7.22-7.24 (m, 1H)

EXAMPLE 206

1-(6-chloro-benzo[1,3]dioxol-5-ylmethyl)-4-(2-dimethylamino-ethoxy)-1H-pyridin-2-one $^1$H NMR (CDCl$_3$, 300 MHz) δ 2.33 (s, 6H), 2.73 (t, 2H), 4.03 (t, 2H), 5.11 (s, 2H), 5.94-5.97 (m, 4H), 6.83 (s, 1H), 6.86 (s, 1H), 7.19 (d, 1H)

EXAMPLE 207

4-chloro-2-(2,4-dichloro-benzyloxy)-pyridine $^1$H NMR (CDCl$_3$, 300 MHz) δ 5.17 (s, 2H), 6.83 (dd, 1H), 6.93 (d, 1H), 7.28-7.47 (m, 3H), 8.23 (d, 1H)

EXAMPLE 208

4-chloro-1-(2,4-dichloro-benzyl)-1H-pyridin-2-one $^1$H NMR (CDCl$_3$, 300 MHz) δ 5.17 (s, 2H), 6.21 (dd, 1H), 6.65 (s, 1H), 7.22-7.42 (m, 3H), 7.43 (s, 1H)

EXAMPLE 209

1-(2,4-dichloro-benzyl)-4-(5-fluoro-pentyloxy)-1H-pyridin-2-one $^1$H NMR (CDCl$_3$, 300 MHz) δ 1.58-1.61 (m, 2H), 1.74-1.88 (m, 4H), 3.96 (t, 2H), 4.44 (t, 1H), 4.54 (t, 1H), 5.16 (s, 2H), 5.93-5.94 (m, 2H), 7.18-7.22 (m, 3H), 7.42 (s, 1H)

EXAMPLE 210

3-[1-(2,4-dichloro-benzyl)-2-oxo-1,2-dihydro-pyridin-4-yloxymethyl]-indole-1-carboxyl acid tetrabutyl ester $^1$H NMR (CDCl$_3$, 300 MHz) δ 1.61 (s, 9H), 5.18 (s, 2H), 5.40 (s, 2H), 5.95 (dd, 1H), 6.15 (d, 1H), 7.21-7.60 (m, 7H), 8.23 (d, 1H)

EXAMPLE 211

1-(2,4-dichloro-benzyl)-4-(2-thiophen-2-yl-ethoxy)-1H-pyridin-2-one $^1$H NMR (CDCl$_3$, 300 MHz) δ 3.30 (t, 2H), 4.15 (t, 2H) 5.13 (s, 2H), 5.90-5.97 (m, 2H), 6.87-6.98 (m, 2H), 7.15-7.22 (m, 4H), 7.41 (s, 1H)

EXAMPLE 212

1-(2,4-dichloro-benzyl)-4-(2-thiophen-3-yl-ethoxy)-1H-pyridin-2-one $^1$H NMR (CDCl$_3$, 300 MHz) 63.12 (t, 2H), 4.15 (t, 2H) 5.12 (s, 2H), 5.88-5.97 (m, 2H), 6.95-7.41 (m, 7H)

EXAMPLE 213

1-(2,4-dichloro-benzyl)-4-(2-pyrrol-1-yl-ethoxy)-1H-pyridin-2-one $^1$H NMR (CDCl$_3$, 300 MHz) δ 4.18 (t, 2H), 4.28 (t, 2H), 5.14 (s, 2H), 5.82-5.97 (m, 2H), 6.70-6.80 (m, 2H), 7.10-7.25 (m, 3H), 7.40 (s, 1H)

EXAMPLE 214

1-(2,4-dichloro-benzyl)-4-(3-pyrrol-1-yl-propoxy)-1H-pyridin-2-one $^1$H NMR (CDCl$_3$, 300 MHz) δ 2.20 (m, 2H), 3.82 (t, 2H), 4.03 (t, 2H), 5.14 (s, 2H), 5.86 (d, 1H), 5.94 (dd, 1H), 6.12-6.18 (m, 2H), 6.60-6.66 (m, 2H), 7.18-7.24 (m, 3H), 7.40 (s, 1H)

EXAMPLE 215

1-(3-amino-2-methyl-benzyl)-4-(2-thiophen-2-yl-ethoxy)-1H-pyridin-2-one $^1$H NMR (CDCl$_3$, 300 MHz) δ 2.01 (s, 3H), 3.28 (t, 2H), 3.65 (br s, 2H), 4.14 (t, 2H), 5.04 (s, 2H), 5.84 (dd, 1H), 5.95 (d, 1H), 6.57 (d, 1H), 6.70 (d, 1H), 6.88-7.02 (m, 4H), 7.16 (dd, 1H)

EXAMPLE 216

1-(3-amino-2-methyl-benzyl)-4-(2-pyrrol-1-yl-ethoxy)-1H-pyridin-2-one $^1$H NMR (CDCl$_3$, 300 MHz) δ 2.01 (s, 3H), 4.16 (t, 2H), 4.25 (t, 2H), 5.04 (s, 2H), 5.83 (dd, 1H), 5.90 (d, 1H), 6.16 (t, 2H), 6.57 (d, 1H), 6.71-6.75 (m, 3H), 6.91 (d, 1H), 7.02 (t, 1H)

EXAMPLE 217

1-(3-amino-2-methyl-benzyl)-4-[2-(4-methyl-thiazol-5-yl)-ethoxy]-1H-pyridin-2-one $^1$H NMR (CDCl$_3$, 300 MHz) δ 1.98 (s, 3H), 2.40 (s, 3H), 3.20 (t, 2H), 3.46 (br s, 2H), 4.06 (t, 2H), 5.02 (s, 2H), 5.81 (dd, 1H), 5.92 (d, 1H), 6.53 (d, 1H), 6.68 (d, 1H), 6.91 (d, 1H), 6.99 (t, 1H), 8.56 (s, 1H)

EXAMPLE 218

1-(3-Amino-2-methyl-benzyl)-4-(2-(5-bromothiophen-2-yl)-ethoxy)-1H-pyridin-2-one $^1$H NMR (CDCl$_3$, 300 MHz) δ 1.95 (s, 3H), 3.14 (t, 2H), 3.49 (br s, 2H), 4.05 (t, 2H), 4.99 (s, 2H), 5.81 (dd, 1H), 5.88 (m, 1H), 6.49 (d, 1H), 6.60 (m, 1H), 6.64 (d, 1H), 6.83 (m, 1H), 6.89 (dd, 1H), 6.96 (t, 1H)

EXAMPLE 219

1-(3-Amino-2-methyl-benzyl)-4-(2-(5-fluorothiophen-2-yl)-ethoxy)-1H-pyridin-2-one $^1$H NMR (CDCl$_3$, 300 MHz) δ 2.02 (s, 3H), 3.12 (dt, 2H), 4.09 (t, 2H), 5.05 (s, 2H), 5.85 (dd, 1H), 5.93 (d, 1H), 6.28 (dd, 1H), 6.46 (d, 1H), 6.58 (d, 1H), 6.72 (d, 1H), 6.92 (d, 1H), 7.03 (t, 1H)

EXAMPLE 220

1-[3-(2-Hydroxy-ethylamino)-2-methyl-benzyl]-4-(2-thiophen-2-yl-ethoxy)-1H-pyridin-2-one $^1$H NMR (CDCl$_3$, 300 MHz) δ 1.96 (s, 3H), 3.29 (m, 4H), 3.88 (t, 2H), 4.12 (t, 2H), 5.02 (s, 2H), 5.84 (dd, 1H), 5.93 (d, 1H), 6.53 (d, 1H), 6.66 (d, 1H), 6.92 (m, 3H), 7.10 (t, 1H), 7.16 (dd, 1H)

EXAMPLE 221

2-{2-Methyl-3-[2-oxo-4-(2-thiophene-2-yl-ethoxy)-2H-pyridin-1-ylmethyl]-phenylamino}-acetamide $^1$H NMR (CDCl$_3$, 300 MHz) δ 2.01 (s, 3H), 3.22 (t, 2H), 3.60 (d, 2H), 4.17 (t, 2H), 4.97 (s, 2H), 5.86 (m, 1H), 5.94 (dd, 1H), 6.20 (d, 1H), 6.29 (d, 1H), 6.95 (m, 3H), 7.33 (m, 2H)

EXAMPLE 222

1-[3-(Cyclopropylmethyl-amino)-2-methyl-benzyl]-4-(2-thiophen-2-yl-ethoxy)-1H-pyridin-2-one $^1$H NMR (CDCl$_3$, 300 MHz) δ 0.25 (dt, 2H), 0.57 (dt, 2H), 1.06-1.19 (m, 1H), 2.01 (s, 3H), 2.98 (d, 2H), 3.27 (t, 2H), 3.73 (br s, 1H), 4.14 (t, 2H), 5.05 (s, 2H), 5.82 (dd, 1H), 5.94 (d, 1H), 6.87-6.95 (m, 3H), 7.10 (t, 1H)

EXAMPLE 223

N-{2-Methyl-3-[2-oxo-4-(2-thiophen-2-yl-ethoxy)-2H-pyridin-1-ylmethyl]-phenylamino}-acetonitrile $^1$H NMR (CDCl$_3$, 300 MHz) δ 2.00 (s, 3H), 3.28 (t, 2H), 4.14 (m, 4H), 5.07 (s, 2H), 5.87 (dd, 1H), 5.93 (d, 1H), 6.66 (d, 1H), 6.71 (d, 1H), 6.93-6.96 (m, 3H), 7.15-7.19 (m, 2H)

EXAMPLE 224

N-(2-{2-Methyl-3-[2-oxo-4-(2-thiophen-2-yl-ethoxy)-2H-pyridin-1-ylmethyl]-phenylamino}-ethyl)-acetamide $^1$H NMR (CDCl$_3$, 300 MHz) δ 1.99 (m, 6H), 3.26-3.32 (m, 4H), 3.53-3.59 (m, 2H), 4.14 (t, 2H), 5.05 (s, 2H), 5.82 (dd, 1H), 5.94 (d, 1H), 6.52 (d, 1H), 6.61(d, 1H), 6.89-6.69 (m, 3H), 7.10 (t, 1H), 7.15 (d, 1H)

EXAMPLE 225

1-[2-Methyl-3-(2-pyrrol-1-yl-ethylamino)-benzyl]-4-(2-thiophen-2-yl-ethoxy)-1H-pyridin-2-one ¹H NMR (CDCl₃, 300 MHz) δ 1.85 (s, 3H), 3.28 (t, 2H), 3.51 (t, 3H), 4.14 (t, 4H), 5.05 (s, 2H), 5.84 (dd, 1H), 5.93 (d, 1H), 6.17 (m, 2H), 6.56 (d, 1H), 6.65 (m, 3H), 6.90 (m, 3H), 7.10-7.17 (m, 2H)

EXAMPLE 226

Synthesis of 1-[2-Methyl-3-(2-oxo-2-pyrrolidin-1-yl-ethylamino)-benzyl]-4-(2-thiophen-2-yl-ethoxy)-1H-pyridin-2-one A mixture of {2-Methyl-3-[2-oxo-4-(2-thiophen-2-yl-ethoxy)-2H-pyridin-1-ylmethyl]-phenylamino}-acetic acid (50 mg, 0.13 mmol), TBTU (60 mg, 0.19 mmol), pyrrolidine (0.02 ml, 0.25 mmol) and triethylamine (0.09 ml, 0.63 mmol) was dissolved in N,N-dimethylformamide (0.5 ml) and stirred at room temperature. After 1 hour, the resulting solution was evaporated, extracted with dichloromethane (20 ml) and subjected to silica gel column chromatography (ethyl acetate/MeOH, 20:1) to obtain the titled compound (41 mg, 71%).
¹H NMR (CDCl₃, 300 MHz) δ 1.88-1.95 (m, 2H), 1.99-2.09 (m, 5H), 3.27 (t, 2H), 3.44 (t, 2H), 3.55 (t, 2H), 3.81 (s, 2H), 4.14 (t, 2H), 5.06 (s, 2H), 5.83 (dd, 1H), 5.95 (d, 1H), 6.51 (d, 1H), 6.54 (d, 1H), 6.87-6.94 (m, 3H), 7.10 (t, 1H) 7.16 (dd, 1H)

EXAMPLES 227 TO 230

The procedure of Example 226 was repeated except the starting material to obtain the titled compound.

EXAMPLE 227

1-[2-Methyl-3-(2-oxo-2-piperidin-1-yl-ethylamino)-benzyl]-4-(2-thiophen-2-yl-ethoxy)-1H-pyridin-2-one ¹H NMR (CDCl₃, 300 MHz) δ 1.53-1.74 (m, 6H), 2.07 (s, 3H), 3.27 (t, 2H), 3.39 (t, 2H), 3.62 (t, 2H), 3.88 (s, 2H), 4.14 (t, 2H), 5.06 (s, 2H), 5.83 (dd, 1H), 5.95 (d, 1H), 6.52 (d, 1H), 6.84-6.96 (m, 3H), 7.10 (t, 1H) 7.16 (dd, 1H)

EXAMPLE 228

N,N-Dimethyl-2-{2-methyl-3-[2-oxo-4-(2-thiophen-2-yl-ethoxy)-2H-pyridin-1-ylmethyl]-phenylamino}-acetamide ¹H NMR (CDCl₃, 300 MHz) δ 2.08 (s, 3H), 3.05 (s, 6H), 3.28 (t, 2H), 3.88 (s, 2H), 4.15 (t, 2H), 5.07 (s, 2H), 5.83 (dd, 1H), 5.94 (d, 1H), 6.50-6.55 (m, 2H), 6.89-6.96 (m, 3H), 7.08-7.17 (m, 2H)

EXAMPLE 229

1-{2-Methyl-3-[2-(4-methyl-piperazin-1-yl)-2-oxo-ethylamino]-benzyl}-4-(2-thiophen-2-yl-ethoxy)-1H-pyridin-2-one ¹H NMR (CDCl₃, 300 MHz) δ 2.07 (s, 3H), 2.33 (s, 3H), 2.45 (d, 4H), 3.28 (t, 2H), 3.48 (d, 2H), 3.70 (d, 2H), 3.89 (s, 2H), 4.14 (t, 2H), 5.06 (s, 2H), 5.83 (dd, 1H), 5.94 (d, 1H), 6.52 (dd, 2H), 6.88-6.97 (m, 3H), 7.08-7.17 (m, 2H)

EXAMPLE 230

1-[2-Methyl-3-(2-morpholin-4-yl-2-oxo-ethylamino)-benzyl]-4-(2-thiophen-2-yl-ethoxy)-1H-pyridin-2-one ¹H NMR (CDCl₃, 300 MHz) δ 2.08 (s, 3H), 2.28 (t, 2H), 3.48 (t, 2H), 3.62-3.79 (m, 6H), 3.90 (s, 2H), 4.15 (t, 2H), 5.07 (s, 2H), 5.83 (dd, 1H), 5.94 (d, 1H), 6.48 (d, 1H), 6.54 (d, 1H), 6.88-6.96 (m, 3H), 7.08-7.18 (m, 2H)

EXAMPLES 231 TO 266

The procedure of Example 1 was repeated except the starting material to obtain the titled compound.

EXAMPLE 231

1-(3-Amino-2-methyl-benzyl)-4-(2-furan-2-yl-ethoxy)-1H-pyridin-2-one

¹H NMR (CDCl₃, 300 MHz) δ 2.01 (s, 3H), 3.10 (t, 2H), 4.17 (t, 2H), 5.05 (s, 2H), 5.81 (dd, 1H), 5.95 (d, 1H), 6.10 (d, 1H), 6.30 (d, 1H), 6.57 (d, 1H), 6.69 (d, 1H), 6.90 (d, 1H), 7.02(t, 1H), 7.29 (d, 1H)

EXAMPLE 232

1-(3-Amino-2-methyl-benzyl)-4-[2-(5-methyl-thiophen-2-yl)-ethoxy]-1H-pyridin-2-one ¹H NMR (CD₃OD, 300 MHz) δ 2.02(s, 3H), 2.40 (s, 3H), 3.19 (t, 2H), 4.16 (t, 2H), 5.07(s, 2H), 5.96 (d, 1H), 6.06 (dd, 1H), 6.40 (d, 1H), 6.57 (dd, 1H), 6.67 (d, 1H), 6.73 (d, 1H), 6.95 (t, 1H), 7.21 (d, 1H)

EXAMPLE 233

1-(3-Amino-2-methyl-benzyl)-4-[2-(5-chloro-thiophen-2-yl)-ethoxy]-1H-pyridin-2-one ¹H NMR (CDCl₃, 300 MHz) δ 2.01(s, 3H), 3.18 (t, 2H), 3.70 (br s, 2H), 4.10 (t, 2H), 5.05 (s, 2H), 5.84 (dd, 1H), 2.92 (d, 1H), 6.57 (d, 1H), 6.65 (d, 1H), 6.69 (d, 1H), 6.74 (d, 1H), 6.92 (d, 1H), 7.02 (t, 1H)

EXAMPLE 234

1-(2,4-dichloro-benzyl)-4-[2-(3-methyl-thiophen-2-yl)-ethoxy]-1H-pyridin-2-one

¹H NMR (CDCl₃, 300 MHz) δ 2.20(s, 3H), 3.20 (t, 2H), 4.10 (t, 2H), 5.14 (s, 2H), 5.93-5.97 (m, 2H), 6.80 (d, 1H), 7.07 (d, 1H), 7.17-7.20 (m, 3H), 7.40 (s, 1H)

EXAMPLE 235

1-(3-Amino-2-methyl-benzyl)-4-(2-benzo[b]thiophen-3-yl-ethoxy)-1H-pyridin-2-one

¹H NMR (CD₃OD, 300 MHz) δ 2.00 (s, 3H), 3.31 (t, 2H), 4.31 (t, 2H), 5.04 (s, 2H), 5.96-6.01 (m, 2H), 6.37 (d, 1H), 6.72 (d, 1H), 6.93 (t, 1H), 7.14-7.42 (m, 5H), 7.84 (t, 1H)

EXAMPLE 236

1-(3-Amino-2-methyl-benzyl)-4-[2-(5-chloro-3-methyl-benzo[b]thiophen-2-yl)-ethoxy]-1H-pyridin-2-one $^1$H NMR (CD$_3$OD+a few drop of CDCl$_3$, 300 MHz) δ 1.97 (s, 3H), 2.32 (s, 3H), 3.32 (t, 2H), 4.20 (t, 2H), 5.01 (s, 2H), 5.92-5.97 (m, 2H), 6.45 (d, 1H), 6.71 (d, 1H), 6.96 (t, 1H), 7.02 (d, 1H), 7.21 (dd, 1H), 7.55 (d, 1H), 7.65 (d, 1H)

EXAMPLE 237

1-(3-amino-2-methyl-benzyl)-4-[2-(3-methyl-benzo[b]thiophen-2-yl)-ethoxy]-1H-pyridin-2-one $^1$H NMR (CDCl$_3$, 300 MHz) δ 2.00(s, 3H), 2.36 (s, 3H), 3.33 (t, 2H), 3.73 (br s, 2H), 4.18 (t, 2H), 5.05 (s, 2H), 5.82 (dd, 1H), 5.95 (d, 1H), 6.56 (d, 1H), 6.69 (d, 1H), 6.91 (d, 1H), 7.02 (t, 1H), 7.27-7.39 (m, 2H), 7.63 (d, 1H), 7.77 (d, 1H)

EXAMPLE 238

1-(3-Amino-2-methyl-benzyl)-4-[2-(5-methyl-furan-2-yl)-ethoxy]-1H-pyridin-2-one $^1$H NMR (CDCl$_3$, 300 MHz) δ 2.00 (s, 3H), 2.24 (s, 3H), 3.03 (t, 2H), 4.13 (t, 2H), 5.03 (s, 2H), 5.80-5.86 (m, 2H), 5.94-5.96 (m, 2H), 6.53 (d, 1H), 6.66 (d, 1H), 6.89 (d, 1H), 7.00(t, 1H)

EXAMPLE 239

1-(3-Amino-2-methyl-benzyl)-4-[2-(5-ethyl-furan-2-yl)-ethoxy]-1H-pyridin-2-one $^1$H NMR (CDCl$_3$, 300 MHz) δ 1.20 (t, 3H), 1.99 (s, 3H), 2.59 (q, 2H), 3.04 (t, 2H), 3.68 (br s, 2H), 4.14 (t, 2H), 5.04 (s, 2H), 5.80 (dd, 1H), 5.86 (d, 1H), 5.94 (d, 1H), 5.97 (d, 1H), 6.55 (d, 1H), 6.67 (d, 1H), 6.89 (d, 1H), 7.00 (t, 1H)

EXAMPLE 240

5-[1-(3-amino-2-methyl-benzyl)-2-oxo-1,2-dihydro-pyridin-4-yloxymethyl]-furan-2-carboxylic acid ethyl ester $^1$H NMR (CDCl$_3$, 300 MHz) δ 1.37 (t, 3H), 2.00 (s, 3H), 4.36 (q, 2H), 4.97 (s, 2H), 5.05 (s, 2H), 5.84 (dd, 1H), 6.01 (d, 1H), 6.55-6.58 (m, 2H), 6.69 (d, 1H), 6.93 (d, 1H), 7.02 (t, 1H), 7.14 (d, 1H)

EXAMPLE 241

1-[3-(2-dimethylamino-ethylamino)-2-methyl-benzyl]-4-(2-thiophen-2-yl-ethoxy)-1H-pyridin-2-one $^1$H NMR (CDCl$_3$, 300 MHz) δ 1.99 (s, 3H), 2.30 (s, 6H), 2.60 (t, 2H), 3.17 (t, 2H), 3.28 (t, 2H), 4.14 (t, 2H), 5.06 (s, 2H), 5.83 (dd, 1H), 5.94 (d, 1H), 6.88-6.96 (m, 3H), 7.09-7.18 (m, 2H)

EXAMPLE 242

1-(3-amino-2-methyl-benzyl)-4-[2-(5-methylsulfanyl-thiophen-2-yl)-ethoxy]-1H-pyridin-2-one $^1$H NMR (CDCl$_3$, 300 MHz) δ 2.01 (s, 3H), 2.45 (s, 3H), 3.21 (t, 2H), 3.70 (br s, 2H), 4.12 (t, 2H), 5.05 (s, 2H), 5.84 (dd, 1H), 5.93 (d, 1H), 6.57 (d, 1H), 6.69-6.73 (m, 2H), 6.91-6.93 (m, 2H), 7.02 (t, 1H)

EXAMPLE 243

1-(3-amino-2-methyl-benzyl)-4-(2-benzofuran-2-yl-ethoxy)-1H-pyridin-2-one $^1$H NMR (CDCl$_3$, 300 MHz) δ 2.05 (s, 3H), 3.25 (t, 2H), 4.29 (t, 2H), 5.05 (s, 2H), 5.82 (d, 1H), 6.00 (s, 1H), 6.51-6.71 (m, 3H), 6.91 (d, 1H), 7.04 (t, 1H), 7.17-7.28 (m, 2H), 7.42 (d, 1H), 7.50 (d, 1H)

EXAMPLE 244

1-(3-amino-2-methyl-benzyl)-4-[2-(3-methyl-isoxazol-5-yl)-ethoxy]-1H-pyridin-2-one $^1$H NMR (CDCl$_3$+a few drop of CD$_3$OD, 300 MHz) δ 1.86 (s, 3H), 1.93 (s, 3H), 2.63 (t, 2H), 4.14 (t, 2H), 4.96 (s, 2H), 5.82 (dd, 1H), 5.90 (d, 1H), 6.46 (d, 1H), 6.64 (d, 1H), 6.86 (d, 1H), 6.94 (t, 1H), 7.26 (s, 1H)

EXAMPLE 245

1-(3-amino-2-methyl-benzyl)-4-[2-(4,5-dimethyl-thiophen-2-yl)-ethoxy]-1H-pyridin-2-one $^1$H NMR (CDCl$_3$, 300 MHz) δ 2.00 (s, 3H), 2.07 (s, 3H), 2.78 (s, 3H), 3.14 (t, 2H), 4.09 (t, 2H), 5.05 (s, 2H), 5.85 (dd, 1H), 5.95 (d, 1H), 6.55 (s, 1H), 6.56 (d, 1H), 6.69 (d, 1H), 6.91 (d, 1H), 7.01 (t, 1H)

EXAMPLE 246

1-(3-amino-2-methyl-benzyl)-4-[2-(5-ethyl-thiophen-2-yl)-ethoxy]-1H-pyridin-2-one $^1$H NMR (CDCl$_3$, 300 MHz) δ 1.28 (t, 3H), 2.00 (s, 3H), 2.78 (q, 2H), 3.20 (t, 2H), 3.69 (br s, 2H), 4.11 (t, 2H), 5.04 (s, 2H), 5.84 (dd, 1H), 5.94 (d, 1H), 6.55-6.70 (m, 4H), 6.91 (d, 1H), 7.01 (t, 1H)

EXAMPLE 247

1-(3-amino-2,6-dichloro-benzyl)-4-(2-thiophen-2-yl-ethoxy)-1H-pyridin-2-one $^1$H NMR (CDCl$_3$, 300 MHz) δ 3.25 (t, 2H), 4.12 (t, 2H), 4.30 (br s, 2H), 5.30 (s, 2H), 5.81 (dd, 1H), 5.92 (d, 1H), 6.70-6.93 (m, 4H), 7.13-7.16 (m, 2H)

EXAMPLE 248

N-{2-methyl-3-[2-oxo-4-(2-thiophen-2-yl-ethoxy)-2H-pyridin-1-ylmethyl]-phenyl}-acetamide $^1$H NMR (DMSO-d$_6$, 300 MHz) δ 2.02 (s, 3H), 2.08 (s, 3H), 3.22 (t, 2H), 4.17 (t, 2H), 5.00 (s, 2H), 5.87 (d, 1H), 5.99 (dd, 1H), 6.57 (d, 1H), 6.94-6.96 (m, 2H), 7.07 (t, 1H), 7.19 (d, 1H), 7.32-7.34 (m, 1H), 7.43 (d, 1H)

EXAMPLE 249

1-[2-methyl-3-(2-piperidin-1-yl-ethylamino)-benzyl]-4-(2-thiophen-2-yl-ethoxy)-1H-pyridin-2-one $^1$H NMR (CDCl$_3$, 300 MHz) δ 1.59 (br s, 2H), 1.83-1.87 (m, 4H), 2.07 (s, 3H), 2.90-2.94 (m, 4H), 3.06 (t, 2H), 3.28 (t, 2H), 3.52 (t, 2H), 4.13 (t, 2H), 4.60 (br s, 1H), 5.03 (s, 2H), 5.86 (dd, 1H), 5.92 (d, 1H), 6.46 (d, 1H), 6.59 (d, 1H), 6.88-6.96 (m, 3H), 7.07 (t, 1H), 7.16 (dd, 1H)

EXAMPLE 250

1-[2-methyl-3-(2-morpholin-4-yl-ethylamino)-benzyl]-4-(2-thiophen-2-yl-ethoxy)-1H-pyridin-2-one $^1$H NMR (CDCl$_3$, 300 MHz) δ 2.00 (s, 3H), 2.47 (t, 4H), 2.69 (t, 2H), 3.18 (t, 2H), 3.28 (t, 2H), 3.70 (t, 4H), 4.14 (t, 2H), 5.06 (s, 2H), 5.83 (dd, 1H), 5.94 (d, 1H), 6.53 (d, 1H), 6.61 (d, 1H), 6.88-6.95 (m, 3H), 7.10 (d, 1H), 7.15 (t, 1H)

EXAMPLE 251

N-{2-methyl-3-[2-oxo-4-(2-thiophen-2-yl-ethoxy)-2H-pyridin-1-ylmethyl]-phenyl}-methanesulfonamide $^1$H NMR (CDCl$_3$, 300 MHz) δ 2.15 (s, 3H), 2.95 (s, 3H), 3.30 (t, 2H), 4.17 (t, 2H), 5.01 (s, 2H), 5.97 (dd, 2H), 6.03 (d, 1H), 6.74 (d, 1H), 6.89-6.96 (m, 2H), 7.01 (d, 1H), 7.09 (t, 1H), 7.16 (dd, 1H), 7.28 (t, 1H), 7.60 (br s, 1H)

EXAMPLE 252

1-(3-amino-2-methyl-benzyl)-4-[2-(4-bromothiophen-2-yl)-ethoxy]-1H-pyridin-2-one $^1$H NMR (CDCl$_3$, 300 MHz) δ 1.99 (s, 3H), 3.22 (t, 2H), 3.69 (br s, 2H), 4.10 (t, 2H), 5.04 (s, 2H), 5.83 (dd, 1H), 5.92 (d, 1H), 6.55 (d, 1H), 6.68 (d, 1H), 6.80 (s, 1H), 6.91 (d, 1H), 6.98-7.06 (m, 2H)

EXAMPLE 253

1-(6-chloro-benzo[1,3]dioxol-5-ylmethyl)-4-(2-pyrrol-1-yl-ethoxy)-1H-pyridin-2-one $^1$H NMR (CDCl$_3$, 300 MHz) δ 4.15 (t, 2H), 4.25 (t, 2H), 5.07 (s, 2H), 5.85-5.90 (m, 2H), 5.94 (s, 2H), 6.15-6.16 (m, 2H), 6.60-6.72 (m, 2H), 6.79 (s, 1H), 6.83 (s, 1H), 7.18 (d, 1H)

EXAMPLE 254

1-(6-chloro-benzo[1,3]dioxol-5-ylmethyl)-4-(2-thiophen-2-yl-ethoxy)-1H-pyridin-2-one $^1$H NMR (CDCl$_3$, 300 MHz) δ 3.26 (t, 2H), 4.12 (t, 2H), 5.06 (s, 2H), 5.89-5.92 (m, 4H), 6.78-6.94 (m, 4H), 7.14-7.18 (m, 2H)

EXAMPLE 255

1-[2-methyl-3-(2-pyrrolidin-1-yl-ethylamino)-benzyl]-4-(2-thiophen-2-yl-ethoxy)-1H-pyridin-2-one $^1$H NMR (CDCl$_3$, 300 MHz) δ 1.78 (br s, 4H), 1.98 (s, 3H), 2.55 (br s, 4H), 2.79 (t, 2H), 3.23 (t, 2H), 3.28 (t, 2H), 4.14 (t, 2H), 4.33 (br s, 1H), 5.05 (s, 2H), 5.81-5.85 (m, 1H), 5.94 (d, 1H), 6.53 (d, 1H), 6.63 (d, 1H), 6.88-6.96 (m, 3H), 7.09-7.18 (m, 2H)

EXAMPLE 256

N-(2-{2-methyl-3-[2-oxo-4-(2-thiophen-2-yl-ethoxy)-2H-pyridin-1-ylmethyl]-phenylamino}-ethyl)-acetamide $^1$H NMR (CDCl$_3$, 300 MHz) δ 1.94 (s, 6H), 3.25 (t, 4H), 3.49 (q, 2H), 4.10 (t, 2H), 5.00 (s, 2H), 5.83-5.89 (m, 2H), 6.44 (d, 1H), 6.58 (d, 1H), 6.73 (t, 1H), 6.87-6.94 (m, 3H), 7.06 (t, 1H), 7.14 (d, 1H)

EXAMPLE 257

1-{2-methyl-3-[(pyridin-3-ylmethyl)-amino]-benzyl}-4-(2-thiophen-2-yl-ethoxy)-1H-pyridin-2-one $^1$H NMR (CDCl$_3$, 300 MHz) δ 2.03 (s, 3H), 3.28 (t, 2H), 4.14 (t, 2H), 4.42 (s, 2H), 5.07 (s, 2H), 5.86 (dd, 1H), 5.93 (d, 1H), 6.56 (d, 2H), 6.88-6.96 (m, 3H), 7.07 (t, 1H), 7.16 (dd, 1H), 7.30-7.34 (m, 1H), 7.73 (d, 1H), 8.54 (s, 1H), 8.64 (s, 1H)

EXAMPLE 258

2-methyl-3-[2-oxo-4-(2-thiophen-2-yl-ethoxy)-2H-pyridin-1-ylmethyl]-phenyl ester $^1$H NMR (CDCl$_3$, 300 MHz) δ 2.26 (s, 3H), 3.16 (s, 3H), 3.27 (t, 2H), 4.14 (t, 2H), 5.06 (s, 2H), 5.93-5.95 (m, 2H), 6.88-7.00 (m, 4H), 7.14-7.26 (m, 3H)

EXAMPLE 259

1-{2-methyl-3-[(pyridin-4-ylmethyl)-amino]-benzyl}-4-(2-thiophen-2-yl-ethoxy)-1H-pyridin-2-one $^1$H NMR (CDCl$_3$, 300 MHz) δ 2.07 (s, 3H), 3.28 (t, 2H), 4.14 (t, 2H), 4.44 (s, 2H), 5.08 (s, 2H), 5.86 (dd, 1H), 5.94 (d, 1H), 6.42 (d, 1H), 6.54 (d, 1H), 6.88-7.11 (m, 4H), 7.16 (dd, 1H), 7.30 (d, 2H), 8.55 (d, 2H)

EXAMPLE 260

1-{2-methyl-3-[(thiazol-4-ylmethyl)-amino]-benzyl}-4-(2-thiophen-2-yl-ethoxy)-1H-pyridin-2-one $^1$H NMR (CDCl$_3$, 300 MHz) δ 2.04 (s, 3H), 3.28 (t, 2H), 4.14 (t, 2H), 4.56 (s, 2H), 5.06 (s, 2H), 5.84 (dd, 1H), 5.94 (d, 1H), 6.55 (d, 1H), 6.65 (d, 1H), 6.88-7.20 (m, 6H), 8.85 (s, 1H)

EXAMPLE 261

1-[3-(4-methoxy-benzyloxy)-2-methyl-benzyl]-4-(2-thiophen-2-yl-ethoxy)-1H-pyridin-2-one $^1$H NMR (CDCl$_3$, 300 MHz) δ 2.15 (s, 3H), 3.29 (t, 2H), 3.81 (s, 3H), 4.16 (t, 2H), 4.99 (s, 2H), 5.08 (s, 2H), 5.88 (dd, 1H), 6.00 (d, 1H), 6.68 (d, 1H), 6.90-6.96 (m, 6H), 7.11-7.18 (m, 2H), 7.35 (d, 2H)

EXAMPLE 262

1-{3-[(3,5-dimethyl-isoxazol-4-ylmethyl)-amino]-2-methyl-benzyl}-4-(2-thiophen-2-yl-ethoxy)-1H-pyridin-2-one $^1$H NMR (CDCl$_3$, 300 MHz) δ 1.98 (s, 3H), 2.26 (s, 3H), 2.37 (s, 3H), 3.28 (t, 2H), 4.04 (s, 2H), 4.15 (t, 2H), 5.07 (s, 2H), 5.85-5.95 (m, 2H), 6.62 (d, 1H), 6.74 (d, 1H), 6.88-6.96 (m, 3H), 7.14-7.19 (m, 2H)

EXAMPLE 263

1-(3-hydroxy-2-methyl-benzyl)-4-(2-thiophen-2-yl-ethoxy)-1H-pyridin-2-one $^1$H NMR (CDCl$_3$+a few drop of CD$_3$OD, 300 MHz) δ 1.96 (s, 3H), 3.16 (t, 2H), 4.05 (t, 2H), 4.91 (s, 2H), 5.85-5.88 (m, 2H), 6.41 (d, 1H), 6.66 (d, 1H), 6.76-6.90 (m, 4H), 7.04 (d, 1H)

EXAMPLE 264

1-{2-methyl-3-[(1-methyl-pyrrolidin-2-ylmethyl)-amino]-benzyl}-4-(2-thiophen-2-yl-ethoxy)-1H-pyridin-2-one $^1$H NMR (CDCl$_3$+a few drop of CD$_3$OD, 300 MHz) δ 1.57-1.67 (m, 3H), 1.79-1.89 (m, 6H), 2.25 (s, 3H), 2.47-2.50 (m, 1H), 2.98-3.04 (m, 2H), 3.13 (t, 2H), 4.01 (t, 2H), 4.88 (s, 2H), 5.78-5.81 (m, 2H), 6.32 (d, 1H), 6.47 (d, 1H), 6.73-6.85 (m, 3H), 6.94 (t, 1H), 7.00 (d, 1H)

EXAMPLE 265

1-{2-methyl-3-[2-(1-methyl-pyrrolidin-2-yl)-ethylamino]-benzyl}-4-(2-thiophen-2-yl-ethoxy)-1H-pyridin-2-one $^1$H NMR (CDCl$_3$, 300 MHz) δ 1.67-1.79 (m, 3H), 1.90-1.98 (m, 6H), 2.24 (q, 2H), 2.40 (s, 3H), 3.10-3.30 (m, 5H), 4.14 (t, 2H), 4.88 (br s, 1H), 5.04 (s, 2H), 5.82 (dd, 1H), 5.93 (d, 1H), 6.52 (d, 1H), 6.60 (d, 1H), 6.88-6.96 (m, 3H), 7.08-7.17 (m, 2H)

EXAMPLE 266

(2-{2-methyl-3-[2-oxo-4-(2-thiophen-2-yl-ethoxy)-2H-pyridin-1-ylmethyl]-phenylamino}-ethyl)-phosphonic acid diethyl ester $^1$H NMR (CDCl$_3$, 300 MHz) δ 1.32 (t, 6H), 2.02 (s, 3H), 2.10-2.20 (m, 2H), 3.28 (t, 2H), 3.42-3.53 (m, 2H), 4.07-4.17 (m, 6H), 5.06 (s, 2H), 5.85 (dd, 1H), 5.96 (s, 1H), 6.57 (d, 1H), 6.68 (d, 1H), 6.88-6.96 (m, 3H), 7.10-7.17 (m, 2H)

Preparation of 4-(isobutylthio)pyridine 1-oxide: A solution of 5.80 g of isobutylthiol in 30 ml of DMF was stirred at room temperature and 2.55 g of NaOMe was added. After 30 mins 6.0 g of N-oxide was added and the reaction mixture was heated at reflux for 15 hours. The mixture was cooled, then solution was evaporated, extracted with dichloromethane and subjected to silica gel column chromatography (hexane/ethyl acetate) to obtain 5.8 g of 4-(isobutylthio)pyridine 1-oxide $^1$H NMR (CDCl$_3$, 300 MHz) δ 0.99(s, 3H), 1.01(s, 3H), 1.85-1.89(m, 1H), 2.78(d, J=6.9 Hz, 2H), 7.04(d, J=7.2 Hz, 2H), 8.01(d, J=7.5 Hz, 2H)

Preparation of 4-(isobutylthio)pyridine-2(1H)-one: A mixture of 500 mg of 4-(isobutylthio)pyridine-N-oxide, 5 ml of acetic anhydride was heated at reflux for 10 hours. The mixture was cooled, then added MeOH and 3N NaOH was added dropwise at pH 9~11 and stirred. After 1 hour solution was evaporated and 3N HCl was added dropwise at pH6.5~7.5, extracted with ethyl acetate and subjected to silica gel column chromatography (hexane/ethyl acetate) to obtain the compound (90 mg).

$^1$H NMR (CDCl$_3$, 300 MHz) δ 1.05(s, 3H), 1.07(s, 3H), 1.95-2.00(m, 1H), 2.79(d, J=6.9 Hz, 2H), 6.19(dd, 1H), 6.31 (s, 1H), 7.21(d, J=6.9 Hz, 1H)

EXAMPLE 267

4-(isobutylthio)-1-(2-methyl-3-nitrobenzyl)pyridin-2(1H)-one

Preparation of 4-(isobutylthio)-1-(2-methyl-3-nitrobenzyl)pyridine-2(1H)-one: A mixture of 100 mg of 4-(isobutylthio)pyridine-2(1H)-one, 2 ml of DMF, 65 mg of t-BuOK was stirred at room temperature and 105 mg of 2-methyl-3-nitrobenzyl chloride was added. After 3 hour, the resulting solution was evaporated, extracted with dichloromethane and subjected to silica gel column chromatography (hexane/ethyl acetate) to obtain the compound (90 mg).

$^1$H NMR (CDCl$_3$, 300 MHz) δ 1.06(s, 3H), 1.08(s, 3H), 1.94-2.03(m, 1H), 2.42(s, 3H), 2.80(, J=6.9 Hz, 2H), 5.15(s, 2H), 6.07(dd, 1H), 6.35(s, 1H), 6.93(, J=7.5 Hz, 1H), 7.19-7.33(m, 2H), 7.71(, J=8.1 Hz, 1H)

EXAMPLES 268 TO 280

The procedure of Example 267 was repeated except the starting material to obtain the titled compound.

EXAMPLE 268

1-(3-amino-2-methylbenzyl)-4-(isobutylthio)pyridin-2(1H)-one

A mixture of 400 mg of 1-(3-amino-2-methylbenzyl)-4-(isobuthylthio)pyridin-2(1H)-one, 5 ml of ethyl alcohol, 3 ml of Raney nickel in water was stirred at room temperature and 3.5 ml of NH$_2$NH$_2$H$_2$O was added dropwise. After 1 hour, the catalyst was removed by filtration through Celite, and resulting solution was evaporated, extracted with dichloromethane to obtain the title compound (200 mg).

$^1$H NMR (CDCl$_3$, 300 MHz) δ 1.01-1.07(m, 6H), 1.95-1.99(m, 1H), 2.13(s, 3H), 2.77(d, J=6.9 Hz, 2H), 5.07(s, 2H), 5.97(dd, 1H), 6.32(s, 1H), 6.70(d, J=7.8 Hz, 1H), 6.85-6.92 (m, 2H), 7.08(t, J=7.8 Hz, 1H)

EXAMPLE 269

1-(3-amino-2-methylbenzyl)-4-(furan-2-ylmethylthio)pyridine-2(1H)-one $^1$H NMR (CDCl$_3$, 300 MHz) δ 2.03(s,3H), 4.14(s,2H), 5.05(s,2H), 5.96(dd, 1H), 6.31(s, 2H), 6.45(d, J=7.8 Hz, 1H), 6.76(d, J=7.5 Hz, 1H), 6.88(d, J=6.9 Hz, 1H), 7.04(t, J=7.8 Hz, 1H), 7.36(s, 1H)

EXAMPLE 270

1-(3-amino-2-methylbenzyl)-4-(pentylthio)pyridine-2-(1H)-one $^1$H NMR (CDCl$_3$, 300 MHz) δ 0.89-0.93(m, 3H), 1.31-1.44(m, 4H), 1.66-1.73(m, 2H), 2.03(s, 3H), 2.85-2.90(m, 2H), 5.05(s, 2H), 5.92-5.95(m, 1H), 6.33(s, 1H), 6.60(d, J=7.2 Hz, 1H), 6.73(d, J=7.8 Hz, 1H), 6.85(q, 1H), 7.03(t, J=7.8 Hz, 1H)

EXAMPLE 271

1-(3-amino-2-methylbenzyl)-4-(phenethylthio)pyridine-2(1H)-one $^1$H NMR (CDCl$_3$, 300 MHz) δ 2.13(s, 3H), 3.00(t, J=7.5 Hz, 2H), 3.16(t, J=7.5 Hz, 2H), 5.06(s, 2H), 5.94-5.97(dd, 1H), 6.39(s, 1H), 6.66(bs, 1H), 6.88(d, J=7.5 Hz, 2H), 7.06-7.10(m, 1H), 7.19-7.35(m, 3H)

EXAMPLE 272

1-(3-amino-2-methylbenzyl)-4-(butylthio)pyridine-2(1H)-one $^1$H NMR (CDCl$_3$, 300 MHz) δ 0.95(t, J=7.2 Hz, 3H), 1.43-1.50(m,2H), 1.67-1.72(m,2H), 2.04(s, 3H), 2.89(t, J=7.3 Hz, 2H), 5.05(s, 2H), 5.94(dd, 1H), 6.33(s, 1H), 6.61(d, J=7.6 Hz, 1H), 6.75(d, J=8.1 Hz, 1H), 6.86(d, J=7.2 Hz, 1H), 7.04(t, J=7.6 Hz, 1H)

EXAMPLE 273

1-(3-amino-2-methylbenzyl)-4-(thiophen-2-ylmethylthio)pyridine-2(1H)-one $^1$H NMR (CDCl$_3$, 300 MHz) δ 2.03(s, 3H), 4.34(s,2H), 5.04(s, 2H), 5.95(dd, 1H), 6.41(bs, 1H), 6.60(d, J=7.5 Hz, 1H), 6.75(d, J=7.5 Hz, 1H), 6.87-6.95(m, 2H), 7.01-7.05(m, 2H), 7.21-7.26(m, 1H)

EXAMPLE 274

1-(3-amino-2-methylbenzyl)-4-(pentylthio)pyridine-2(1H)-one $^1$H NMR (CDCl$_3$, 300 MHz) δ 0.92(t, J=6.8 Hz, 3H), 1.32-1.46(m, 4H), 1.68-1.78(m, 2H), 2.43(s, 3H), 2.91(t, J=7.3 Hz, 2H), 5.15(s, 2H), 6.07(dd, 1H), 6.38-6.39(m, 1H), 6.94(d, J=7.2 Hz, 1H), 7.20-7.31(m, 2H), 7.72(d, J=8.1 Hz, 2H)

EXAMPLE 275

1-(3-amino-2-methylbenzyl)-4-(propylthio)pyridine-2(1H)-one $^1$H NMR (CDCl$_3$, 300 MHz) δ 1.05(t, J=7.5 Hz, 3H), 1.71-1.78(m, 2H), 2.02(s, 3H), 2.87(t, J=7.3 Hz, 2H), 5.06(s, 2H), 5.94(dd, 1H), 6.33(d, J=1.8 Hz, 1H), 6.59(d, J=7.8 Hz, 1H), 6.70(d, J=7.5 Hz, 1H), 6.86(d, J=7.2 Hz, 1H), 7.03(t, J=7.8 Hz, 1H)

EXAMPLE 276

1-(3-amino-2-methylbenzyl)-4-(1-methylbutylthio)pyridine-2(1H)-one $^1$H NMR (CDCl$_3$, 300 MHz) δ 0.93-1.02(m, 6H), 1.55-1.62(m, 2H), 1.68-1.75(m, 1H), 2.06(s, 3H), 2.89(t, J=7.5 Hz, 2H), 5.06(s, 2H), 5.94(dd, 1H), 6.33(s, 1H), 6.63(d, J=7.2 Hz, 1H), 6.78(d, J=8.1 Hz, 1H), 6.86(d, J=7.2 Hz, 1H), 7.04(t, J=7.6 Hz, 1H)

EXAMPLE 277

N,N-dimethyl-3-(2-methyl-3-((2-oxo-4-(2-(thiophen-2-yl)ethoxy)pyridin-1(2H)-yl)methyl)phenylamino)propane-1-sulfonamide $^1$H NMR (CDCl$_3$, 300 MHz) δ 2.06(s, 3H), 2.23(t, J=6.8 Hz, 2H), 2.87(s, 6H), 3.06(t, J=7.2 Hz, 2H), 3.29(t, J=6.5 Hz, 2H), 3.39(t, J=6.7 Hz, 2H), 3.62-3.68(m, 1H), 4.14-4.18(m, 2H), 5.06(s, 2H), 5.87(dd, 1H), 5.97(d, J=2.1 Hz, 1H), 6.60(d, J=7.5 Hz, 1H), 6.80(bs, 1H), 6.90(bs, 1H), 6.93-6.96(m, 2H), 7.10-7.18(m, 2H)

EXAMPLE 278

1-(3-nitro-2-methylbenzyl)-4-chloropyridin-2(1H)-one $^1$H NMR (CDCl$_3$, 300 MHz) δ 2.38(s, 3H), 5.38(s, 2H), 6.54(dd, 1H), 7.27(d, J=7.8 Hz, 1H), 7.45(t, J=7.9 Hz, 1H), 7.79(d, J=7.8 Hz, 2H), 8.21(s, 1H)

EXAMPLE 279

1-(3-amino-2-methylbenzyl)-4-chloropyridin-2(1H)-one $^1$H NMR (CDCl$_3$, 300 MHz) δ 1.94(s, 3H), 5.08(s, 2H), 6.23-6.28(m, 2H), 6.63(d, J=7.8 Hz, 1H), 6.90(t, J=7.8 Hz, 1H), 8.11(s, 1H)

EXAMPLE 280

1-(3-amino-2-methylbenzyl)-4-(2-(thiophene-2-yl)ethylamino)pyridine-2-(1H)-one $^1$H NMR (CDCl$_3$, 300 MHz) δ 2.02(s, 3H), 3.07(t, J=6.8 Hz, 2H), 3.37(t, J=6.5 Hz, 2H), 4.97(s, 2H), 5.64(d, J=8.1 Hz, 2H), 6.55(d, J=7.5 Hz, 1H), 6.75-6.83(m, 3H), 6.88-6.91(m, 1H), 7.00(t, J=7.5 Hz, 1H), 7.12(d, J=5.1 Hz, 1H)

TEST EXAMPLE 1

Minimum Inhibitory Concentration (MIC)

Antibacterial activities of the compounds synthesized in the Examples were assessed by measuring their MIC values for standard strains. Specifically, MIC value was measured by conducting the following steps: diluting a test compound according to a two-fold dilution method; dispersing the resulting dilution in a Müller-Hinton agar broth; inoculating 2 ml of the standard strain culture having a concentration of 10$^7$ cfu (colony forming unit)/ml; and incubating the mixture for 20 hrs at 37° C. The resulting MIC values were in the range of 128 to 0.2 μg/ml, preferably, 1 to 0.2 μg/ml. These results reveal that the compounds of the present invention have superior antibacterial activity against various infectious bacterial strains including MRSA strain.

What is claimed is:

1. A compound having a formula (I) or a pharmaceutically acceptable salt, acid, or ester:

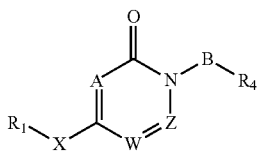 (I)

wherein,
R₁ is
C$_{2-8}$ alkyl which contains one or more substituents selected from the group consisting of:
C$_{3-8}$ cycloalkyl, C$_{3-8}$ heterocycloalkyl, benzyloxy, aryl, heteroaryl, substituted aryl, and substituted heteroaryl,
wherein said substituted aryl and substituted heteroaryl each contain one or more substituents selected from the group consisting of C$_{1-6}$alkyl, C$_{3-8}$ cycloalkyl, C$_{3-8}$ heterocycloalkyl, alkyloxy, amino, alkylamino, carboxyl, nitro, sulfonylamide, alkylsulfonyl, amide, dioxoisoindole, trihaloalkyl, and aryl;
A is CH;
B is CH$_2$;
R$_4$ is a substituted aryl containing one or more substituents selected from the group consisting of:
hydroxyl, halogen, C$_{1-6}$ alkyl, C$_{3-8}$ cycloalkyl, C$_{3-8}$ heterocycloalkyl, alkyloxy, amino, alkylamino, carboxyl, nitro, sulfonylamide, alkylsulfonyl, amide, dioxoisoindole, trihaloalkyl, aryl, heteroaryl, and substituted heteroaryl,
wherein said substituted aryl and substituted heteroaryl each contain one or more substituents selected from the group consisting of:
C$_{1-6}$ alkyl, C$_{3-8}$ cycloalkyl, C$_{3-8}$ heterocycloalkyl, alkyloxy, amino, alkylamino, carboxyl, nitro, sulfonylamide, alkylsulfonyl, amide, dioxoisoindole, trihaloalkyl, and aryl;
W is CH;
Z is CH ; and
X is O.

2. The compound of claim 1 wherein the alkyl group of R$_1$ is linear.

3. The compound of claim 1 wherein the alkyl group of R$_1$ is branched.

4. The compound of claim 1, which is selected from the group consisting of:
4-(4-benzyloxy-butoxy)-1-(2,4-dichloro-benzyl)-1H-pyridin-2-one;
4-(5-benzyloxy-pentyloxy)-1-(2,4-dichloro-benzyl)-1H-pyridin-2-one;
1-(2,4-dichloro-benzyl)-4-(5-morpholin-4-yl-pentyloxy)-1H-pyridin-2-one;
1-(2,4-dichloro-benzyl)-4-(2-thiophen-2-yl-ethoxy)-1H-pyridin-2-one;
1-(2,4-dichloro-benzyl)-4-(2-thiophen-3-yl-ethoxy)-1H-pyridin-2-one;
1-(2,4-dichloro-benzyl)-4-(2-pyrrol-1-yl-ethoxy)-1H-pyridin-2-one;
1-(2,4-dichloro-benzyl)-4-(3-pyrrol-1-yl-propoxy)-1H-pyridin-2-one;
1-(3-amino-2-methyl-benzyl)-4-(2-thiophen-2-yl-ethoxy)-1H-pyridin-2-one;
1-(3-amino-2-methyl-benzyl)-4-(2-pyrrol-1-yl-ethoxy)-1H-pyridin-2-one;
1-(3-amino-2-methyl-benzyl)-4-[2-(4-methyl-thiazol-5-yl)-ethoxy]-1H-pyridin-2-one;
1-(3-amino-2-methyl-benzyl)-4-(2-(5-bromothiophen-2-yl)-ethoxy)-1H-pyridin-2-one;
1-(3-amino-2-methyl-benzyl)-4-(2-(5-fluorothiophen-2-yl)-ethoxy)-1H-pyridin-2-one;
1-[3-(2-Hydroxy-ethylamino)-2-methyl-benzyl]-4-(2-thiophen-2-yl-ethoxy)-1H-pyridin-2-one;
1-[3-(cyclopropylmethyl-amino)-2-methyl-benzyl]-4-(2-thiophen-2-yl-ethoxy)-1H-pyridin-2-one;
1-[2-methyl-3-(2-pyrrol-1-yl-ethylamino)-benzyl]-4-(2-thiophen-2-yl-ethoxy)-1H-pyridin-2-one;
1[2-methyl-3-(2-oxo-2-pyrrolidin-1-yl-ethylamino)-benzyl]-4-(2-thiophen-2-yl-ethoxy)- 1H-pyridin-2-one;
1-[2-methyl-3-(2-oxo-2-piperidin-1-yl-ethylamino)-benzyl]-4-(2-thiophen-2-yl-ethoxy)-1H-pyridin-2-one;
1-{methyl-3-[2-(4-methyl-piperazin-1-yl)-2-oxo-ethylamino]-benzyl}-4-(2-thiophen-2-yl-ethoxy)-1H-pyridin-2-one;
1 -[2-methyl-3-(2-morpholin-4-yl-2-oxo-ethylamino)-benzyl]-4-(2-thiophen-2-yl-ethoxy) - 1H-pyridin-2-one;
1-(3 -amino-2-methyl-benzyl)-4-(2-furan-2-yl-ethoxy)-1H-pyridin-2-one;
1-(3-amino-2-methyl-benzyl)-4-[2-(5-methyl-thiophen-2-yl)-ethoxy]-1H-pyridin-2-one;
1-(3-amino-2-methyl-benzyl)-4-[2-(5-chloro-thiophen-2-yl)-ethoxy]-1H-pyridin-2-one;
1-(2,4-dichloro-benzyl)-4- [2-(3-methyl-thiophen-2-yl)-ethoxy]-1H-pyridin-2-one;
1-(3-amino-2-methyl-benzyl)-4-(2-benzo [b]thiophen-3-yl-ethoxy)-1H-pyridin-2-one;
1-(3-amino-2-methyl-benzyl)-4- [2-(5-chloro-3-methyl-benzo [b]thiophen-2-yl)-ethoxy]-1H-pyridin-2-one;
1-(3-amino-2-methyl-benzyl)-4- [2-(3-methyl-benzo[b]thiophen-2-yl)-ethoxy]-1H -pyridin-2-one;
1-(3-amino-2-methyl-benzyl)-4-[2-(5-methyl-furan-2-yl)-ethoxy]-1H-pyridin-2-one;
1-(3-amino-2-methyl-benzyl)-4-[2-(5-ethyl-furan-2-yl)-ethoxy]- 1H-pyridin-2-one;
1-[-3(2-dimethylamino-ethylamino)-2-methyl-benzyl]-4-(2-thiophen-2-yl-ethoxy) -1H-pyridine-2-one;
1-(3-amino-2-methyl-benzyl)-4-[2-(5-methylsulfanyl-thiophen-2-yl)-ethoxy]-1H -pyridin-2-one;
1-(3-amino-2-methyl-benzyl)-4-(2-benzofuran-2-yl-ethoxy)-1H-pyridin-2-one;
1-(3-amino-2-methyl-benzyl)-4-[2-(3-methyl-isoxazol-5-yl)-ethoxy]-1H-pyridin-2-one;
1-(3-amino-2-methyl-benzyl)-4-[2-(4,5-dimethyl-thiophen-2-yl)-ethoxy]-1H-pyridin -2-one;
1-(3-amino-2-methyl-benzyl)-4-[2-(5-ethyl-thiophen-2-yl)-ethoxy]-1H-pyridin-2-one;
1-(3-amino-2,6-dichloro-benzyl)-4-(2-thiophen-2-yl-ethoxy)-1H-pyridin-2-one;
N-{2-methyl-3[2-oxo-4-(2-thiophen-2-yl-ethoxy)-2H-pyridin-1-ylmethyl]-phenyl}-acetamide;
1-[2-methyl-3-(2-piperidin-1-yl-ethylamino)-benzyl]-4-(2-thiophen-2-yl-ethoxy)-1H -pyridin-2-one;
1-[2-methyl-3-(2-morpholin-4-yl-ethylamino)-benzyl]-4-(2-thiophen-2-yl-ethoxy) -1H-pyridin-2-one;
1-(3-amino-2-methyl-benzyl)-4-[2-(4-bromo-thiophen-2-yl)-ethoxy]-1H-pyridin-2-one;
1-(6-chloro-benzo[1,3]dioxol-5-ylmethyl)-4-(2-pyrrol-1-yl-ethoxy)-1H-pyridin-2-one;
1-(6-chloro-benzo[1,3]dioxol-5-ylmethyl)-4-(2-thiophen-2-yl-ethoxy)-1H-pyridin-2-one;

1[2-methyl-3-(2-pyrrolidin-1-yl-ethylamino)-benzyl]-4-(2-thiophen-2-yl-ethoxy)-1H-pyridin-2-one;

N-(2-{2-methyl-3-[2-oxo-4-(2-thiophen-2-yl-ethoxy)-2H-pyridin-1-ylmethyl]-phenylamino}-ethyl)-acetamide;

1-{2-methyl-3-[(pyridin-3-ylmethyl)-amino]-benzyl}-4-(2-thiophen-2-yl-ethoxy)-1H-pyridin-2-one;

1-{2-methyl-3-[(pyridin-4-ylmethyl)-amino]-benzyl}-4-(2-thiophen-2-yl-ethoxy)-1H-pyridin-2-one;

1-{2-methyl-3-[(thiazol-4-ylmethyl)-amino]-benzyl}-4-(2-thiophen-2-yl-ethoxy)-1H-pyridin-2-one;

1-[3(4-methoxy-benzyloxy)-2-methyl-benzyl]-4-(2-thiophen-2-yl-ethoxy)-1H-pyridin-2-one;

1-{3-[(3,5-dimethyl-isoxazol-4-ylmethyl)-amino]-2-methyl-benzyl}-4-(2-thiophen-2-yl-ethoxy)-1H-pyridin-2-one;

1-(3-hydroxy-2-methyl-benzyl)-4-(2-thiophen-2-yl-ethoxy)-1H-pyridin-2-one;

1-{2-methyl-3-[(1-methyl-pyrrolidin-2-ylmethyl)-amino]-benzyl}-4-(2-thiophen-2-yl-ethoxy)-1H-pyridin-2-one; and 1-{2-methyl-3-[2-(1-methyl-pyrrolidin-2-yl)-ethylamino]-benzyl}-4-(2-thiophen-2-yl-ethoxy)-1H-pyridin-2-one.

5. A compound of claim 1 which is an acid selected from the group consisting of hydrochloric, sulfuric, phosphoric, p-toluenesulfonic, methanesulfonic, hydrobromic and camphorsulfonic.

6. A method of preparing the compound of Formula (I) of claim 1 comprising:
forming a solution of a pyridone derivative comprising an alcohol or amine functionality and NaH or potassium t-butoxide in dimethylformamide;
combining said solution with a halide compound of the formula k-m-h where h is chloride or bromide; m is benzyl, or 2-methylbenzyl; and k is 2-chloro, 3-chloro, 4-chloro, 3-nitro, 4-nitro, 2,5-dichloro, 2,4-dichloro, 4-methoxy, 4-methyl, or 6-chloro-pyridin-3-, or 4-amino;
stirring said combination for 30 minutes at room temperature to form a reaction product which includes one or more of the compounds of Formula (I) described in claim 1.

7. The method of claim 6 which further comprises: isolating said one or more compounds of Formula (I) from said reaction product by column chromatography.

8. The method of claim 7 which further comprises:
hydrogenating said isolated product with Pd/C to form a compound having a hydroxyl substituent.

9. The method of claim 8 which further comprises:
substituting said hydroxyl substituent by a substituent selected from the group consisting of (a) H; (b) $C_{1-8}$ alkyl, $C_{2-8}$ alkenyl, or $C_{2-8}$ alkynyl; (c) aryl, $C_{3-8}$ cycloalkyl or $C_{3-8}$ cycloalkenyl; (d) $C_{1-8}$ alkyl, $C_{2-8}$ alkenyl, $C_{2-8}$ alkynyl, each containing one or more heteroatoms selected from N, S or O; and (e) a substituted group (b), (c), or (d), said group each containing one or more substituents selected from the group consisting of hydroxyl, halogen, $C_{1-6}$ alkyl, $C_{3-8}$ cycloalkyl, $C_{3-8}$ heterocycloalkyl, alkyloxy, amino, alkylamino, carboxyl, nitro, sulfonylamide, alkylsulfonyl, amide, dioxoisoindole, trihaloalkyl, aryl and heteroaryl.

10. An anti-bacterial composition comprising the compound of Formula (I) of claim 1 as an active ingredient.

11. The anti-bacterial composition of claim 10, which is in the form of a formulation comprising the compound of Formula (I) in the range of 50 to 5,000 mg, the formulation being selected from the group consisting of oral, sublingual, inhalation, topical, rectal, and injection formulations.

12. The anti-bacterial composition of claim 11, which is in the form of a formulation comprising the compound of Formula (I) in the range of 150 to 3,000 mg.

13. The anti-bacterial composition of claim 11, which is in the form of a formulation comprising the compound of Formula (I) in the range of 50 to 2,000 mg.

14. A method for treating a bacteria-related disease, wherein the method comprises administering to a human in need thereof, an effective amount of a formulation of claim 11, wherein the bacteria-related disease is selected from the group consisting of urinary tract infection, urinary tract sepsis, respiratory infection, respiratory sepsis, skin tissue infection, and skin tissue sepsis.

15. The method of claim 14, wherein said formulation is in the form of a tablet, capsule or pill.

16. The method of claim 14, wherein the administration is by subcutaneous, intravenous, intramuscular, intra-articular, intra-synovial, intrasternal, intrathecal, intrahepatic, intralesional, or intracranial injection.

17. A kit for use in the treatment of bacteria-related disease which comprises: (a) the formulation of claim 11 and (b) a syringe.

18. A kit for use in a method of treating bacteria related disease comprising the formulation of claim 11 in the form of a powder, granules, or concentrate and a solvent for reconstituting said pharmaceutical composition to provide an oral dosage form.

* * * * *